US008389247B2

(12) United States Patent
Ruano et al.

(10) Patent No.: US 8,389,247 B2
(45) Date of Patent: Mar. 5, 2013

(54) PHYSIOGENOMIC METHOD FOR PREDICTING DIABETES AND METABOLIC SYNDROMES INDUCED BY PSYCHOTROPIC DRUGS

(75) Inventors: Gualberto Ruano, Milford, CT (US); Andreas Windemuth, South Glastonbury, CT (US); John W. Goethe, Avon, CT (US)

(73) Assignee: Genomas, Inc., Hartford, CT (US)

( * ) Notice: Subject to any disclaimer, the term of this patent is extended or adjusted under 35 U.S.C. 154(b) by 0 days.

(21) Appl. No.: 13/195,116

(22) Filed: Aug. 1, 2011

(65) Prior Publication Data

US 2011/0312508 A1 Dec. 22, 2011

Related U.S. Application Data

(62) Division of application No. 11/694,247, filed on Mar. 30, 2007, now Pat. No. 8,012,718.

(60) Provisional application No. 60/744,101, filed on Mar. 31, 2006.

(51) Int. Cl.
*C12P 19/34* (2006.01)

(52) U.S. Cl. ................................ 435/91.2
(58) Field of Classification Search .......... 435/91.2
See application file for complete search history.

(56) References Cited

U.S. PATENT DOCUMENTS

| 2003/0092019 A1 | 5/2003 | Meyer et al. |
| 2006/0024715 A1 | 2/2006 | Liu et al. |
| 2006/0278241 A1 | 12/2006 | Ruano |

OTHER PUBLICATIONS

Cleveland, et al; "Locally Weighted Regression: An Approach to Regression Analysis by Local Fitting"; Journal of the American Statistical Association; 83; pp. 596-610; (1988).
Cleveland; "Robust Locally Weighted Regression and Smoothing Scatterplots"; Journal of the American Statistical Association; 74; pp. 829-836; (1979).
Fantoni, et al; "Evaluation and Management of Metabolic and Coagulative Disorders in HIV-Infected Patients Receiving Highly Active Antiretroviral Therapy"; AIDS; 17; pp. S162-S169; (2003).
Hastie, et al; "Generalized Additive Models"; Statistical Science; 1; pp. 297-318; (1986).
Benjamini and Hochberg; "On the Adaptive Control of the False Discovery Rate in Multiple Testing With Independent Statistics"; Journal of Educational and Behavioral Statistics; 25; pp. 60-83; (2000).
Benjamini and Hochberg; "Controlling the False Discovery Rate: A Practical and Powerful Approach to Multiple Testing"; Journal of the Royal Statistical Society; Series B (methodological); 57; pp. 289-300; (1995).
Reiner et al; "Identifying Differentially Expressed Genes Using False Discovery Rate Controlling Procedures"; Bioinformatics; 19; pp. 368-375; (2003).
Ruano, et al; "Physiogenomic Comparison of Weight Profiles of Olanzapine- and Risperidone-Treated Patients"; Molecular Psychiatry; pp. 1-9; (2007).
Steenland, et al; "Empirical Bayes Adjustments for Multiple Results in Hypothesis-Generating or Surveillance Studies"; Cancer Epidemiology, Biomarkers & Prevention; 9; pp. 895-903; (2000).
Nelson et al., Genome Research, vol. 14, pp. 1664-1668, 2004.
www.genecards.org/cgi-bin/carddisp.pl?gene=npy&suff=txt, see pp. 1-17, Jul. 2009.
www.genecards.org/cgi-bin/carddisp.pl?gene=lepr&suff=txt, see pp. 1-39, Jul. 2009.
Hirschhorn et al. Genetics in Medicine. vol. 4, No. 2, pp. 45-61, Mar. 2002.
Ioannidis et al. Nature Genetics, vol. 29, pp. 306-209, Nov. 2001.
Halushka et al. Nature., vol. 22, pp. 239-247, 1999.
Durrleman, et al; "Flexible Regression Models with Cubic Splines"; Statistics in Medicine; 8; pp. 551-561; (1989).
Ruano, et al; "Physiogenomic Comparison of Weight Profiles of Olanzapine- and Risperidone-Treated Patients"; Molecular Psychiatry; 12; pp. 474-482; (2007).

*Primary Examiner* — Gary Benzion
*Assistant Examiner* — Cynthia Wilder
(74) *Attorney, Agent, or Firm* — Cantor Colburn LLP

(57) ABSTRACT

The invention is generally directed to a physiogenomic method for predicting diabetes and metabolic syndromes induced by psychotropic drugs. In one embodiment, the invention relates to the use of genetic variants of marker genes to predict the likelihood that an individual will experience undesirable metabolic side effects as a result of the use of a drug including, but not limited to, psychotropic drugs. The invention also relates to methods predicting the likelihood of diabetes and metabolic syndromes induced by the use of drugs with undesirable metabolic side effects.

3 Claims, No Drawings

PHYSIOGENOMIC METHOD FOR PREDICTING DIABETES AND METABOLIC SYNDROMES INDUCED BY PSYCHOTROPIC DRUGS

This application is a divisional of U.S. application Ser. No. 11/694,247, filed on Mar. 30, 2007, which claims the benefit of U.S. provisional application Ser. No. 60/744,101, filed Mar. 31, 2006, the entire disclosure of which are hereby incorporated by reference.

FIELD OF INVENTION

The present invention is in the field of physiological genomics, hereafter referred to as "physiogenomics". More specifically, the invention relates to the use of genetic variants of marker genes to predict the likelihood that an individual will experience undesirable metabolic side effects as a result of the use of a drug including, but not limited to, psychotropic drugs. The invention also relates to methods predicting the likelihood of diabetes and metabolic syndromes induced by the use of drugs with undesirable metabolic side effects.

BACKGROUND OF INVENTION

The psychotropic drugs are widely utilized in the treatment of schizophrenia and schizoaffective disorder. The psychotropic drugs olanzapine (Zyprexa®, Eli Lilly & Co.), risperidone (Risperdal®, Janssen, Johnson & Johnson), quetiapine (Seroquel®, Astra Zeneca) and clozapine (Clozaril®, Novartis) accounted for $5 billion in worldwide sales in 2000. While approximately 50% of prescriptions for these drugs are written for schizophrenia, other indications are becoming increasingly important, including bipolar disorder and depression, which each represent about 15% of prescriptions, and obsessive compulsive and anxiety disorders which are also beginning to be treated with these drugs.

Among psychotropic drugs, olanzapine and clozapine have been observed to induce weight gain, diabetes and other metabolic derangements in 50% of treated patients. The most serious medical side effect is the progression to Diabetes and Metabolic Syndromes (DIMS). These metabolic syndromes are diagnosed by the combination of abdominal obesity, atherogenic dyslipidemia, high fasting glucose, and elevated blood pressure. Specifically, DIMS is characterized by the following abnormalities occurring individually or in combination: (1) large waist circumference (>102 cm in men, 88 cm in women), (2) elevated serum triglycerides (>150 mg/dL), (3) depressed high density lipoprotein (HDL, <40 mg/dL in men, 50 mg/dL in women), (4) elevated blood pressure (systolic >130 mm Hg or diastolic ≧80 mmHg), and (5) elevated serum glucose (>110 mg/dL). The medical community is just now beginning to appreciate how disabling and burdensome DIMS can be to patients already suffering from psychiatric disease. The specter of obesity and DIMS could reduce compliance with psychotropic drugs and lead to low self-esteem and social withdrawal in already marginalized patients. Further, obesity and diabetes introduce serious medical complications (e.g. vascular disease, neuropathy), which increase the need to avoid the progression to metabolic syndromes in the first place. Hence, judicious selection of psychotropic therapeutic strategies to improve symptoms must be balanced with the expense of equally detrimental drug side effects. The need for "double prevention," i.e., prevention of schizophrenia by early psychiatric management with psychotropic drugs and prevention of drug side effects by early medical management of the metabolic side effects, is therefore apparent.

The development of hyperglycemia and other metabolic syndromes cannot be explained solely on grounds of action of psychotropic drugs on the central nervous system and satiety for two principle reasons. First, other antagonists of serotonin, histamine, or adrenergic receptors, whether alone or in combination, do not provoke DIMS. Second, a high proportion of HIV-infected patients receiving protease inhibitors as part of the "Highly Active Anti-Retroviral Therapy" (HAART) regimen also develop DIMS (Fantoni, et al. 2003, AIDS 17 Suppl 1, S162). In contrast to psychotropic drugs, protease inhibitors do not influence appetite or satiety. It is therefore likely that unknown or unexpected pathways coalesce into DIMS.

The medical community would benefit from screening methods which identify individuals at risk of developing DIMS. The emerging field of physiogenomics offers an important approach for integrating genotype, phenotype, and population analysis of functional variability among individuals. In physiogenomics, genetic markers (e.g. single nucleotide polymorphisms or "SNPs") are analyzed to discover statistical associations to physiological characteristics or outcomes in populations of individuals. Physiogenomics allows screening hundreds of candidate genes and physiological measurements of psychiatric disorders and metabolic syndromes, to explore an extensive variety of hypothetical pathways that might be involved in the development of psychotropic drug DIMS.

It is therefore an object of the present invention to provide physiogenomic methods for identifying individuals at risk of developing DIMS or other metabolic side effects associated with the class of psychotropic drugs or associated with specific psychotropic drugs.

SUMMARY OF INVENTION

The present invention provides a marker gene set comprising a plurality of single nucleotide polymorphic gene variants, wherein the presence of any one of said single nucleotide polymorphic gene variants in a human is correlated with a patient's risk for developing one or more adverse side effects associated with the use of a drug, especially a psychotropic drug, a glitazone drug, or a protease inhibitor drug. The adverse side effect may be associated with, for example, a change in one or more of total cholesterol (TC) level, LDL cholesterol level, HDL cholesterol level, total cholesterol to HDL cholesterol ratio, triglyceride level, blood glucose level, systolic blood pressure, diastolic blood pressure, body mass (BMS), body mass index (BMI), waist circumference, and metabolic syndromes index (MSI). In an particularly interesting embodiment, the adverse side effect is Diabetes and Metabolic Syndromes (DIMS). Marker gene sets are provided for predicting the likelihood of such side effects associated with the class of drug or an individual drug. In preferred embodiments, the class of drug is a psychotropic drug and the specific drug includes arapiprazole (Abilify®, Bristol Myers Squibb), clozapine, olanzapine, quetiapine, risperidone, and ziprasidone (Geodon®, Pfizer)

DETAILED DESCRIPTION OF THE INVENTION

The following definitions will be used in the specification and claims:

1. Correlations or other statistical measures of relatedness between DNA variants and physiologic parameters are as used by one of ordinary skill in this art.

2 As use herein, "polymorphism" refers to DNA sequence variations in the cellular genomes of animals, preferably mammals. Such variations include mutations, single nucleotide changes, insertions and deletions. Single nucleotide polymorphism ("SNP") refers to those differences among samples of DNA in which a single nucleotide pair has been substituted by another.

3. As used herein, "variants" or "variance" is synonymous with polymorphism.

4. As used herein, "phenotype" refers to any observable or otherwise measurable physiological, morphological, biological, biochemical or clinical characteristic of an organism. The point of genetic studies is to detect consistent relationships between phenotypes and DNA sequence variation (genotypes).

5. As used herein, "genotype" refers to the genetic composition of an organism. More specifically, "genotyping" as used herein refers to the analysis of DNA in a sample obtained from a subject to determine the DNA sequence in one or more specific regions of the genome, for example, at a gene that influences a disease or drug response.

6. As used herein, the term "associated with" in connection with a relationship between a genetic characteristic (e.g., a gene, allele or polymorphism) and a disease or condition means that there is a statistically significant level of relatedness based on any accepted statistical measure of relatedness.

7. As used herein, a "gene" is a sequence of DNA present in a cell that directs the expression of biochemicals, i.e., proteins, through, most commonly, a complimentary RNA.

8. As used herein, a "drug associated with undesirable metabolic effects" is any drug that, when administered to a patient, causes side effects related to metabolism. Examples of such drugs are psychotropic drugs, drugs used in glitazone therapy, and protease inhibitors.

It has surprisingly been found that physiogenomic methods can be employed to identify genetic markers associated with the likelihood of developing DIMS. Thus, a patient can be assayed for the presence of one or more of genetic markers and a personalized therapeutic regimen developed based on the presence or absence of the marker, the specific allele (i.e., heterozygous or homozygous), and the predictive ability of the marker.

The physiogenomics methods employed in the present invention are described generally in U.S. patent application Ser. No. 11/010,716, the contents of which are hereby incorporated by reference. Briefly, the physiogenomics method typically comprises (a) selecting a plurality of genetic markers based on an analysis of the entire human genome or a fraction thereof; (b) identifying significant covariates among demographic data and the other phenotypes preferably by linear regression methods (e.g., $R^2$ analysis followed by principal component analysis); (c) performing for each selected genetic marker an unadjusted association test using genetic data; (d) using permutation testing to obtain a non-parametric and marker complexity independent probability ("p") value for identifying significant markers, wherein p denotes the probability of a false positive, and significance is shown by $p<0.10$, more preferably $p<0.05$, even more preferably $p<0.01$, and even more preferably $p<0.001$; (e) constructing a physiogenomic model by multivariate linear regression analyses and model parameterization for the dependence of the patient's response with respect to the markers, wherein the physiogenomic model has $p<0.10$, preferably $p<0.05$, more preferably $p<0.01$, and even more preferably $p<0.001$; and (f) identifying one or more genes not associated with a particular outcome in the patient to serve as a physiogenomic control.

In a specific embodiment, the array consists of several hundred genes and is capable of genotyping hundreds of DNA polymorphisms simultaneously. Candidate genes for use in the arrays of the present invention are identified by various means including, but not limited to, pre-existing clinical databases and DNA repositories, review of the literature, and consultation with clinicians, differential gene expression models, physiological pathways in metabolism, cholesterol and lipid homeostasis, and from previously discovered genetic associations. In a preferred embodiment, the candidate genes are selected from those shown in Table 1.

TABLE 1

| SNP | Seq. ID No. | Gene | Gene Description |
|---|---|---|---|
| rs1128503 | 123 | ABCB1 | ATP-binding cassette, sub-family B (MDR/TAP), member 1 |
| rs2032582 | 132 | ABCB1 | ATP-binding cassette, sub-family B (MDR/TAP), member 1 |
| rs1045642 | 382 | ABCB1 | ATP-binding cassette, sub-family B (MDR/TAP), member 1 |
| rs916829 | 40 | ABCC8 | ATP-binding cassette, sub-family C (CFTR/MRP), member 8 |
| rs3758947 | 244 | ABCC8 | ATP-binding cassette, sub-family C (CFTR/MRP), member 8 |
| rs722341 | 254 | ABCC8 | ATP-binding cassette, sub-family C (CFTR/MRP), member 8 |
| rs4148189 | 177 | ABCG5 | ATP-binding cassette, sub-family G (WHITE), member 5 (sterolin 1) |
| rs2052130 | 386 | ABP1 | amiloride binding protein 1 (amine oxidase (copper-containing)) |
| rs1049793 | 266 | ABP1 | amiloride binding protein 1 (amine oxidase (copper-containing)) |
| rs2053670 | 387 | ACACA | acetyl-Coenzyme A carboxylase alpha |
| rs2946342 | 388 | ACACA | acetyl-Coenzyme A carboxylase alpha |
| rs2229416 | 102 | ACACA | acetyl-Coenzyme A carboxylase alpha |
| rs8081866 | 162 | ACACA | acetyl-Coenzyme A carboxylase alpha |
| rs4795180 | 361 | ACACA | acetyl-Coenzyme A carboxylase alpha |
| rs2430683 | 207 | ACACB | acetyl-Coenzyme A carboxylase beta |
| rs2241220 | 314 | ACACB | acetyl-Coenzyme A carboxylase beta |
| rs34274 | 352 | ACACB | acetyl-Coenzyme A carboxylase beta |
| rs10890819 | 76 | ACAT1 | acetyl-Coenzyme A acetyltransferase 1 (acetoacetyl Coenzyme A thiolase) |

TABLE 1-continued

| SNP | Seq. ID No. | Gene | Gene Description |
|---|---|---|---|
| rs11212515 | 191 | ACAT1 | acetyl-Coenzyme A acetyltransferase 1 (acetoacetyl Coenzyme A thiolase) |
| rs25683 | 389 | ACAT2 | acetyl-Coenzyme A acetyltransferase 2 (acetoacetyl Coenzyme A thiolase) |
| rs2146162 | 33 | ACAT2 | acetyl-Coenzyme A acetyltransferase 2 (acetoacetyl Coenzyme A thiolase) |
| rs15982 | 329 | ACAT2 | acetyl-Coenzyme A acetyltransferase 2 (acetoacetyl Coenzyme A thiolase) |
| rs4364 | 390 | ACE | angiotensin I converting enzyme (peptidyl-dipeptidase A) 1 |
| rs2229839 | 391 | ACE | angiotensin I converting enzyme (peptidyl-dipeptidase A) 1 |
| rs4333 | 139 | ACE | angiotensin I converting enzyme (peptidyl-dipeptidase A) 1 |
| rs4305 | 180 | ACE | angiotensin I converting enzyme (peptidyl-dipeptidase A) 1 |
| rs1800764 | 328 | ACE | angiotensin I converting enzyme (peptidyl-dipeptidase A) |
| rs7636 | 392 | ACHE | acetylcholinesterase (YT blood group) |
| rs3757868 | 234 | ACHE | acetylcholinesterase (YT blood group) |
| rs3847063 | 356 | ACHE | acetylcholinesterase (YT blood group) |
| rs1656943 | 393 | ADIPOQ | adiponectin, C1Q and collagen domain |
| rs2058112 | 91 | ADIPOR2 | adiponectin receptor 2 |
| rs7975375 | 227 | ADIPOR2 | adiponectin receptor 2 |
| rs3766560 | 49 | ADORA1 | adenosine A1 receptor |
| rs903361 | 200 | ADORA1 | adenosine A1 receptor |
| rs3761422 | 248 | ADORA2A | adenosine A2a receptor |
| rs2324082 | 482 | ADORA2B | adenosine A2b receptor |
| rs758857 | 7 | ADORA2B | adenosine A2b receptor |
| rs2015353 | 315 | ADORA2B | adenosine A2b receptor |
| rs2298191 | 265 | ADORA3 | adenosine A3 receptor |
| rs1415793 | 366 | ADORA3 | adenosine A3 receptor |
| rs7816340 | 46 | ADRA1A | adrenergic, alpha-1A-, receptor |
| rs573542 | 240 | ADRA1A | adrenergic, alpha-1A-, receptor |
| rs2229126 | 374 | ADRA1A | adrenergic, alpha-1A-, receptor |
| rs1800544 | 66 | ADRA2A | adrenergic, alpha-2A-, receptor |
| rs521674 | 222 | ADRA2A | adrenergic, alpha-2A-, receptor |
| rs1800545 | 274 | ADRA2A | adrenergic, alpha-2A-, receptor |
| rs2229169 | 308 | ADRA2B | adrenergic, alpha-2B-, receptor |
| rs1801252 | 55 | ADRB1 | adrenergic, beta-1-, receptor |
| rs1801253 | 226 | ADRB1 | adrenergic, beta-1-, receptor |
| rs2429511 | 365 | ADRB1 | adrenergic, beta-1-, receptor |
| rs1042713 | 67 | ADRB2 | adrenergic, beta-2-, receptor, surface |
| rs1042718 | 195 | ADRB2 | adrenergic, beta-2-, receptor, surface |
| rs4994 | 333 | ADRB3 | adrenergic, beta-3-, receptor |
| rs5049 | 101 | AGT | angiotensinogen (serine (or cysteine) proteinase inhibitor, clade A (alpha-1 antiproteinase, antitrypsin), member 8) |
| rs4762 | 353 | AGT | angiotensinogen (serine (or cysteine) proteinase inhibitor, clade A (alpha-1 antiproteinase, antitrypsin), member 8) |
| rs2933249 | 394 | AGTR1 | angiotensin II receptor, type 1 |
| rs931490 | 137 | AGTR1 | angiotensin II receptor, type 1 |
| rs12695902 | 296 | AGTR1 | angiotensin II receptor, type 1 |
| rs760427 | 395 | AIRE | autoimmune regulator (autoimmune polyendocrinopathy candidiasis ectodermal dystrophy) |
| rs1003854 | 232 | AIRE | autoimmune regulator (autoimmune polyendocrinopathy candidiasis ectodermal dystrophy) |
| rs2494746 | 290 | AKT1 | v-akt murine thymoma viral oncogene homolog 1 |
| rs7254617 | 396 | AKT2 | v-akt murine thymoma viral oncogene homolog 2 |
| rs7247515 | 32 | AKT2 | v-akt murine thymoma viral oncogene homolog 2 |
| rs4802071 | 106 | AKT2 | v-akt murine thymoma viral oncogene homolog 2 |
| rs1283694 | 86 | ANGPT1 | angiopoietin 1 |
| rs1283718 | 241 | ANGPT1 | angiopoietin 1 |
| rs2514869 | 311 | ANGPT1 | angiopoietin 1 |
| rs4933200 | 307 | ANKRD1 | ankyrin repeat domain 1 (cardiac muscle) |
| rs12718465 | 385 | APOA1 | apolipoprotein A-I |
| rs670 | 397 | APOA1 | apolipoprotein A-I |
| rs4225 | 119 | APOA1 | apolipoprotein A-I |
| rs5070 | 351 | APOA1 | apolipoprotein A-I |
| rs5085 | 62 | APOA2 | apolipoprotein A-II |
| rs5092 | 22 | APOA4 | apolipoprotein A-IV |
| rs675 | 51 | APOA4 | apolipoprotein A-IV |
| rs662799 | 481 | APOA5 | apolipoprotein A-V |
| rs1800481 | 398 | APOB | apolipoprotein B (including Ag(x) antigen) |
| rs3791981 | 124 | APOB | apolipoprotein B (including Ag(x) antigen) |

TABLE 1-continued

| SNP | Seq. ID No. | Gene | Gene Description |
|---|---|---|---|
| rs1801701 | 302 | APOB | apolipoprotein B (including Ag(x) antigen) |
| rs676210 | 371 | APOB | apolipoprotein B (including Ag(x) antigen) |
| rs10424339 | 399 | APOC1 | apolipoprotein C-I |
| rs5166 | 400 | APOC2 | apolipoprotein C-II |
| rs4520 | 111 | APOC3 | apolipoprotein C-III |
| rs2071521 | 224 | APOC3 | apolipoprotein C-III |
| rs5158 | 401 | APOC4 | apolipoprotein C-IV |
| rs2288911 | 90 | APOC4 | apolipoprotein C-IV |
| rs439401 | 73 | APOE | apolipoprotein E |
| rs429358 | 83 | APOE | apolipoprotein E |
| rs405509 | 197 | APOE | apolipoprotein E |
| rs446037 | 282 | APOE | apolipoprotein E |
| rs7412 | 297 | APOE | apolipoprotein E |
| rs4301822 | 259 | APOF | apolipoprotein F |
| rs8178847 | 63 | APOH | apolipoprotein H (beta-2-glycoprotein I) |
| rs136163 | 1 | APOL1 | apolipoprotein L, 1 |
| rs1001293 | 129 | APOL2 | apolipoprotein L, 2 |
| rs132653 | 94 | APOL3 | apolipoprotein L, 3 |
| rs132661 | 286 | APOL3 | apolipoprotein L, 3 |
| rs132642 | 332 | APOL3 | apolipoprotein L, 3 |
| rs2005590 | 164 | APOL4 | apolipoprotein L, 4 |
| rs2076672 | 145 | APOL5 | apolipoprotein L, 5 |
| rs707922 | 155 | APOM | apolipoprotein M |
| rs2702285 | 9 | AVEN | apoptosis, caspase activation inhibitor |
| rs504714 | 114 | AVEN | apoptosis, caspase activation inhibitor |
| rs563895 | 181 | AVEN | apoptosis, caspase activation inhibitor |
| rs6265 | 309 | BDNF | brain-derived neurotrophic factor |
| rs2049045 | 316 | BDNF | brain-derived neurotrophic factor |
| rs908867 | 381 | BDNF | brain-derived neurotrophic factor |
| rs3761972 | 402 | CART | cocaine- and amphetamine-regulated transcript |
| rs10460960 | 210 | CCK | cholecystokinin |
| rs3822222 | 160 | CCKAR | cholecystokinin A receptor |
| rs1805002 | 384 | CCKBR | cholecystokinin B receptor |
| rs3760396 | 15 | CCL2 | chemokine (C-C motif) ligand 2 |
| rs1800775 | 483 | CETP | cholesteryl ester transfer protein, plasma |
| rs711752 | 19 | CETP | cholesteryl ester transfer protein, plasma |
| rs3764261 | 54 | CETP | cholesteryl ester transfer protein, plasma |
| rs5880 | 153 | CETP | cholesteryl ester transfer protein, plasma |
| rs1800776 | 178 | CETP | cholesteryl ester transfer protein, plasma |
| rs1532624 | 194 | CETP | cholesteryl ester transfer protein, plasma |
| rs5883 | 215 | CETP | cholesteryl ester transfer protein, plasma |
| rs1917813 | 403 | CHAT | choline acetyltransferase |
| rs3810947 | 37 | CHAT | choline acetyltransferase |
| rs8178990 | 69 | CHAT | choline acetyltransferase |
| rs885834 | 347 | CHAT | choline acetyltransferase |
| rs1064344 | 337 | CHKB | Choline Kinase Beta |
| rs2067477 | 192 | CHRM1 | cholinergic receptor, muscarinic 1 |
| rs324651 | 231 | CHRM2 | cholinergic receptor, muscarinic 2 |
| rs7520974 | 128 | CHRM3 | cholinergic receptor, muscarinic 3 |
| rs3087454 | 176 | CHRNA7 | cholinergic receptor, nicotinic, alpha polypeptide 7 |
| rs1355920 | 350 | CHRNA7 | cholinergic receptor, nicotinic, alpha polypeptide 7 |
| rs2221223 | 379 | CHRNA7 | cholinergic receptor, nicotinic, alpha polypeptide 7 |
| rs4680 | 92 | COMT | catechol-O-methyltransferase |
| rs2228502 | 64 | CPT1A | carnitine palmitoyltransferase 1A (liver) |
| rs597316 | 372 | CPT1A | carnitine palmitoyltransferase 1A |
| rs1799821 | 336 | CPT2 | carnitine palmitoyltransferase II |
| rs3176921 | 276 | CRH | corticotropin releasing hormone |
| rs4792887 | 52 | CRHR1 | corticotropin releasing hormone receptor 1 |
| rs1396862 | 236 | CRHR1 | corticotropin releasing hormone receptor 1 |
| rs2240403 | 16 | CRHR2 | corticotropin releasing hormone receptor 2 |
| rs107540 | 289 | CRHR2 | Corticotropin-releasing hormone receptor 2 |
| rs3093062 | 404 | CRP | C-reactive protein, pentraxin-related |
| rs2069525 | 405 | CYP1A2 | cytochrome P450, family 1, subfamily A, polypeptide 2 |
| rs2470890 | 108 | CYP1A2 | cytochrome P450, family 1, subfamily A, polypeptide 2 |
| rs762551 | 213 | CYP1A2 | cytochrome P450, family 1, subfamily A, polypeptide 2 |
| rs3758581 | 406 | CYP2C19 | cytochrome P450, family 2, subfamily C, polypeptide 19 |
| rs10509676 | 3 | CYP2C19 | cytochrome P450, family 2, subfamily C, polypeptide 19 |
| rs4986894 | 56 | CYP2C19 | cytochrome P450, family 2, subfamily C, polypeptide 19 |
| rs11188092 | 117 | CYP2C19 | cytochrome P450, family 2, subfamily C, polypeptide 19 |
| rs4986893 | 257 | CYP2C19 | cytochrome P450, family 2, subfamily C, polypeptide 19 |

TABLE 1-continued

| SNP | Seq. ID No. | Gene | Gene Description |
|---|---|---|---|
| rs4244285 | 305 | CYP2C19 | cytochrome P450, family 2, subfamily C, polypeptide 19 |
| rs1799853 | 14 | CYP2C9 | cytochrome P450, family 2, subfamily C, polypeptide 9 |
| rs1057910 | 359 | CYP2C9 | cytochrome P450, family 2, subfamily C, polypeptide 9 |
| CYP2D6_C2938T | 407 | CYP2D6 | cytochrome P450, family 2, subfamily D, polypeptide 6 |
| rs769258 | 408 | CYP2D6 | cytochrome P450, family 2, subfamily D, polypeptide 6 |
| rs1800716 | 409 | CYP2D6 | CYP2D6 cytochrome P450, family 2, subfamily D, polypeptide 6 |
| rs1058167 | 26 | CYP2D6 | cytochrome P450, family 2, subfamily D, polypeptide 6 |
| rs7286458 | 100 | CYP2D6 | cytochrome P450, family 2, subfamily D, polypeptide 6 |
| rs1135821 | 158 | CYP2D6 | cytochrome P450, family 2, subfamily D, polypeptide 6 |
| rs11568728 | 313 | CYP2D6 | cytochrome P450, family 2, subfamily D, polypeptide 6 |
| rs1058171 | 320 | CYP2D6 | cytochrome P450, family 2, subfamily D, polypeptide 6 |
| rs4987140 | 410 | CYP2D7P1 | cytochrome P450, family 2, subfamily D, polypeptide 7 pseudogene 1 (may be CYP2D6) |
| CYP3A4_4 | 411 | CYP3A4 | cytochrome P450, family 3, subfamily A, polypeptide 4 |
| rs2242480 | 28 | CYP3A4 | cytochrome P450, family 3, subfamily A, polypeptide 4 |
| rs2740574 | 99 | CYP3A4 | cytochrome P450, family 3, subfamily A, polypeptide 4 |
| rs12333983 | 109 | CYP3A4 | cytochrome P450, family 3, subfamily A, polypeptide 4 |
| rs4986910 | 239 | CYP3A4 | cytochrome P450, family 3, subfamily A, polypeptide 4 |
| rs1851426 | 304 | CYP3A4 | cytochrome P450, family 3, subfamily A, polypeptide 4 |
| CYP3A4_5 | 376 | CYP3A4 | cytochrome P450, family 3, subfamily A, polypeptide 4 |
| rs776746 | 34 | CYP3A5 | cytochrome P450, family 3, subfamily A, polypeptide 5 |
| rs4646450 | 184 | CYP3A5 | cytochrome P450, family 3, subfamily A, polypeptide 5 |
| rs15524 | 205 | CYP3A5 | cytochrome P450, family 3, subfamily A, polypeptide 5 |
| rs4646458 | 343 | CYP3A5 | cytochrome P450, family 3, subfamily A, polypeptide 5 |
| rs6976017 | 363 | CYP3A5 | cytochrome P450, family 3, subfamily A, polypeptide 5 |
| rs3808607 | 277 | CYP7A1 | cytochrome P450, family 7, subfamily A, polypeptide 1 |
| rs2070586 | 68 | DAO | D-amino-acid oxidase |
| rs1611115 | 13 | DBH | dopamine beta-hydroxylase (dopamine beta-monooxygenase) |
| rs4531 | 96 | DBH | dopamine beta-hydroxylase (dopamine beta-monooxygenase) |
| rs3779084 | 412 | DDC | dopa decarboxylase (aromatic L-amino acid decarboxylase |
| rs11575542 | 413 | DDC | dopa decarboxylase (aromatic L-amino acid decarboxylase) |
| rs1466163 | 78 | DDC | dopa decarboxylase (aromatic L-amino acid decarboxylase) |
| rs821616 | 149 | DISC1 | disrupted in schizophrenia 1 |
| rs1322783 | 319 | DISC1 | disrupted in schizophrenia 1 |
| rs1799914 | 217 | DRD1 | dopamine receptor D1 |
| rs2298122 | 17 | DRD1IP | dopamine receptor D1 interacting protein |
| rs2471857 | 188 | DRD2 | dopamine receptor D2 |
| rs1799978 | 342 | DRD2 | dopamine receptor D2 |
| rs1486008 | 414 | DRD3 | dopamine receptor D3 |
| rs9288993 | 103 | DRD3 | dopamine receptor D3 |
| rs167771 | 143 | DRD3 | dopamine receptor D3 |
| rs167770 | 208 | DRD3 | dopamine receptor D3 |
| rs4987059 | 272 | DRD4 | dopamine receptor D4 |
| rs2227847 | 415 | DRD5 | dopamine receptor D5 |
| rs2867383 | 209 | DRD5 | dopamine receptor D5 |
| rs2227852 | 233 | DRD5 | dopamine receptor D5 |
| rs1040410 | 10 | DTNBP1 | dystrobrevin binding protein 1 |
| rs2743867 | 74 | DTNBP1 | dystrobrevin binding protein 1 |
| rs1018381 | 261 | DTNBP1 | dystrobrevin binding protein 1 |
| rs5369 | 306 | EDN1 | endothelin 1 |
| rs5896 | 262 | F2 | coagulation factor II (thrombin) |
| rs2230849 | 416 | F2R | coagulation factor II (thrombin) receptor |
| rs1546503 | 417 | FABP2 | fatty acid binding protein 2, intestinal |
| rs2228305 | 418 | FASN | fatty acid synthase |
| rs2228309 | 41 | FASN | fatty acid synthase |
| rs1570679 | 419 | FLT1 | fms-related tyrosine kinase 1 (vascular endothelial growth factor/vascular permeability factor receptor) |
| rs2296189 | 95 | FLT1 | fms-related tyrosine kinase 1 (vascular endothelial growth factor/vascular permeability factor receptor) |
| rs748253 | 325 | FLT1 | fms-related tyrosine kinase 1 (vascular endothelial growth factor/vascular permeability factor receptor) |
| rs10507383 | 341 | FLT1 | fms-related tyrosine kinase 1 (vascular endothelial growth factor/vascular permeability factor receptor) |
| rs2119183 | 420 | GABRA2 | gamma-aminobutyric acid (GABA) A receptor, alpha 2 |
| rs1442061 | 168 | GABRA2 | gamma-aminobutyric acid (GABA) A receptor, alpha 2 |
| rs11503016 | 247 | GABRA2 | gamma-aminobutyric acid (GABA) A receptor, alpha 2 |
| rs3756007 | 339 | GABRA2 | gamma-aminobutyric acid (GABA) A receptor, alpha 2 |
| rs1398176 | 161 | GABRA4 | gamma-aminobutyric acid (GABA) A receptor, alpha 4 |
| rs3762611 | 189 | GABRA4 | gamma-aminobutyric acid (GABA) A receptor, alpha 4 |

TABLE 1-continued

| SNP | Seq. ID No. | Gene | Gene Description |
|---|---|---|---|
| rs2241165 | 421 | GAD1 | glutamate decarboxylase 1 (brain, 67 kDa) |
| rs3791850 | 179 | GAD1 | glutamate decarboxylase 1 (brain, 67 kDa) |
| rs701492 | 190 | GAD1 | glutamate decarboxylase 1 (brain, 67 kDa) |
| rs8190586 | 75 | GAD2 | glutamate decarboxylase 2 (pancreatic islets and brain, 65 kDa) |
| rs7072137 | 182 | GAD2 | glutamate decarboxylase 2 (pancreatic islets and brain, 65 kDa) |
| rs694066 | 345 | GAL | galanin |
| rs3761656 | 422 | GCG | glucagon |
| rs6173 | 423 | GH1 | growth hormone 1 |
| rs6032470 | 156 | GHRH | growth hormone releasing hormone |
| rs696217 | 424 | GHRL | ghrelin precursor |
| rs26312 | 327 | GHRL | ghrelin precursor |
| rs3790106 | 425 | GNAO1 | guanine nucleotide binding protein (G protein), alpha activating activity polypeptide O |
| rs11644870 | 426 | GNAO1 | guanine nucleotide binding protein (G protein), alpha activating activity polypeptide O |
| rs1190762 | 238 | GNAO1 | guanine nucleotide binding protein (G protein), alpha activating activity polypeptide O |
| rs4784642 | 250 | GNAO1 | guanine nucleotide binding protein (G protein), alpha activating activity polypeptide O |
| rs6489738 | 36 | GNB3 | guanine nucleotide binding protein (G protein), beta polypeptide 3 |
| rs1154597 | 427 | GSK3B | glycogen synthase kinase 3 beta |
| rs10934502 | 121 | GSK3B | glycogen synthase kinase 3 beta |
| rs4688046 | 169 | GSK3B | glycogen synthase kinase 3 beta |
| rs334555 | 212 | GSK3B | glycogen synthase kinase 3 beta |
| rs2287754 | 148 | GYS1 | glycogen synthase 1 (muscle) |
| rs5447 | 186 | GYS1 | glycogen synthase 1 (muscle) |
| rs2418003 | 428 | GYS2 | glycogen synthase 2 (liver) |
| rs10505873 | 11 | GYS2 | glycogen synthase 2 (liver) |
| rs1871143 | 268 | GYS2 | glycogen synthase 2 (liver) |
| rs1478290 | 355 | GYS2 | glycogen synthase 2 (liver) |
| rs2306179 | 360 | GYS2 | glycogen synthase 2 (liver) |
| rs2301108 | 122 | HIF1A | Fms-related tyrosine kinase 1 (vascular endothelial growth factor/vascular permeability factor receptor) |
| rs1951795 | 312 | HIF1A | hypoxia-inducible factor 1, alpha subunit (basic helix-loop-helix transcription factor) |
| rs3761740 | 77 | HMGCR | 3-hydroxy-3-methylglutaryl-Coenzyme A reductase |
| rs3846662 | 242 | HMGCR | 3-hydroxy-3-methylglutaryl-Coenzyme A reductase |
| rs3791244 | 429 | HNMT | histamine N-methyltransferase |
| rs12691940 | 318 | HNMT | histamine N-methyltransferase |
| rs1801105 | 330 | HNMT | histamine N-methyltransferase |
| rs2070937 | 326 | HP | haptoglobin |
| rs901865 | 214 | HRH1 | histamine receptor H1 |
| rs645574 | 430 | HRH2 | histamine receptor H2 |
| rs686874 | 270 | HRH2 | histamine receptor H2 |
| rs1614845 | 30 | HRH3 | histamine receptor H3 |
| rs7448024 | 431 | HTR1A | 5-hydroxytryptamine (serotonin) receptor 1A |
| rs676643 | 354 | HTR1D | 5-hydroxytryptamine (serotonin) receptor 1D |
| rs6312 | 317 | HTR2A | 5-hydroxytryptamine (serotonin) receptor 2A |
| rs6659734 | 344 | HTR2A | 5-hydroxytryptamine (serotonin) receptor 2A |
| rs539748 | 432 | HTR2C | 5-hydroxytryptamine (serotonin) receptor 2C |
| rs6318 | 433 | HTR2C | 5-hydroxytryptamine (serotonin) receptor 2C |
| rs1150226 | 260 | HTR3A | 5-hydroxytryptamine (serotonin) receptor 3A |
| rs1176744 | 60 | HTR3B | 5-hydroxytryptamine (serotonin) receptor 3B |
| rs2276307 | 79 | HTR3B | 5-hydroxytryptamine (serotonin) receptor 3B |
| rs3758987 | 293 | HTR3B | 5-hydroxytryptamine (serotonin) receptor 3B |
| rs1440451 | 171 | HTR5A | 5-hydroxytryptamine (serotonin) receptor 5A |
| rs1805054 | 434 | HTR6 | 5-hydroxytryptamine (serotonin) receptor 6 |
| rs9659997 | 303 | HTR6 | 5-hydroxytryptamine (serotonin) receptor 6 |
| rs1891311 | 175 | HTR7 | 5-hydroxytryptamine (serotonin) receptor 7 (adenylate cyclase-coupled) |
| rs1935349 | 367 | HTR7 | 5-hydroxytryptamine (serotonin) receptor 7 (adenylate cyclase-coupled) |
| rs5030388 | 435 | ICAM1 | intercellular adhesion molecule 1 (CD54), human rhinovirus receptor |
| rs1799969 | 436 | ICAM1 | intercellular adhesion molecule 1 (CD54), human rhinovirus receptor |
| rs1801714 | 152 | ICAM1 | intercellular adhesion molecule 1 (CD54), human rhinovirus receptor |
| rs5491 | 185 | ICAM1 | intercellular adhesion molecule 1 (CD54), human rhinovirus receptor |
| rs281432 | 255 | ICAM1 | intercellular adhesion molecule 1 (CD54), human rhinovirus receptor |

TABLE 1-continued

| SNP | Seq. ID No. | Gene | Gene Description |
|---|---|---|---|
| rs5030390 | 294 | ICAM1 | intercellular adhesion molecule 1 (CD54), human rhinovirus receptor |
| rs2033178 | 437 | IGF1 | insulin-like growth factor 1 (somatomedin C) |
| rs5742612 | 249 | IGF1 | insulin-like growth factor 1 (somatomedin C) |
| rs1800871 | 25 | IL10 | interleukin 10 |
| rs3024492 | 120 | IL10 | interleukin 10 |
| rs1800794 | 364 | IL1A | interleukin 1, alpha |
| rs1143634 | 97 | IL1B | interleukin 1, beta |
| rs3917287 | 438 | IL1R1 | interleukin 1 receptor type I |
| rs2192752 | 159 | IL1R1 | interleukin 1 receptor, type I |
| rs2228139 | 245 | IL1R1 | interleukin 1 receptor, type I |
| rs4833248 | 439 | IL2 | interleukin 2 |
| rs2069827 | 377 | IL6 | interleukin 6 (interferon, beta 2) |
| rs4247374 | 440 | INSR | insulin receptor |
| rs4804103 | 29 | INSR | insulin receptor |
| rs891087 | 57 | INSR | insulin receptor |
| rs7254060 | 237 | INSR | insulin receptor |
| rs10498210 | 441 | IRS1 | insulin receptor substrate 1 |
| rs1801123 | 126 | IRS1 | insulin receptor substrate 1 |
| rs4675096 | 285 | IRS1 | insulin receptor substrate-1 |
| rs1801278 | 298 | IRS1 | insulin receptor substrate 1 |
| rs2125489 | 5 | KDR | kinase insert domain receptor (a type III receptor tyrosine kinase) |
| rs2305948 | 300 | KDR | kinase insert domain receptor (a type III receptor tyrosine kinase) |
| rs5925 | 442 | LDLR | low density lipoprotein receptor (familial hypercholesterolemia) |
| rs8110695 | 44 | LDLR | low density lipoprotein receptor (familial hypercholesterolemia) |
| rs5927 | 264 | LDLR | low density lipoprotein receptor (familial hypercholesterolemia) |
| rs1433099 | 275 | LDLR | low density lipoprotein receptor (familial hypercholesterolemia) |
| rs1171276 | 6 | LEPR | leptin receptor |
| rs8179183 | 131 | LEPR | leptin receptor |
| rs7602 | 362 | LEPR | leptin receptor |
| rs3744485 | 443 | LGP1 | homolog of mouse LGP1 |
| rs1556478 | 45 | LIPA | lipase A, lysosomal acid, cholesterol esterase (Wolman disease) |
| rs6586179 | 130 | LIPA | lipase A, lysosomal acid, cholesterol esterase (Wolman disease) |
| rs6078 | 4 | LIPC | lipase, hepatic |
| rs936960 | 133 | LIPC | lipase, hepatic |
| rs417344 | 146 | LIPC | lipase, hepatic |
| rs1800588 | 219 | LIPC | lipase, hepatic |
| rs11632618 | 230 | LIPC | lipase, hepatic |
| rs6083 | 324 | LIPC | lipase, hepatic |
| rs1206034 | 444 | LIPE | lipase, hormone-sensitive |
| rs10422283 | 203 | LIPE | lipase, hormone-sensitive |
| rs814628 | 310 | LIPF | lipase, gastric |
| rs3819166 | 445 | LIPG | lipase, endothelial |
| rs4245232 | 20 | LIPG | lipase, endothelial |
| rs5950584 | 53 | LOC441514 | similar to apoptosis inhibitor 5; fibroblast growth factor 2-interacting factor 2; API5-like 1 |
| rs1561115 | 446 | LOC442077 | similar to Cofilin, non-muscle isoform OR retinoic acid receptor, beta (rs1561115 is about 200 kb away from RARB, within LOC442077) |
| rs264 | 35 | LPL | lipoprotein lipase |
| rs268 | 151 | LPL | lipoprotein lipase |
| rs295 | 331 | LPL | lipoprotein lipase |
| rs328 | 368 | LPL | lipoprotein lipase |
| rs7888450 | 447 | MAOB | monoamine oxidase B |
| rs1181252 | 70 | MAOB | monoamine oxidase B |
| rs3746619 | 448 | MC3R | melanocortin 3 receptor |
| rs6024725 | 127 | MC3R | melanocortin 3 receptor |
| rs1943220 | 449 | MC4R | melanocortin 4 receptor |
| rs2515507 | 450 | MCPH1 | microcephaly, primary autosomal recessive 1 |
| rs2515449 | 288 | MCPH1 | microcephaly, primary autosomal recessive 1 |
| rs1255 | 187 | MDH1 | malate dehydrogenase 1, NAD (soluble) |
| rs2278718 | 283 | MDH1 | malate dehydrogenase 1, NAD (soluble) |
| rs1800468 | 451 | MGC4093 | hypothetical protein MGC4093 |
| rs1982072 | 135 | MGC4093 | hypothetical protein MGC4093 |
| rs1800469 | 321 | MGC4093 | hypothetical protein MGC4093 |
| rs2066470 | 85 | MTHFR | 5,10-methylenetetrahydrofolate reductase (NADPH) |
| rs3816873 | 112 | MTP | microsomal triglyceride transfer protein (large polypeptide, 88 kDa) |

TABLE 1-continued

| SNP | Seq. ID No. | Gene | Gene Description |
|---|---|---|---|
| rs745075 | 269 | MTP | microsomal triglyceride transfer protein (large polypeptide, 88 kDa) |
| rs1800779 | 452 | NOS3 | nitric oxide synthase 3 (endothelial cell) |
| rs1549758 | 84 | NOS3 | nitric oxide synthase 3 (endothelial cell) |
| rs1799983 | 256 | NOS3 | nitric oxide synthase 3 (endothelial cell) |
| rs1800783 | 335 | NOS3 | nitric oxide synthase 3 (endothelial cell) |
| rs397081 | 453 | NOTCH4 | Notch homolog 4 (*Drosophila*) |
| rs204987 | 31 | NOTCH4 | Notch homolog 4 (*Drosophila*) |
| rs1468271 | 140 | NPY | neuropeptide Y |
| rs11100494 | 183 | NPY5R | neuropeptide Y receptor Y5 |
| rs6837793 | 243 | NPY5R | neuropeptide Y receptor Y5 |
| rs6195 | 454 | NR3C1 | nuclear receptor subfamily 3, group C, member 1 (glucocorticoid receptor) |
| rs190488 | 484 | NR3C1 | nuclear receptor subfamily 3, group C, member 1 (glucocorticoid receptor) |
| rs1438732 | 65 | NR3C1 | nuclear receptor subfamily 3, group C, member 1 (glucocorticoid receptor) |
| rs10515521 | 369 | NR3C1 | nuclear receptor subfamily 3, group C, member 1 (glucocorticoid receptor) |
| rs6196 | 373 | NR3C1 | nuclear receptor subfamily 3, group C, member 1 (glucocorticoid receptor) |
| rs2807071 | 163 | OAT | ornithine aminotransferase (gyrate atrophy) |
| rs2742115 | 218 | OLR1 | oxidised low density lipoprotein (lectin-like) receptor 1 |
| rs877172 | 278 | OXT | Oxytocin (Neurophysin 1) |
| rs8192708 | 98 | PCK1 | phosphoenolpyruvate carboxykinase 1 (soluble) |
| rs1131010 | 80 | PECAM1 | platelet/endothelial cell adhesion molecule (CD31 antigen) |
| rs4072032 | 138 | PECAM1 | platelet/endothelial cell adhesion molecule (CD31 antigen) |
| rs2838549 | 299 | PFKL | phosphofructokinase, liver |
| rs2269935 | 201 | PFKM | phosphofructokinase, muscle |
| rs11251694 | 455 | PFKP | phosphofructokinase, platelet |
| rs6901 | 89 | PFKP | phosphofructokinase, platelet |
| rs10508244 | 150 | PFKP | phosphofructokinase, platelet |
| rs1553921 | 456 | PIK3C2B | phosphoinositide-3-kinase, class 2, beta polypeptide |
| rs7556371 | 23 | PIK3C2B | phosphoinositide-3-kinase, class 2, beta polypeptide |
| rs1877394 | 50 | PIK3C2B | phosphoinositide-3-kinase, class 2, beta polypeptide |
| rs10494851 | 105 | PIK3C2B | phosphoinositide-3-kinase, class 2, beta polypeptide |
| rs2292459 | 204 | PIK3C2B | phosphoinositide-3-kinase, class 2, beta polypeptide |
| rs10494852 | 295 | PIK3C2B | phosphoinositide-3-kinase, class 2, beta polypeptide |
| rs11044082 | 12 | PIK3C2G | phosphoinositide-3-kinase, class 2, gamma polypeptide |
| rs11043982 | 39 | PIK3C2G | phosphoinositide-3-kinase, class 2, gamma polypeptide |
| rs12582982 | 235 | PIK3C2G | phosphoinositide-3-kinase, class 2, gamma polypeptide |
| rs10841044 | 252 | PIK3C2G | phosphoinositide-3-kinase, class 2, gamma polypeptide |
| rs3819162 | 457 | PIK3C3 | phosphoinositide-3-kinase, class 3 |
| rs7229485 | 48 | PIK3C3 | phosphoinositide-3-kinase, class 3 |
| rs4121817 | 71 | PIK3C3 | phosphoinositide-3-kinase, class 3 |
| rs3813065 | 338 | PIK3C3 | phosphoinositide-3-kinase, class 3 |
| rs10507145 | 458 | PIK3CA | phosphoinositide-3-kinase, catalytic, alpha polypeptide |
| rs7638323 | 459 | PIK3CA | phosphoinositide-3-kinase, catalytic, alpha polypeptide |
| rs2230461 | 58 | PIK3CA | phosphoinositide-3-kinase, catalytic, alpha polypeptide |
| rs1356413 | 144 | PIK3CA | phosphoinositide-3-kinase, catalytic, alpha polypeptide |
| rs7641983 | 165 | PIK3CA | phosphoinositide-3-kinase, catalytic, alpha polypeptide |
| rs870995 | 292 | PIK3CA | phosphoinositide-3-kinase, catalytic, alpha polypeptide |
| rs693293 | 460 | PIK3CB | phosphoinositide-3-kinase, catalytic, beta polypeptide |
| rs10513055 | 118 | PIK3CB | phosphoinositide-3-kinase, catalytic, beta polypeptide |
| rs1663554 | 225 | PIK3Cb | phosphoinositide-3-kinase, catalytic, beta polypeptide |
| rs6541017 | 246 | PIK3CD | phosphoinositide-3-kinase, catalytic, delta polypeptide |
| rs4727666 | 113 | PIK3CG | phosphoinositide-3-kinase, catalytic, gamma polypeptide |
| rs849404 | 198 | PIK3CG | phosphoinositide-3-kinase, catalytic, gamma polypeptide |
| rs706716 | 461 | PIK3R1 | phosphoinositide-3-kinase, regulatory subunit 1 (p85 alpha) |
| rs831125 | 462 | PIK3R1 | phosphoinositide-3-kinase, regulatory subunit 1 (p85 alpha) |
| rs10515070 | 125 | PIK3R1 | phosphoinositide-3-kinase, regulatory subunit 1 (p85 alpha) |
| rs706713 | 221 | PIK3R1 | phosphoinositide-3-kinase, regulatory subunit 1 (p85 alpha) |
| rs40318 | 357 | PIK3R1 | phosphoinositide-3-kinase, regulatory subunit 1 (p85 alpha) |
| rs3762272 | 59 | PKLR | pyruvate kinase, liver and RBC |
| rs1037680 | 463 | PKM2 | pyruvate kinase, muscle |
| rs2856929 | 142 | PKM2 | pyruvate kinase, muscle |

TABLE 1-continued

| SNP | Seq. ID No. | Gene | Gene Description |
|---|---|---|---|
| rs3769671 | 273 | POMC | proopiomelanocortin (adrenocorticotropin/beta-lipotropin/alpha-melanocyte stimulating hormone/beta-melanocyte stimulating hormone/beta-endorphin) |
| rs662 | 110 | PON1 | paraoxonase 1 |
| rs854572 | 172 | PON1 | paraoxonase 1 |
| rs3917550 | 173 | PON1 | paraoxonase 1 |
| rs705381 | 206 | PON1 | paraoxonase 1 |
| rs4253623 | 464 | PPARA | peroxisome proliferative activated receptor, alpha |
| rs4253655 | 465 | PPARA | peroxisome proliferative activated receptor, alpha |
| rs2229245 | 466 | PPARA | peroxisome proliferative activated receptor, alpha |
| rs5766741 | 21 | PPARA | peroxisome proliferative activated receptor, alpha |
| rs1800206 | 281 | PPARA | peroxisome proliferative activated receptor, alpha |
| rs1801282 | 87 | PPARG | peroxisome proliferative activated receptor, gamma |
| rs4135268 | 134 | PPARG | peroxisome proliferative activated receptor, gamma |
| rs6809631 | 220 | PPARG | peroxisome proliferative activated receptor, gamma |
| rs3792822 | 82 | PRKAA1 | protein kinase, AMP-activated, alpha 1 catalytic subunit |
| rs461404 | 287 | PRKAA1 | protein kinase, AMP-activated, alpha 1 catalytic subunit |
| rs2796516 | 349 | PRKAA2 | protein kinase, AMP-activated, alpha 2 catalytic subunit |
| rs1062688 | 263 | PRKAB1 | protein kinase, AMP-activated, beta 1 non-catalytic subunit |
| rs2883434 | 467 | PRKAB2 | protein kinase, AMP-activated, beta 2 non-catalytic subunit |
| rs7975791 | 468 | PRKAG1 | protein kinase, AMP-activated, gamma 1 non-catalytic subunit |
| rs2293445 | 61 | PRKAG1 | protein kinase, AMP-activated, gamma 1 non-catalytic subunit |
| rs1029947 | 107 | PRKAG2 | protein kinase, AMP-activated, gamma 2 non-catalytic subunit |
| rs6960931 | 199 | PRKAG2 | protein kinase, AMP-activated, gamma 2 non-catalytic subunit |
| rs4726107 | 271 | PRKAG2 | protein kinase, AMP-activated, gamma 2 non-catalytic subunit |
| rs1860743 | 334 | PRKAG2 | protein kinase, AMP-activated, gamma 2 non-catalytic subunit |
| rs231460 | 115 | PYY | peptide YY |
| rs1058046 | 380 | PYY | peptide YY |
| rs4890109 | 136 | RARA | retinoic acid receptor, alpha |
| rs9904270 | 253 | RARA | retinoic acid receptor, alpha |
| rs2033447 | 72 | RARB | retinoic acid receptor, beta |
| rs1290443 | 279 | RARB | retinoic acid receptor, beta |
| rs322695 | 291 | RARB | retinoic acid receptor, beta |
| rs10082776 | 370 | RARG | retinoic acid receptor, gamma |
| rs3219177 | 346 | RETN | resistin |
| rs3118536 | 196 | RXRA | retinoid X receptor, alpha |
| rs3750546 | 202 | RXRA | retinoid X receptor, alpha |
| rs4917348 | 322 | RXRA | retinoid X receptor, alpha |
| rs10800098 | 469 | RXRG | retinoid X receptor, gamma |
| rs157864 | 383 | RXRG | retinoid X receptor, gamma |
| rs6488950 | 470 | SCARB1 | scavenger receptor class B, member 1 |
| rs4765623 | 81 | SCARB1 | scavenger receptor class B, member 1 |
| rs10846744 | 154 | SCARB1 | scavenger receptor class B, member 1 |
| rs3853188 | 24 | SCARB2 | scavenger receptor class B, member 2 |
| rs894251 | 251 | SCARB2 | scavenger receptor class B, member 2 |
| rs5361 | 116 | SELE | selectin E (endothelial adhesion molecule 1) |
| rs5368 | 348 | SELE | selectin E (endothelial adhesion molecule 1) |
| rs6136 | 2 | SELP | selectin P (granule membrane protein 140 kDa, antigen CD62) |
| rs6131 | 93 | SELP | selectin P (granule membrane protein 140 kDa, antigen CD62) |
| rs1800808 | 193 | SELP | selectin P (granule membrane protein 140 kDa, antigen CD62) |
| rs6092 | 375 | SERPINE1 | serine (or cysteine) proteinase inhibitor, clade E (nexin, plasminogen activator inhibitor type 1), member 1 |
| rs7200210 | 157 | SLC12A4 | solute carrier family 12 (potassium/chloride transporters), member 4 |
| rs1547387 | 223 | SLC39A7 | solute carrier family 39 (zinc transporter), member 7 |
| rs10521578 | 471 | SLC6A14 | solute carrier family 6 (neurotransmitter transporter), member 14 |
| rs2042449 | 472 | SLC6A3 | solute carrier family 6 (neurotransmitter transporter, dopamine), member 3 |
| rs3756450 | 8 | SLC6A3 | solute carrier family 6 (neurotransmitter transporter, dopamine), member 3 |
| rs140700 | 43 | SLC6A4 | solute carrier family 6 (neurotransmitter transporter, serotonin), member 4 |

TABLE 1-continued

| SNP | Seq. ID No. | Gene | Gene Description |
|---|---|---|---|
| rs2020933 | 88 | SLC6A4 | solute carrier family 6 (neurotransmitter transporter, serotonin), member 4 |
| rs2306283 | 473 | SLCO1B1 | solute carrier organic anion transporter family, member 1B1 |
| rs4149056 | 38 | SLCO1B1 | solute carrier organic anion transporter family, member 1B1 |
| rs2070424 | 267 | SOD1 | superoxide dismutase 1, soluble (amyotrophic lateral sclerosis 1 (adult)) |
| rs4925119 | 474 | SREBF1 | sterol regulatory element binding transcription factor |
| rs2162189 | 216 | SST | somatostatin |
| rs2071710 | 280 | SSTR3 | somatostatin receptor 3 |
| rs619698 | 167 | SSTR5 | somatostatin receptor 5 |
| rs7211875 | 42 | TADA2L | transcriptional adaptor 2 (ADA2 homolog, yeast)-like |
| rs1053651 | 475 | TCAP | titin-cap (telethonin) |
| rs931992 | 141 | TCAP | titin-cap (telethonin) |
| rs600728 | 104 | TEK | TEK tyrosine kinase, endothelial (venous malformations, multiple cutaneous and mucosal) |
| rs617333 | 211 | TEK | TEK tyrosine kinase, endothelial (venous malformations, multiple cutaneous and mucosal) |
| rs1800471 | 27 | TGFB1 | transforming growth factor, beta 1 (Camurati-Engelmann disease) |
| rs6578993 | 18 | TH | Tyrosine hydroxylase |
| rs3842726 | 170 | TH | tyrosine hydroxylase |
| rs1800630 | 476 | TNF | tumor necrosis factor (TNF superfamily, member 2) |
| rs3755480 | 477 | TNFAIP6 | tumor necrosis factor, alpha-induced protein 6 |
| rs3771892 | 301 | TNFAIP6 | tumor necrosis factor, alpha-induced protein 6 |
| rs1046668 | 323 | TNFAIP6 | tumor necrosis factor, alpha-induced protein 6 |
| rs4149578 | 147 | TNFRSF1A | tumor necrosis factor receptor superfamily, member 1A |
| rs590368 | 478 | TNFRSF1B | tumor necrosis factor receptor superfamily, member 1B |
| rs235249 | 47 | TNFRSF1B | tumor necrosis factor receptor superfamily, member 1B |
| rs1061622 | 340 | TNFRSF1B | tumor necrosis factor receptor superfamily, member 1B |
| rs6700734 | 378 | TNFSF6 | tumor necrosis factor (ligand) superfamily, member 6 |
| rs737865 | 284 | TXNRD2 | thioredoxin reductase 2 |
| rs660339 | 229 | UCP2 | uncoupling protein 2 (mitochondrial, proton carrier) |
| rs2229707 | 479 | UCP3 | uncoupling protein 3 (mitochondrial proton carrier) |
| rs826082 | 174 | UCP3 | uncoupling protein 3 (mitochondrial, proton carrier) |
| rs2734830 | 228 | UCP3 | uncoupling protein 3 (mitochondrial, proton carrier) |
| rs3783613 | 480 | VCAM1 | vascular cell adhesion molecule 1 |
| rs1041163 | 258 | VCAM1 | vascular cell adhesion molecule 1 |
| rs833060 | 358 | VEGF | vascular endothelial growth factor |
| rs6967107 | 166 | WBSCR14 | Williams Beuren syndrome chromosome region 14 |

The SNPs and genes in Table 1 are provided in the nomenclature adopted by the National Center for Biotechnology Information (NCBI) of the National Institute of Health. The sequence data for the SNPs and genes listed in Table 1 is known in the art and is readily available from the NCBI dbSNP and OMIM databases. Each of the above-identified SNPs, or combinations thereof, corresponds to a particular embodiment of the invention.

Each of the foregoing genes, and combinations thereof, are expected to provide useful markers in the practice of the invention. The gene array includes all of the novel marker genes, or a subset of the genes, or unique nucleic acid portions of these genes. The gene array of the invention is useful in discovering new genetic markers of metabolic syndromes in response to psychotropic drugs.

The specific marker will be selected from variants of these genes, or other genes determined to be associated with metabolic syndromes in response to psychotropic drugs. Preferred variants in accordance with the invention are single nucleotide polymorphisms (SNPs) which refers to a gene variant differing in the identity of one nucleotide pair from the normal gene.

One embodiment of the present invention involves obtaining nucleic acid, e.g. DNA, from a blood sample of a subject, and assaying the DNA to determine the individuals' genotype of one or a combination of the marker genes associated with metabolism. Other sampling procedures include but are not limited to buccal swabs, saliva, or hair root. In a preferred embodiment, genotyping is performed using a gene array methodology, which can be readily and reliably employed in the screening and evaluation methods according to this invention. A number of gene arrays are commercially available for use by the practitioner, including, but not limited to, static (e.g. photolithographically set), suspended beads (e.g. soluble arrays), and self assembling bead arrays (e.g. matrix ordered and deconvoluted). More specifically, the nucleic acid array analysis allows the establishment of a pattern of genetic variability from multiple genes and facilitates an understanding of the complex interactions that are elicited in progression to DIMS.

Diabetes and Metabolic Syndromes (DIMS) represent disease states with the following diagnostic components: increased waist circumference, elevated glucose level, decreased high density lipoprotein cholesterol (HDLc) level, elevated Triglyceride level, and increased blood pressure. As a consequence, those components should exhibit significant correlations, and part of their variation will be explainable as correlates of a more fundamental variable that is not directly observed. However, as is often done in statistics, such an underlying variable can be inferred from the correlation amongst its correlates. We will use principal component analysis to infer such a variable, which we term the metabolic syndromes index (MSI).

There are three important expected advantages to using the MSI to search for genetic associations related to the metabolic syndromes. First, since the MSI represents a more fundamental variable than its correlates, it may be closer in the causal chain to its genetic determinants, and thus any true association will be stronger and less obscured by random effects. Second, since the MSI is determined by measuring multiple correlates, random measurement errors will partially cancel and the index can be determined with less error than any one of its correlates. Third, by using a continuous variable, differences in the degree of affectedness can be exploited, which in a categorical model would be lost completely. All three of these advantages result in higher sensitivity for detecting genetic associations, providing the motivation for establishing the MSI.

An additional advantage of an MSI determined from data is that it removes the arbitrariness that is associated with clinical thresholds. The coefficients of the MSI are determined from the data, and no thresholds are needed, since the index is used as a continuous variable.

The index will be composed of components of DIMS: Waist circumference, glucose level, high density lipoprotein cholesterol (HDLc) level, Triglyceride level, and blood pressure. Blood pressure will be divided into two components, diastolic and systolic. Thus, the index is defined as:

$$MSI = \sum_i \beta_i m_i = \beta_0 \frac{WC - \overline{WC}}{\text{Var}(WC)} + \beta_1 \frac{GLU - \overline{GLU}}{\text{Var}(GLU)} +$$
$$\beta_2 \frac{HDL - \overline{HDL}}{\text{Var}(HDL)} + \beta_3 \frac{TG - \overline{TG}}{\text{Var}(TG)} + \beta_4 \frac{BPD - \overline{BPD}}{\text{Var}(BPD)} + \beta_5 \frac{BPS - \overline{BPS}}{\text{Var}(BPS)}$$

The $m_i$ are the measurements normalized to have a zero average and a variance of 1. The coefficients $\beta_i$ will be derived from data available from a representative population. Below, we propose two different ways of deriving the coefficients: 1) By principal component analysis ($MSI_{pc}$), and 2) by classification optimization ($MSI_{cl}$).

The use of principal component analysis makes the index independent of any given clinical definition of the syndrome. We will not enter here into the mathematical details of principal component analysis, which is well known by one skilled in the art, except to say that the coefficients under this definition are given by the coefficients of the eigenvector for the most significant principal component in the six-dimensional space of measurements including waist circumference (WC), blood glucose (GLU), HDL cholesterol level (HDL), triglyceride level (TG), diastolic Blood Pressure (BPD), and systolic Blood Pressure (BPS). If metabolic syndromes exist as a combined disease entity, there must be significant covariance among the characteristics of the syndromes, and $MSI_{pc}$ defined as the first principal component is the most natural way to quantify the degree of progression towards the combined disease entity. The correspondence between this index and the clinical definition will indicate to what extent the data supports the usefulness of the clinical definition.

As an alternative, we define the index $MSI_{cl}$ in terms of the clinical thresholds, to obtain a better correspondence of the index to accepted clinical practice. In this case, the coefficients are given by the average difference in each measurement between the patient and a clinical threshold:

$\beta_i = \overline{m}^+_i - \overline{m}^-_i$.

Essentially, this means that measurements that differ strongly from clinical thresholds have more weight in the index than those that differ less.

If the threshold-based definition of the syndromes is well supported by the data, the two parameterizations of the index given above should be very similar, and it would not make much difference which one was used for statistical analysis. If the indices turn out to be very different, a choice needs to be made as to whether the structure of the data or the threshold-based values should dictate the index. In this application, we will omit the subscript and refer to the index only as the MSI, recognizing that the specific choice can only be made after some significant data analysis.

We have undertaken a preliminary analysis of data of 100 patients treated with psychotropics for which all the needed measurements were available. A principal component analysis was performed, and the results are very encouraging. The loadings of the first principal component, which would be used for the coefficients $\beta_i$, are 0.6, 0.3, −0.4, 0.4, 0.4 respectively for the variables WC, GLU, HDL, TG, and BPD. Note that all variables are loaded almost equally, indicating that each one is important to define the MSI. Waist circumference is the most important, with a loading of 0.6, and glucose the least, with 0.3. Note in particular, that the signs of the coefficients correctly indicate the nature of the components as risk factors, i.e. high values of HDL are good, while low values are good for all others. This would not be expected if there was not in fact an underlying variable accounting for the metabolic syndromes. As should be expected, the MSI is not the only determinant of its correlates, in the preliminary data set it accounts for 33% of their variation.

Example 1

Physiogenomics was used to explore the variability in patient metabolic syndromes in response to psychotropic drugs. Physiogenomics is a medical application of sensitivity analysis [Ruano G. HT. Physiogenomics: Integrating systems engineering and nanotechnology for personalized health. In: J. B., ed. The Biomedical Engineering Handbook, 2006]. Sensitivity analysis is the study of the relationship between the input and the output of a model and the analysis, utilizing systems theory, of how variation of the input leads to changes in output quantities. Physiogenomics utilizes as input the variability in genes, measured by single nucleotide polymorphisms (SNP) and determines how the SNP frequency among individuals relates to the variability in physiological characteristics, the output.

The goal of the investigation was to develop physiogenomic markers for psychotropic-induced DIMS by using an informatics platform to analyze data.

Potential Associations of Marker Genes to Metabolic Syndromes in Response to Psychotropic Drugs.

Various SNPs associated with, for example, the observation of various parameters of metabolic syndromes in patients on psychotropic drugs were screened. The endpoints analyzed were the blood levels of LDL, HDL, and glucose; blood pressure; body mass index; waist circumference; and metabolic syndromes index. The physiogenomic model was developed using the following procedure: 1) Establish a covariate model using only the demographic and clinical variables, 2) Screen for associated genetic markers by testing each SNP against the unexplained residual of the covariate model, and 3) Establish a revised model incorporating the significant associations from the SNP screen. All models are simple linear regression models, but other well-known statistical methods are contemplated to be useful.

Tables 2-7 list the SNPs that have been found to be associated with each outcome for each drug. Only SNPs with a statistical significance level of 0.05 or more are shown. The physiotypes are generated from the SNPs in this table by the step-wise procedure, as described generally in U.S. patent application Ser. No. 11/010,716. The coefficients are for the single SNPs and explain the residual change in the indicated response after covariates.

TABLE 2

| SNP | Gene | p | Coeff. | Allele |
|---|---|---|---|---|
| \multicolumn{5}{c}{Arapiprazole} | | | | |
| \multicolumn{5}{c}{Total Cholesterol} | | | | |
| rs1057910 | CYP2C9 | 5.52E-03 | 21.01018 | AC |
| rs2288911 | APOC4 | 8.64E-03 | 17.40741 | AC |
| rs701492 | GAD1 | 1.17E-02 | -27.4074 | TC |
| rs9904270 | RARA | 1.32E-02 | -29.5172 | TC |
| rs7412 | APOE | 1.44E-02 | -25.0618 | TC |
| rs2301108 | HIF1A | 1.75E-02 | 25.47619 | AG |
| rs3760396 | CCL2 | 1.90E-02 | -17.2171 | GC |
| rs3024492 | IL10 | 3.21E-02 | 15.9548 | TA |
| rs6809631 | PPARG | 3.34E-02 | 14.48819 | AT |
| rs2229416 | ACACA | 3.68E-02 | -23.9821 | AG |
| rs4795180 | ACACA | 3.68E-02 | -23.9821 | TG |
| rs6901 | PFKP | 4.05E-02 | -14.443 | AG |
| rs7254060 | INSR | 4.61E-02 | -27.6129 | AG |
| rs1801282 | PPARG | 4.74E-02 | 17.74663 | CG |
| rs2807071 | OAT | 4.77E-02 | -17.5158 | TC |
| \multicolumn{5}{c}{LDL Cholesterol} | | | | |
| rs701492 | GAD1 | 1.25E-04 | -41.2222 | TC |
| rs1057910 | CYP2C9 | 9.03E-04 | 25.74949 | AC |
| rs9904270 | RARA | 2.39E-03 | -37.1182 | TC |
| rs264 | LPL | 3.00E-03 | -26.5842 | AG |
| rs231460 | PYY | 7.02E-03 | -22.8702 | TC |
| rs3822222 | CCKAR | 8.57E-03 | 24.98271 | TC |
| rs5030390 | ICAM1 | 1.30E-02 | -27.8333 | AG |
| rs2227852 | DRD5 | 1.36E-02 | -28.1852 | AG |
| rs2229416 | ACACA | 1.41E-02 | -29.2143 | AG |
| rs4795180 | ACACA | 1.41E-02 | -29.2143 | TG |
| rs7412 | APOE | 1.42E-02 | -26.3527 | TC |
| rs3762611 | GABRA4 | 1.49E-02 | -18.7032 | AG |
| rs10509676 | CYP2C19 | 1.50E-02 | -24.25 | TA |
| rs140700 | SLC6A4 | 1.76E-02 | 34.05806 | AG |
| rs2306179 | GYS2 | 2.72E-02 | -15.1786 | AG |
| rs1176744 | HTR3B | 2.77E-02 | -14.3889 | TG |
| rs2192752 | IL1R1 | 3.35E-02 | 19.87871 | AC |
| rs2070937 | HP | 3.68E-02 | 16.59223 | AG |
| rs1805002 | CCKBR | 3.93E-02 | -32.875 | AG |
| rs1871143 | GYS2 | 4.09E-02 | -14.1588 | TG |
| rs3760396 | CCL2 | 4.10E-02 | -15.8942 | GC |
| rs7816340 | ADRA1A | 4.36E-02 | -25.5911 | TC |
| \multicolumn{5}{c}{HDL Cholesterol} | | | | |
| rs701492 | GAD1 | 3.93E-04 | 19.50313 | TC |
| rs3792822 | PRKAA1 | 7.66E-04 | 18.67578 | AG |
| rs264 | LPL | 1.65E-03 | 14.10559 | AG |
| rs3771892 | TNFAIP6 | 2.83E-03 | 15.48269 | AG |
| rs1046668 | TNFAIP6 | 2.83E-03 | 15.48269 | AG |
| rs4726107 | LOC441301 | 3.12E-03 | 44.03077 | TC |
| rs2229126 | ADRA1A | 3.12E-03 | 44.03077 | AT |
| rs295 | LPL | 4.68E-03 | 10.56046 | AC |
| rs3087454 | CHRNA7 | 9.43E-03 | 9.670192 | TG |
| rs662 | PON1 | 9.95E-03 | -9.39013 | AG |
| rs10515521 | NR3C1 | 1.25E-02 | 12.30222 | AG |
| rs6809631 | PPARG | 1.29E-02 | -8.85674 | AT |
| rs833060 | VEGF | 2.73E-02 | 8.908791 | TG |
| rs8192708 | PCK1 | 3.21E-02 | -10.1036 | AG |
| rs5880 | CETP | 3.27E-02 | -13.6129 | CG |
| rs814628 | LIPF | 3.28E-02 | -10.4082 | AG |
| rs3853188 | SCARB2 | 4.11E-02 | 18.6993 | AC |
| rs3761422 | ADORA2A | 4.49E-02 | 8.082692 | TC |
| rs6578993 | TH | 4.54E-02 | -10.0126 | TC |
| rs6837793 | NPY5R | 4.64E-02 | 12.05896 | AG |
| rs5742612 | IGF1 | 4.71E-02 | 31.35967 | TC |
| rs1800588 | LIPC | 4.98E-02 | 7.715313 | TC |

TABLE 2-continued

| SNP | Gene | p | Coeff. | Allele |
|---|---|---|---|---|
| \multicolumn{5}{c}{Arapiprazole} | | | | |
| \multicolumn{5}{c}{Triglycerides (TG) as log(TG)} | | | | |
| rs3024492 | IL10 | 1.09E-03 | 0.345095 | TA |
| rs2288911 | APOC4 | 2.38E-03 | 0.293592 | AC |
| rs814628 | LIPF | 6.26E-03 | 0.365599 | AG |
| rs1190762 | GNAO1 | 1.01E-02 | 0.480881 | AC |
| rs617333 | TEK | 1.17E-02 | 0.273345 | TG |
| rs1860743 | PRKAG2 | 1.18E-02 | 0.422607 | AG |
| rs2301108 | HIF1A | 1.22E-02 | 0.396613 | AG |
| rs573542 | ADRA1A | 1.34E-02 | 0.463675 | AG |
| rs1556478 | LIPA | 2.12E-02 | 0.242956 | AG |
| rs3816873 | MTP | 2.14E-02 | -0.25274 | TC |
| rs3769671 | POMC | 2.47E-02 | -0.69063 | AC |
| rs6809631 | PPARG | 2.68E-02 | 0.223025 | AT |
| rs686874 | HRH2 | 3.23E-02 | -0.38512 | TC |
| rs1801282 | PPARG | 3.38E-02 | 0.280476 | CG |
| rs7072137 | GAD2 | 3.72E-02 | 0.426593 | AG |
| rs1478290 | GYS2 | 3.94E-02 | -0.22446 | TG |
| rs1003854 | AIRE | 4.13E-02 | 0.264724 | TC |
| rs1061622 | TNFRSF1B | 4.57E-02 | 0.219945 | TG |
| rs2867383 | DRD5 | 4.62E-02 | 0.297196 | AG |
| rs4149578 | TNFRSF1A | 4.85E-02 | -0.35403 | A |
| \multicolumn{5}{c}{Ratio of Total Cholesterol to HDL Cholesterol} | | | | |
| rs701492 | GAD1 | 7.64E-04 | -1.53583 | TC |
| rs6809631 | PPARG | 1.88E-03 | 0.888149 | AT |
| rs3792822 | PRKAA1 | 7.46E-03 | -1.25793 | AG |
| rs3024492 | IL10 | 1.07E-02 | 0.815272 | TA |
| rs814628 | LIPF | 1.16E-02 | 0.998605 | AG |
| rs1860743 | PRKAG2 | 1.22E-02 | 1.235653 | AG |
| rs5880 | CETP | 1.72E-02 | 1.238749 | CG |
| rs3771892 | TNFAIP6 | 1.80E-02 | -1.03332 | AG |
| rs1046668 | TNFAIP6 | 1.80E-02 | -1.03332 | AG |
| rs295 | LPL | 2.00E-02 | -0.72745 | AC |
| rs1801282 | PPARG | 2.29E-02 | 0.878125 | CG |
| rs3761422 | ADORA2A | 3.10E-02 | -0.71149 | TC |
| rs1805002 | CCKBR | 3.30E-02 | -1.40739 | AG |
| rs3847063 | ACHE | 3.39E-02 | 0.590641 | AG |
| rs3176921 | CRH | 3.55E-02 | -0.75617 | TC |
| rs1478290 | GYS2 | 3.68E-02 | -0.66715 | TG |
| rs2228502 | CPT1A | 3.70E-02 | 0.906795 | TC |
| rs264 | LPL | 3.74E-02 | -0.79885 | AG |
| rs10422283 | LIPE | 4.11E-02 | -0.66398 | TC |
| rs328 | LPL | 4.17E-02 | -1.01936 | CG |
| rs3087454 | CHRNA7 | 4.62E-02 | -0.62305 | TG |
| \multicolumn{5}{c}{Blood Glucose Level} | | | | |
| rs11043982 | PIK3C2G | 3.64E-03 | 26.44874 | TC |
| rs4245232 | LIPG | 9.48E-03 | 12.90855 | AC |
| rs132642 | APOL3 | 1.17E-02 | 13.30331 | TA |
| rs2066470 | MTHFR | 1.40E-02 | -12.036 | TC |
| rs5742612 | IGF1 | 1.44E-02 | 35.7961 | TC |
| rs1283694 | ANGPT1 | 1.57E-02 | -12.7982 | TA |
| rs1877394 | PIK3C2B | 2.51E-02 | 34.62821 | AG |
| rs1356413 | PIK3CA | 2.57E-02 | 24.76868 | GC |
| rs1800206 | PPARA | 2.60E-02 | 24.72177 | GC |
| rs136163 | APOL1 | 2.73E-02 | -7.79245 | TG |
| rs4784642 | GNAO1 | 2.95E-02 | -8.59139 | AG |
| rs659734 | HTR2A | 3.10E-02 | 24.00379 | TC |
| rs2838549 | PFKL | 3.60E-02 | 10.89693 | AG |
| rs132653 | APOL3 | 4.16E-02 | 9.717615 | AC |
| rs4680 | COMT | 4.54E-02 | -7.18481 | AG |
| \multicolumn{5}{c}{Systolic Blood Pressure} | | | | |
| rs6265 | BDNF | 2.43E-03 | -9.8498 | AG |
| rs4531 | DBH | 5.09E-03 | 12.91313 | TG |
| rs2015353 | ADORA2B | 5.75E-03 | 6.899435 | AG |
| rs3766560 | ADORA1 | 8.87E-03 | -9.43017 | AG |
| rs2049045 | BDNF | 1.13E-02 | -8.39643 | CG |
| rs10507383 | FLT1 | 1.59E-02 | -11.1959 | CG |
| rs2429511 | ADRB1 | 3.02E-02 | 5.347768 | AG |
| rs2125489 | KDR | 3.13E-02 | 9.599798 | TC |
| rs854572 | PON1 | 3.24E-02 | -5.33742 | CG |
| rs2296189 | FLT1 | 3.31E-02 | -7.18664 | AG |
| rs4245232 | LIPG | 3.38E-02 | 7.779792 | AC |
| rs2229416 | ACACA | 3.68E-02 | 9.327316 | AG |

TABLE 2-continued

Arapiprazole

| SNP | Gene | p | Coeff. | Allele |
|---|---|---|---|---|
| rs4795180 | ACACA | 3.68E-02 | 9.327316 | TG |
| rs619698 | SSTR5 | 3.99E-02 | -6.7945 | AC |
| rs3853188 | SCARB2 | 4.21E-02 | 13.68281 | AC |
| rs1143634 | IL1B | 4.56E-02 | -6.22023 | TC |
| rs903361 | ADORA1 | 4.86E-02 | 4.57586 | TC |
| Diastolic Blood Pressure | | | | |
| rs11632618 | LIPC | 2.00E-03 | -8.28661 | AG |
| rs2069827 | IL6 | 2.70E-03 | 6.938182 | TG |
| rs1040410 | DTNBP1 | 5.13E-03 | -6.85991 | TC |
| rs10890819 | ACAT1 | 5.38E-03 | -4.97902 | TC |
| rs849404 | PIK3CG | 6.54E-03 | 7.405284 | AG |
| rs1799983 | NOS3 | 1.22E-02 | -3.93607 | TG |
| rs5030390 | ICAM1 | 1.25E-02 | 6.155844 | AG |
| rs722341 | ABCC8 | 1.25E-02 | 6.155844 | TC |
| rs2743867 | DTNBP1 | 1.34E-02 | -4.92178 | AG |
| rs1018381 | DTNBP1 | 1.34E-02 | -4.92178 | TC |
| rs11212515 | ACAT1 | 1.38E-02 | -4.46408 | AT |
| rs3766560 | ADORA1 | 1.76E-02 | -5.11939 | AG |
| rs936960 | LIPC | 3.07E-02 | -5.71266 | AC |
| rs231460 | PYY | 3.09E-02 | 3.951049 | TC |
| rs1799821 | CPT2 | 3.53E-02 | -3.77794 | AG |
| rs3853188 | SCARB2 | 3.56E-02 | 8.374656 | AC |
| rs12333983 | CYP3A4 | 3.95E-02 | -5.24355 | TA |
| rs748253 | FLT1 | 3.95E-02 | 3.107199 | TG |
| rs877172 | OXT | 4.22E-02 | -3.20229 | AC |
| rs6083 | LIPC | 4.46E-02 | -3.46584 | AG |
| rs10515521 | NR3C1 | 4.80E-02 | 4.317634 | AG |
| rs833060 | VEGF | 4.98E-02 | -3.47836 | TG |
| Body Mass | | | | |
| rs3846662 | HMGCR | 1.10E-02 | 14.91658 | TC |
| rs2070586 | DAO | 1.13E-02 | 23.50948 | AG |
| rs1396862 | CRHR1 | 1.16E-02 | 25.928 | TC |
| rs903361 | ADORA1 | 1.62E-02 | 13.92594 | TC |
| rs854572 | PON1 | 2.10E-02 | -14.3289 | CG |
| rs676210 | APOB | 2.41E-02 | 17.63523 | AG |
| rs11632618 | LIPC | 2.62E-02 | -26.0821 | AG |
| rs833060 | VEGF | 2.99E-02 | -16.1994 | TG |
| rs3764261 | CETP | 3.18E-02 | 14.75122 | TG |
| rs711752 | CETP | 3.38E-02 | 15.70343 | AG |
| rs4727666 | PIK3CG | 3.40E-02 | -18.0157 | AG |
| rs4680 | COMT | 3.62E-02 | -13.6555 | AG |
| rs7816340 | ADRA1A | 3.64E-02 | 24.65 | TC |
| rs4994 | ADRB3 | 3.93E-02 | 15.00642 | TC |
| rs1611115 | DBH | 4.21E-02 | 17.71905 | TC |
| rs231460 | PYY | 4.32E-02 | 18.41415 | TC |
| rs7254060 | INSR | 4.42E-02 | 27.16 | AG |
| rs1800545 | ADRA2A | 4.54E-02 | 22.51667 | AG |
| rs1532624 | CETP | 4.91E-02 | 14.36907 | TG |
| rs3760396 | CCL2 | 4.96E-02 | 14.3093 | GC |
| Body Mass Index | | | | |
| rs231460 | PYY | 7.36E-04 | 8.283173 | TC |
| rs5030390 | ICAM1 | 8.94E-04 | 10.65952 | AG |
| rs10515070 | PIK3R1 | 5.06E-03 | 8.126625 | AT |
| rs1877394 | PIK3C2B | 5.64E-03 | 24.41429 | AG |
| rs4784642 | GNAO1 | 9.71E-03 | -5.85325 | AG |
| rs8178990 | CHAT | 1.57E-02 | 9.523333 | TC |
| rs2298122 | DRD1IP | 2.01E-02 | 6.401348 | TG |
| rs660339 | UCP2 | 2.17E-02 | -5.20693 | TC |
| rs4762 | AGT | 2.21E-02 | 7.064865 | TC |
| rs1800471 | TGFB1 | 2.52E-02 | 7.953571 | CG |
| rs916829 | ABCC8 | 3.44E-02 | 7.248148 | TC |
| rs3024492 | IL10 | 3.48E-02 | -4.89209 | TA |
| rs1058046 | PYY | 3.75E-02 | 3.923661 | CG |
| rs1801253 | ADRB1 | 4.17E-02 | 4.421711 | GC |
| rs3853188 | SCARB2 | 4.41E-02 | 10.83939 | AC |
| rs4225 | APOA1 | 4.61E-02 | -4.35373 | TG |
| rs1396862 | CRHR1 | 4.97E-02 | 6.53 | TC |
| Waist circumference | | | | |
| rs231460 | PYY | 8.43E-05 | 21.79087 | TC |
| rs5030390 | ICAM1 | 3.80E-03 | 21.91905 | AG |
| rs4762 | AGT | 5.34E-03 | 19.55 | TC |
| rs1801253 | ADRB1 | 3.16E-02 | 10.76974 | GC |

TABLE 2-continued

Arapiprazole

| SNP | Gene | p | Coeff. | Allele |
|---|---|---|---|---|
| rs8178990 | CHAT | 3.16E-02 | 19.78667 | TC |
| rs2515449 | MCPH1 | 3.22E-02 | -17.5595 | AG |
| rs1058046 | PYY | 3.78E-02 | 9.074969 | CG |
| rs132642 | APOL3 | 3.91E-02 | 14.77592 | TA |
| rs264 | LPL | 4.30E-02 | 12.87263 | AG |
| rs3764261 | CETP | 4.37E-02 | 10.24564 | TG |
| rs1058167 | CYP2D6 | 4.41E-02 | -10.1015 | TC |
| rs916829 | ABCC8 | 4.74E-02 | 15.79259 | TC |
| rs10515070 | PIK3R1 | 4.88E-02 | 13.61362 | AT |
| Metabolic Syndromes Index (MSI) | | | | |
| rs11632618 | LIPC | 4.92E-03 | -1.25304 | AG |
| rs2049045 | BDNF | 8.11E-03 | -0.85116 | CG |
| rs231460 | PYY | 9.38E-03 | 0.809173 | TC |
| rs2301108 | HIF1A | 1.33E-02 | 1.003119 | AG |
| rs833060 | VEGF | 1.86E-02 | -0.67721 | TG |
| rs10082776 | RARG | 2.34E-02 | 0.82753 | AG |
| rs4784642 | GNAO1 | 3.13E-02 | -0.60308 | AG |
| rs295 | LPL | 3.81E-02 | -0.56956 | AC |
| rs417344 | LIPC | 4.57E-02 | 0.748564 | TC |
| rs6809631 | PPARG | 4.72E-02 | 0.514632 | AT |
| rs3846662 | HMGCR | 4.84E-02 | 0.459575 | TC |

TABLE 3

Olanzapine

| SNP | Gene | p | coeff | Allele |
|---|---|---|---|---|
| Total Cholesterol | | | | |
| rs1801253 | ADRB1 | 0.001223 | 30.37262 | GC |
| rs12695902 | AGTR1 | 0.006741 | -41.6684 | AG |
| rs1176744 | HTR3B | 0.01552 | 21.22569 | TC |
| rs3769671 | POMC | 0.015975 | 59.9558 | AC |
| rs235249 | TNFRSF1B | 0.019095 | 21.43833 | TC |
| rs5030390 | ICAM1 | 0.019331 | 32.19213 | AG |
| rs9659997 | HTR6 | 0.022789 | 19.88872 | TC |
| rs26312 | GHRL | 0.029481 | -24.4053 | AG |
| rs2429511 | ADRB1 | 0.030389 | -17.479 | AG |
| rs1128503 | ABCB1 | 0.0364 | -18.3247 | TC |
| rs5927 | LDLR | 0.037369 | 20.62031 | AG |
| rs5950584 | LOC441514 | 0.038015 | -20.0075 | TG |
| rs132653 | APOL3 | 0.038278 | -19.5752 | AC |
| rs3761422 | ADORA2A | 0.039604 | 19.06738 | TC |
| rs2241220 | ACACB | 0.04002 | 21.61132 | TC |
| rs1049793 | ABP1 | 0.040719 | -19.0259 | GC |
| rs3219177 | RETN | 0.040893 | 24.45376 | TC |
| rs1061622 | TNFRSF1B | 0.041292 | 18.38678 | TG |
| rs3024492 | IL10 | 0.042968 | -20.7541 | TA |
| rs4646450 | CYP3A5 | 0.044817 | -16.4842 | TC |
| rs3917550 | PON1 | 0.044927 | 27.75278 | TC |
| LDL Cholesterol | | | | |
| rs1049793 | ABP1 | 0.003896 | -17.1602 | GC |
| rs1468271 | NPY | 0.005786 | 25.83161 | AG |
| rs7412 | APOE | 0.007068 | -19.0917 | TC |
| rs4994 | ADRB3 | 0.010221 | 16.80588 | TC |
| rs235249 | TNFRSF1B | 0.010343 | 15.14422 | TC |
| rs3847063 | ACHE | 0.013376 | 12.97031 | AG |
| rs1556478 | LIPA | 0.01557 | 13.54368 | AG |
| rs1061622 | TNFRSF1B | 0.016318 | 13.98472 | TG |
| rs1176744 | HTR3B | 0.017662 | 13.49724 | TG |
| rs1801278 | IRS1 | 0.021042 | -27.4612 | AG |
| rs1442061 | GABRA2 | 0.024327 | -13.0906 | GC |
| rs3024492 | IL10 | 0.02818 | -14.6357 | TA |
| rs2241220 | ACACB | 0.028806 | 14.96556 | TC |
| rs4680 | COMT | 0.035089 | 12.47369 | AG |
| rs894251 | SCARB2 | 0.036234 | -14.2959 | TC |
| rs1478290 | GYS2 | 0.03709 | 14.1317 | TG |
| rs3219177 | RETN | 0.042395 | 16.02753 | TC |
| rs1322783 | DISC1 | 0.048112 | 14.65347 | TC |

TABLE 3-continued

Olanzapine

| SNP | Gene | p | coeff | Allele |
|---|---|---|---|---|
| HDL Cholesterol | | | | |
| rs701492 | GAD1 | 0.000981 | 10.51109 | TC |
| rs132642 | APOL3 | 0.003225 | −12.3949 | TA |
| rs11044082 | PIK3C2G | 0.00527 | 9.326014 | TG |
| rs334555 | GSK3B | 0.00645 | −7.75672 | CG |
| rs931992 | TCAP | 0.007519 | 6.244143 | AC |
| rs2471857 | DRD2 | 0.007741 | 9.560078 | AG |
| rs4301822 | APOF | 0.00871 | 9.352099 | TC |
| rs405509 | APOE | 0.013786 | 5.805556 | AC |
| rs4727666 | PIK3CG | 0.014439 | 6.729684 | AG |
| rs1433099 | LDLR | 0.014831 | 5.743993 | AG |
| rs167771 | DRD3 | 0.016957 | 5.353029 | AG |
| rs7247515 | AKT2 | 0.017361 | 8.520992 | TC |
| rs10505873 | GYS2 | 0.017633 | 5.871088 | TC |
| rs10890819 | ACAT1 | 0.018088 | −6.47656 | TC |
| rs1556478 | LIPA | 0.018247 | −5.99904 | AG |
| rs676643 | HTR1D | 0.022102 | −7.85166 | AG |
| rs11212515 | ACAT1 | 0.023556 | −6.21484 | AT |
| rs4646458 | CYP3A5 | 0.026197 | 8.23594 | AC |
| rs9904270 | RARA | 0.026886 | 9.215385 | TC |
| rs758857 | ADORA2B | 0.034386 | 5.504491 | AG |
| rs461404 | PRKAA1 | 0.034638 | 5.467391 | TC |
| rs4520 | APOC3 | 0.035624 | 6.012063 | TC |
| rs7072137 | GAD2 | 0.036489 | 7.645669 | AG |
| rs1064344 | CHKB | 0.03875 | 7.816842 | AG |
| rs6578993 | TH | 0.039144 | −7.30351 | TC |
| rs5880 | CETP | 0.04589 | −8.67052 | CG |
| rs1800544 | ADRA2A | 0.047067 | 4.387814 | GC |
| rs405509 | APOE | 0.042619 | −0.46019 | AC |
| rs3762272 | PKLR | 0.042684 | 1.981634 | AG |
| rs11212515 | ACAT1 | 0.043078 | 0.532756 | AT |
| rs1799821 | CPT2 | 0.046885 | −0.45137 | AG |
| rs11044082 | PIK3C2G | 0.049177 | −0.63786 | TG |
| Triglycerides (TG) as log(TG) | | | | |
| rs4726107 | LOC441301 | 0.002719 | 0.477536 | TC |
| rs776746 | CYP3A5 | 0.003161 | −0.30155 | AG |
| rs15524 | CYP3A5 | 0.004023 | −0.30332 | TC |
| rs1799983 | NOS3 | 0.004272 | 0.333764 | TG |
| rs4646450 | CYP3A5 | 0.005452 | −0.25311 | TC |
| rs26312 | GHRL | 0.006041 | −0.34147 | AG |
| rs1549758 | NOS3 | 0.010173 | 0.321754 | TC |
| rs1801253 | ADRB1 | 0.011079 | 0.273075 | GC |
| rs701492 | GAD1 | 0.011573 | −0.32259 | TC |
| rs2296189 | FLT1 | 0.012216 | 0.320773 | AG |
| rs2069827 | IL6 | 0.014786 | 0.423743 | TG |
| rs936960 | LIPC | 0.015942 | −0.32209 | AC |
| rs5030390 | ICAM1 | 0.026138 | 0.344851 | AG |
| rs2242480 | CYP3A4 | 0.027458 | −0.22543 | TC |
| rs5369 | EDN1 | 0.02857 | −0.38227 | AG |
| rs1547387 | SLC39A7 | 0.030104 | 0.367289 | GC |
| rs870995 | PIK3CA | 0.034079 | 0.201799 | AC |
| rs1800794 | IL1A | 0.035401 | 0.255309 | TC |
| rs10841044 | PIK3C2G | 0.036964 | 0.27637 | TG |
| rs573542 | ADRA1A | 0.040578 | −0.35838 | AG |
| rs1042718 | ADRB2 | 0.041457 | −0.24971 | AC |
| rs3791850 | GAD1 | 0.047354 | 0.221197 | TC |
| Ratio of Total Cholesterol to HDL Cholesterol | | | | |
| rs776746 | CYP3A5 | 0.00271 | −0.75193 | AG |
| rs4646450 | CYP3A5 | 0.005199 | −0.63063 | TC |
| rs1801105 | HNMT | 0.005396 | 0.959682 | TC |
| rs7072137 | GAD2 | 0.005729 | −0.95334 | AG |
| rs15524 | CYP3A5 | 0.00803 | −0.69616 | TC |
| rs4994 | ADRB3 | 0.009588 | 0.727136 | TC |
| rs701492 | GAD1 | 0.010761 | −0.80015 | TC |
| rs1556478 | LIPA | 0.014715 | 0.584212 | AG |
| rs1800808 | SELP | 0.016787 | 0.967427 | TC |
| rs1468271 | NPY | 0.018601 | 0.952743 | AG |
| rs5880 | CETP | 0.019837 | 0.973258 | CG |
| rs9904270 | RARA | 0.026135 | −0.88494 | TC |
| rs4225 | APOA1 | 0.026898 | −0.50458 | TG |
| rs1049793 | ABP1 | 0.026953 | −0.57163 | GC |
| rs334555 | GSK3B | 0.027904 | 0.604277 | CG |
| rs936960 | LIPC | 0.02832 | −0.72913 | AC |
| rs758857 | ADORA2B | 0.03071 | −0.53693 | AG |
| rs619698 | SSTR5 | 0.03328 | −0.50962 | AC |
| rs3762611 | GABRA4 | 0.035293 | −0.5368 | AG |
| rs1042718 | ADRB2 | 0.036581 | −0.63407 | AC |
| rs2298122 | DRD1IP | 0.041017 | −0.61377 | TG |
| Blood Glucose Level | | | | |
| rs3756450 | SLC6A3 | 0.007877 | 8.623736 | TC |
| rs1001293 | APOL2 | 0.017639 | 8.751749 | TC |
| rs8081866 | ACACA | 0.019008 | 6.939807 | TC |
| rs722341 | ABCC8 | 0.019802 | −12.1303 | TC |
| rs6967107 | WBSCR14 | 0.019942 | −15.1262 | AC |
| rs3176921 | CRH | 0.02 | 7.414049 | TC |
| rs429358 | APOE | 0.023427 | 10.87834 | TC |
| rs10509676 | CYP2C19 | 0.025156 | −8.91429 | TA |
| rs2494746 | AKT1 | 0.025272 | 8.281903 | CG |
| rs3219177 | RETN | 0.029242 | 9.602131 | TC |
| rs5070 | APOA1 | 0.035248 | 6.76981 | AG |
| rs5883 | CETP | 0.039467 | 12.71135 | TC |
| rs2032582 | ABCB1 | 0.04343 | −6.70454 | TG |
| rs1176744 | HTR3B | 0.046503 | 6.594273 | TG |
| Systolic Blood Pressure | | | | |
| rs701492 | GAD1 | 0.005503 | −7.44043 | TC |
| rs707922 | APOM | 0.00642 | 7.008649 | AC |
| rs2702285 | AVEN | 0.009798 | 4.631037 | AG |
| rs3792822 | PRKAA1 | 0.01309 | 6.627359 | AG |
| rs659734 | HTR2A | 0.01862 | 12.77097 | TC |
| rs3762631 | GABRA4 | 0.023278 | −4.95192 | AG |
| rs1801253 | ADRB1 | 0.025182 | 5.131206 | GC |
| rs1614845 | HRH3 | 0.025828 | −6.36655 | TC |
| rs1871143 | GYS2 | 0.029843 | 4.368398 | TG |
| rs3757868 | ACHE | 0.030759 | 5.217643 | AG |
| rs3791850 | GAD1 | 0.033685 | 5.049754 | TC |
| rs2032582 | ABCB1 | 0.040378 | −4.34333 | TG |
| rs6312 | HTR2A | 0.041557 | 8.568966 | AG |
| rs2306179 | GYS2 | 0.04177 | 4.646163 | AG |
| rs1058167 | CYP2D6 | 0.044341 | −3.78129 | TC |
| rs15982 | ACAT2 | 0.045974 | 4.531808 | TC |
| rs694066 | GAL | 0.04672 | 5.111913 | AG |
| rs2298191 | ADORA3 | 0.048235 | 4.05515 | TC |
| Diastolic Blood Pressure | | | | |
| rs3757868 | ACHE | 0.009626 | 5.30302 | AG |
| rs1871143 | GYS2 | 0.010942 | 4.328787 | TG |
| rs1001293 | APOL2 | 0.014057 | 4.971416 | TC |
| rs5742612 | IGF1 | 0.015207 | 9.080346 | TC |
| rs2306179 | GYS2 | 0.018674 | 4.54703 | AG |
| rs707922 | APOM | 0.027116 | 4.905582 | AC |
| rs1018381 | DTNBP1 | 0.028378 | −5.52424 | TC |
| rs15982 | ACAT2 | 0.028686 | 4.217935 | TC |
| rs936960 | LIPC | 0.031299 | −5.25884 | AC |
| rs1040410 | DTNBP1 | 0.031645 | −5.04243 | TC |
| rs11188092 | CYP2C19 | 0.036292 | 5.19788 | AC |
| rs167770 | DRD3 | 0.037371 | −3.85605 | AG |
| rs8178847 | APOH | 0.042355 | −7.27008 | AG |
| rs5766741 | PPARA | 0.044841 | 3.52995 | TC |
| rs706713 | PIK3R1 | 0.044926 | 3.89717 | TC |
| Body Mass | | | | |
| rs7412 | APOE | 0.005557 | 10.93414 | TC |
| rs5092 | APOA4 | 0.011593 | −10.6363 | AG |
| rs4765623 | SCARB1 | 0.014978 | 7.122121 | TC |
| rs4149056 | SLCO1B1 | 0.015513 | −9.582 | TC |
| rs9904270 | RARA | 0.017061 | −12.3209 | TC |
| rs6024725 | MC3R | 0.035653 | −6.55883 | TC |
| rs6032470 | GHRH | 0.039121 | 6.893756 | TC |
| rs1547387 | SLC39A7 | 0.043481 | 11.06101 | GC |
| rs2067477 | CHRM1 | 0.04394 | −25.6493 | AC |
| Body Mass Index | | | | |
| rs2067477 | CHRM1 | 0.013434 | −9.93539 | AC |
| rs1799983 | NOS3 | 0.017312 | 2.872978 | TG |
| rs5092 | APOA4 | 0.019485 | −3.14289 | AG |
| rs4149056 | SLCO1B1 | 0.020121 | −2.96415 | TC |
| rs9904270 | RARA | 0.021753 | −3.77721 | TC |

TABLE 3-continued

Olanzapine

| SNP | Gene | p | coeff | Allele |
|---|---|---|---|---|
| rs4520 | APOC3 | 0.023255 | -2.56317 | TC |
| rs1547387 | SLC39A7 | 0.023275 | 3.938596 | GC |
| rs6024725 | MC3R | 0.02575 | -2.21035 | TC |
| rs132642 | APOL3 | 0.02637 | -3.75273 | TA |
| rs4135268 | PPARG | 0.026473 | -3.24058 | GC |
| rs6901 | PFKP | 0.032439 | -2.55325 | AG |
| rs1549758 | NOS3 | 0.038073 | 2.570116 | TC |
| rs619698 | SSTR5 | 0.040624 | 2.03538 | AC |
| rs1128503 | ABCB1 | 0.042111 | -2.05667 | TC |
| rs891087 | INSR | 0.042167 | 3.540971 | AG |
| rs3024492 | IL10 | 0.042447 | -2.40166 | TA |
| rs10515070 | PIK3R1 | 0.048723 | 2.034725 | AT |

Waist circumference

| SNP | Gene | p | coeff | Allele |
|---|---|---|---|---|
| rs2067477 | CHRM1 | 0.016089 | -24.0911 | AC |
| rs4149056 | SLCO1B1 | 0.02202 | -7.22366 | TC |
| rs1547387 | SLC39A7 | 0.026583 | 9.58381 | GC |
| rs5092 | APOA4 | 0.030408 | -7.26556 | AG |
| rs1029947 | PRKAG2 | 0.032913 | -7.53118 | AG |
| rs7412 | APOE | 0.034503 | 6.67961 | TC |
| rs9904270 | RARA | 0.04255 | -8.34082 | TC |
| rs2734830 | UCP3 | 0.044493 | -12.941 | AG |
| rs2071521 | APOC3 | 0.045539 | -4.96246 | TC |

Metabolic Syndromes Index (MSI)

| SNP | Gene | p | coeff | Allele |
|---|---|---|---|---|
| rs1799983 | NOS3 | 0.000696 | 0.826292 | TG |
| rs936960 | LIPC | 0.000898 | -0.92233 | AC |
| rs9904270 | RARA | 0.002448 | -1.01453 | TC |
| rs1549758 | NOS3 | 0.002655 | 0.793918 | TC |
| rs7247515 | AKT2 | 0.003897 | -0.83653 | TC |
| rs701492 | GAD1 | 0.008561 | -0.70823 | TC |
| rs814628 | LIPF | 0.009502 | 0.816129 | AG |
| rs15524 | CYP3A5 | 0.018134 | -0.53369 | TC |
| rs4646458 | CYP3A5 | 0.021028 | -0.71167 | AC |
| rs776746 | CYP3A5 | 0.021169 | -0.50581 | AG |
| rs1396862 | CRHR1 | 0.025504 | 0.621601 | TC |
| rs1128503 | ABCB1 | 0.025772 | -0.46437 | TC |
| rs1049793 | ABP1 | 0.027114 | -0.48842 | GC |
| rs2734830 | UCP3 | 0.031033 | -1.15302 | AG |
| rs10509676 | CYP2C19 | 0.031106 | -0.55056 | TA |
| rs4727666 | PIK3CG | 0.031253 | -0.48686 | AG |
| rs5742612 | IGF1 | 0.031666 | 0.941118 | TC |
| rs573542 | ADRA1A | 0.03408 | -0.78533 | AG |
| rs2743867 | DTNBP1 | 0.035656 | -0.50526 | AG |
| rs676210 | APOB | 0.04125 | -0.5054 | AG |
| rs7072137 | GAD2 | 0.04443 | -0.60141 | AG |
| rs3846662 | HMGCR | 0.04644 | 0.379953 | TC |
| rs891087 | INSR | 0.047551 | 0.71352 | AG |
| rs3762611 | GABRA4 | 0.048817 | -0.43299 | AG |

TABLE 4

Quetiapine

| SNP | Gene | p | Coeff. | Allele |
|---|---|---|---|---|
| Total Cholesterol | | | | |
| rs2228139 | IL1R1 | 3.89E-03 | -41.2853 | GC |
| rs2230461 | PIK3CA | 9.48E-03 | 34.65799 | AG |
| rs7520974 | CHRM3 | 1.27E-02 | 18.7906 | AG |
| rs12695902 | AGTR1 | 1.44E-02 | 25.38039 | AG |
| rs3791981 | APOB | 1.52E-02 | 25.59187 | AG |
| rs5368 | SELE | 1.81E-02 | 27.81579 | TC |
| rs4149056 | SLCO1B1 | 2.04E-02 | -15.0481 | TC |
| rs2020933 | SLC6A4 | 2.33E-02 | 31.49038 | AT |
| rs3219177 | RETN | 2.80E-02 | 17.40625 | TC |
| rs2069827 | IL6 | 3.05E-02 | -21.7734 | TG |
| rs2287754 | GYS1 | 3.59E-02 | -26.5669 | AG |
| rs2162189 | SST | 3.61E-02 | 20.16743 | AG |
| rs659734 | HTR2A | 4.43E-02 | 28.62249 | TC |
| rs2471857 | DRD2 | 4.75E-02 | 16.12131 | AG |
| rs6586179 | LIPA | 4.89E-02 | 19.38148 | TC |

TABLE 4-continued

Quetiapine

| SNP | Gene | p | Coeff. | Allele |
|---|---|---|---|---|
| LDL Cholesterol | | | | |
| rs2228139 | IL1R1 | 8.14E-03 | -28.4481 | GC |
| rs10934502 | GSK3B | 1.13E-02 | 16.6821 | TC |
| rs4688046 | GSK3B | 1.13E-02 | 16.6821 | TC |
| rs3087454 | CHRNA7 | 1.67E-02 | 12.36429 | TG |
| rs662 | PON1 | 1.71E-02 | -14.229 | AG |
| rs1061622 | TNFRSF1B | 1.76E-02 | -13.1239 | TG |
| rs2162189 | SST | 2.05E-02 | 16.68097 | AG |
| rs235249 | TNFRSF1B | 2.17E-02 | -12.3796 | TC |
| rs7520974 | CHRM3 | 2.57E-02 | 12.84808 | AG |
| rs6586179 | LIPA | 2.62E-02 | 16.36284 | TC |
| rs3917550 | PON1 | 2.90E-02 | -19.7091 | TC |
| rs7247515 | AKT2 | 3.15E-02 | -17.0643 | TC |
| rs3791981 | APOB | 3.51E-02 | 16.72686 | AG |
| rs659734 | HTR2A | 4.25E-02 | 21.63211 | TC |
| HDL Cholesterol | | | | |
| rs10494851 | PIK3C2B | 5.15E-03 | -35.3763 | AG |
| rs2734830 | UCP3 | 5.50E-03 | -35.3226 | AG |
| rs264 | LPL | 9.47E-03 | 7.417559 | AG |
| rs3791981 | APOB | 9.88E-03 | 7.544543 | AG |
| rs7072137 | GAD2 | 1.22E-02 | 6.62058 | AG |
| rs686874 | HRH2 | 1.69E-02 | 10.18235 | TC |
| rs7975375 | ADIPOR2 | 1.95E-02 | 4.345878 | TC |
| rs4726107 | LOC441301 | 1.99E-02 | -4.88734 | TC |
| rs6083 | LIPC | 2.09E-02 | -4.2827 | AG |
| rs2742115 | OLR1 | 2.55E-02 | -4.52595 | AG |
| rs2070937 | HP | 2.55E-02 | -4.30836 | AG |
| rs9904270 | RARA | 3.04E-02 | -6.45929 | TC |
| rs4727666 | PIK3CG | 3.08E-02 | 4.497207 | AG |
| rs1556478 | LIPA | 3.25E-02 | 4.148085 | AG |
| rs6078 | LIPC | 4.09E-02 | -12.0222 | AG |
| rs1131010 | PECAM1 | 4.28E-02 | -18.3913 | TC |
| Triglycerides (TG) as log(TG) | | | | |
| rs3219177 | RETN | 2.41E-03 | 0.287331 | TC |
| rs6078 | LIPC | 6.63E-03 | 0.688958 | AG |
| rs2287754 | GYS1 | 8.16E-03 | -0.40224 | AG |
| rs4646450 | CYP3A5 | 1.09E-02 | -0.22358 | TC |
| rs1801253 | ADRB1 | 1.09E-02 | -0.24538 | GC |
| rs2230461 | PIK3CA | 1.76E-02 | 0.384772 | AG |
| rs2228139 | IL1R1 | 2.52E-02 | -0.39047 | GC |
| rs10494851 | PIK3C2B | 2.62E-02 | 1.238439 | AG |
| rs2734830 | UCP3 | 2.79E-02 | 1.233904 | AG |
| rs4765623 | SCARB1 | 2.95E-02 | 0.217489 | TC |
| rs2838549 | PFKL | 3.02E-02 | -0.27635 | AG |
| rs461404 | PRKAA1 | 3.05E-02 | -0.17495 | TC |
| rs5950584 | LOC441514 | 3.89E-02 | -0.33636 | TG |
| rs686874 | HRH2 | 5.00E-02 | -0.36539 | TC |
| Ratio of Total Cholesterol to HDL Cholesterol | | | | |
| rs4646450 | CYP3A5 | 7.64E-03 | -0.53585 | TC |
| rs8192708 | PCK1 | 1.00E-02 | 0.866536 | AG |
| rs3219177 | RETN | 1.44E-02 | 0.535896 | TC |
| rs854572 | PON1 | 1.64E-02 | -0.41785 | CG |
| rs4765623 | SCARB1 | 1.83E-02 | 0.540148 | TC |
| rs6489738 | GNB3 | 2.02E-02 | -0.44592 | AG |
| rs2228139 | IL1R1 | 2.30E-02 | -0.90586 | GC |
| rs3756450 | SLC6A3 | 3.50E-02 | 0.634007 | TC |
| rs12695902 | AGTR1 | 3.83E-02 | 0.5939 | AG |
| rs7072137 | GAD2 | 3.90E-02 | -0.54635 | AG |
| Blood Glucose Level | | | | |
| rs1176744 | HTR3B | 6.12E-04 | 7.805944 | TG |
| rs2229126 | ADRA1A | 3.92E-03 | 30.52881 | AT |
| rs1801278 | IRS1 | 4.01E-03 | 12.04125 | AG |
| rs4520 | APOC3 | 1.31E-02 | 6.670354 | TC |
| rs4890109 | RARA | 1.42E-02 | -18.783 | TG |
| rs3762611 | GABRA4 | 2.21E-02 | 8.232796 | AG |
| rs446037 | APOE | 2.37E-02 | 29.4082 | AC |
| rs2227852 | DRD5 | 2.63E-02 | 9.6734 | AG |
| rs1171276 | LEPR | 2.65E-02 | 6.433188 | AG |
| rs5070 | APOA1 | 3.34E-02 | 5.786811 | AG |
| rs1440451 | HTR5A | 3.63E-02 | 15.80298 | CG |
| rs877172 | OXT | 3.71E-02 | 6.305725 | AC |

TABLE 4-continued

Quetiapine

| SNP | Gene | p | Coeff. | Allele |
|---|---|---|---|---|
| rs10890819 | ACAT1 | 4.18E−02 | 5.515977 | TC |
| rs1042718 | ADRB2 | 4.24E−02 | 8.172986 | AC |
| rs6078 | LIPC | 4.62E−02 | 16.72132 | AG |
| rs3176921 | CRH | 4.88E−02 | 7.974232 | TC |
| rs1355920 | CHRNA7 | 4.99E−02 | 7.39564 | AG |
| Systolic Blood Pressure | | | | |
| rs1800794 | IL1A | 3.96E−03 | −5.0646 | TC |
| rs11100494 | NPY5R | 8.71E−03 | 7.055101 | AC |
| rs3847063 | ACHE | 1.33E−02 | −4.08239 | AG |
| rs4301822 | APOF | 1.37E−02 | 10.08375 | TC |
| rs3769671 | POMC | 1.52E−02 | 11.57612 | AC |
| rs1356413 | PIK3CA | 1.53E−02 | 7.935075 | GC |
| rs8110695 | LDLR | 1.54E−02 | 5.270074 | AT |
| rs1143634 | IL1B | 1.59E−02 | −4.44092 | TC |
| rs1029947 | PRKAG2 | 1.63E−02 | 6.15884 | AG |
| rs619698 | SSTR5 | 1.72E−02 | 4.130632 | AC |
| rs5070 | APOA1 | 2.07E−02 | 3.906858 | AG |
| rs1556478 | LIPA | 2.08E−02 | 3.969224 | AG |
| rs231460 | PYY | 2.27E−02 | 4.946087 | TC |
| rs4225 | APOA1 | 2.40E−02 | 3.474329 | TG |
| rs821616 | DISC1 | 3.16E−02 | −4.1081 | TA |
| rs1058046 | PYY | 3.37E−02 | 3.806571 | CG |
| rs1001293 | APOL2 | 3.65E−02 | 5.703745 | TC |
| rs2066470 | MTHFR | 3.82E−02 | 6.617426 | TC |
| rs132642 | APOL3 | 4.42E−02 | −5.51148 | TA |
| Diastolic Blood Pressure | | | | |
| rs2287754 | GYS1 | 8.23E−05 | −8.49517 | AG |
| rs4784642 | GNAO1 | 1.43E−02 | −2.92722 | AG |
| rs2228139 | IL1R1 | 1.44E−02 | −6.18353 | GC |
| rs5070 | APOA1 | 1.47E−02 | 2.93003 | AG |
| rs7072137 | GAD2 | 1.55E−02 | −4.04415 | AG |
| rs1800794 | IL1A | 1.88E−02 | −2.96219 | TC |
| rs4149578 | TNFRSF1A | 1.94E−02 | −4.02141 | AG |
| rs1891311 | HTR7 | 2.26E−02 | −4.602 | AG |
| rs10515521 | NR3C1 | 2.41E−02 | −3.53261 | AG |
| rs3822222 | CCKAR | 3.84E−02 | 3.681413 | TC |
| rs1438732 | NR3C1 | 4.95E−02 | 3.046512 | CG |
| Body Mass | | | | |
| rs3810947 | CHAT | 8.57E−04 | 18.02606 | AG |
| rs1290443 | RARB | 3.21E−03 | 12.01211 | AG |
| rs8192708 | PCK1 | 3.41E−03 | 16.37595 | AG |
| rs405509 | APOE | 7.24E−03 | −8.34124 | AC |
| rs1891311 | HTR7 | 9.70E−03 | −13.8376 | AG |
| rs8110695 | LDLR | 2.06E−02 | 9.414508 | AT |
| rs1801105 | HNMT | 2.54E−02 | 12.89213 | TC |
| rs1042718 | ADRB2 | 2.99E−02 | 10.19276 | AC |
| rs7520974 | CHRM3 | 3.06E−02 | −7.48181 | AG |
| rs3808607 | CYP7A1 | 3.10E−02 | −7.6478 | TG |
| rs1190762 | GNAO1 | 3.59E−02 | 12.11352 | AC |
| rs597316 | CPT1A | 3.60E−02 | −6.3654 | GC |
| rs1800794 | IL1A | 3.70E−02 | −6.90293 | TC |
| rs849404 | PIK3CG | 3.72E−02 | 9.838892 | AG |
| rs1800871 | IL10 | 3.99E−02 | −7.27912 | TC |
| rs6083 | LIPC | 4.05E−02 | 6.275497 | AG |
| rs2298122 | DRD1IP | 4.56E−02 | 7.662822 | TG |
| rs235249 | TNFRSF1B | 4.58E−02 | −6.6169 | TC |
| rs4072032 | PECAM1 | 4.72E−02 | 5.489824 | TC |
| rs7556371 | PIK3C2B | 4.77E−02 | 5.920468 | AG |
| rs7247515 | AKT2 | 4.85E−02 | 9.575336 | TC |
| rs10494852 | PIK3C2B | 4.89E−02 | 5.872506 | AG |
| Body Mass Index | | | | |
| rs619698 | SSTR5 | 9.32E−04 | 3.529752 | AC |
| rs3810947 | CHAT | 1.31E−03 | 5.855003 | AG |
| rs12691940 | HNMT | 1.51E−03 | 3.351832 | AG |
| rs5896 | F2 | 2.59E−03 | 5.063378 | TC |
| rs3176921 | CRH | 5.37E−03 | 4.328492 | TC |
| rs885834 | CHAT | 1.64E−02 | 2.413419 | AG |
| rs5742612 | IGF1 | 2.24E−02 | 6.360434 | TC |
| rs3822222 | CCKAR | 2.31E−02 | 3.534367 | TC |
| rs1801105 | HNMT | 2.39E−02 | 4.373905 | TC |
| rs3760396 | CCL2 | 3.18E−02 | 2.637853 | GC |
| rs7520974 | CHRM3 | 3.70E−02 | −2.42909 | AG |

TABLE 4-continued

Quetiapine

| SNP | Gene | p | Coeff. | Allele |
|---|---|---|---|---|
| rs3808607 | CYP7A1 | 3.90E−02 | −2.4642 | TG |
| rs2430683 | ACACB | 4.13E−02 | −2.84913 | TG |
| rs1042718 | ADRB2 | 4.19E−02 | 3.181829 | AC |
| rs2298122 | DRD1IP | 4.39E−02 | 2.591716 | TG |
| rs891087 | INSR | 4.54E−02 | −3.04219 | AG |
| Waist circumference | | | | |
| rs1356413 | PIK3CA | 5.55E−03 | 13.08343 | GC |
| rs1283694 | ANGPT1 | 6.03E−03 | 8.273119 | TA |
| rs132653 | APOL3 | 1.04E−02 | 9.286263 | AC |
| rs597316 | CPT1A | 1.05E−02 | −6.05607 | GC |
| rs3176921 | CRH | 1.16E−02 | 9.289985 | TC |
| rs5896 | F2 | 1.16E−02 | 10.11501 | TC |
| rs3810947 | CHAT | 1.29E−02 | 10.89659 | AG |
| rs885834 | CHAT | 1.30E−02 | 5.788291 | AG |
| rs4762 | AGT | 1.95E−02 | 10.50311 | TC |
| rs5742612 | IGF1 | 2.23E−02 | 14.79145 | TC |
| rs4890109 | RARA | 2.32E−02 | −15.6951 | TG |
| rs619698 | SSTR5 | 3.23E−02 | 5.624951 | AC |
| rs7975375 | ADIPOR2 | 3.31E−02 | 5.254994 | TC |
| rs405509 | APOE | 3.40E−02 | −5.25172 | AC |
| rs1290443 | RARB | 3.60E−02 | 6.77693 | AG |
| rs4933200 | ANKRD1 | 3.85E−02 | 6.629549 | TC |
| rs1801123 | IRS1 | 3.95E−02 | 7.79809 | AG |
| rs1322783 | DISC1 | 3.95E−02 | 6.861063 | TC |
| rs8178847 | APOH | 4.25E−02 | −11.1533 | AG |
| rs1800871 | IL10 | 4.63E−02 | −5.5271 | TC |
| rs870995 | PIK3CA | 4.82E−02 | −4.80408 | AC |
| rs573542 | ADRA1A | 4.97E−02 | 11.3178 | AG |
| Metabolic Syndromes Index (MSI) | | | | |
| rs6078 | LIPC | 9.08E−03 | 1.537607 | AG |
| rs4646450 | CYP3A5 | 9.60E−03 | −0.527 | TC |
| rs2287754 | GYS1 | 1.31E−02 | −0.87667 | AG |
| rs11503016 | GABRA2 | 1.34E−02 | 0.709914 | TA |
| rs7072137 | GAD2 | 1.44E−02 | −0.65262 | AG |
| rs5070 | APOA1 | 2.01E−02 | 0.446818 | AG |
| rs686874 | HRH2 | 2.03E−02 | −0.99858 | TC |
| rs4792887 | CRHR1 | 3.38E−02 | −0.55749 | TC |
| rs3176921 | CRH | 3.53E−02 | 0.602068 | TC |
| rs1042718 | ADRB2 | 3.75E−02 | 0.592953 | AC |
| rs619698 | SSTR5 | 4.72E−02 | 0.389961 | AC |

TABLE 5

Risperidone

| SNP | Gene | p | Coeff. | Allele |
|---|---|---|---|---|
| Total Cholesterol | | | | |
| rs2125489 | KDR | 0.00047 | 32.06932 | TC |
| rs417344 | LIPC | 0.001837 | 22.24915 | TC |
| rs3764261 | CETP | 0.00305 | 17.57504 | TG |
| rs2071710 | SSTR3 | 0.014983 | −17.5282 | AG |
| rs6700734 | TNFSF6 | 0.017732 | 17.95779 | AG |
| rs7602 | LEPR | 0.023492 | 14.93003 | AG |
| rs3791850 | GAD1 | 0.023687 | 14.87176 | TC |
| rs167771 | DRD3 | 0.026398 | −13.8686 | AG |
| rs7641983 | PIK3CA | 0.033181 | −13.6397 | TC |
| rs136163 | APOL1 | 0.033538 | 16.31087 | TG |
| rs334555 | GSK3B | 0.036431 | 17.69284 | CG |
| rs1532624 | CETP | 0.036792 | 10.94538 | TG |
| rs9288993 | DRD3 | 0.039195 | −23.9266 | AG |
| rs870995 | PIK3CA | 0.039316 | 11.31637 | AC |
| rs3808607 | CYP7A1 | 0.042154 | 10.8532 | TG |
| rs1800544 | ADRA2A | 0.045876 | −11.1261 | GC |
| rs6809631 | PPARG | 0.047978 | 11.52797 | AT |
| LDL Cholesterol | | | | |
| rs2071710 | SSTR3 | 0.004202 | −16.7661 | AG |
| rs3846662 | HMGCR | 0.005263 | 11.49648 | TC |
| rs3808607 | CYP7A1 | 0.00528 | 12.06923 | TG |

TABLE 5-continued

Risperidone

| SNP | Gene | p | Coeff. | Allele |
|---|---|---|---|---|
| rs2125489 | KDR | 0.010605 | 19.43182 | TC |
| rs136163 | APOL1 | 0.013002 | 15.51723 | TG |
| rs231460 | PYY | 0.016147 | 11.92898 | TC |
| rs916829 | ABCC8 | 0.017234 | 16.07353 | TC |
| rs6700734 | TNFSF6 | 0.019519 | 14.32157 | AG |
| rs5896 | F2 | 0.022358 | −15.2313 | TC |
| rs6032470 | GHRH | 0.023791 | −13.7356 | TC |
| rs204987 | NOTCH4 | 0.024645 | −30.1351 | AG |
| rs7641983 | PIK3CA | 0.040991 | −10.7093 | TC |
| rs417344 | LIPC | 0.043577 | 11.95133 | TC |
| rs1800544 | ADRA2A | 0.044729 | −9.14378 | GC |
| rs1041163 | VCAM1 | 0.047082 | 11.68301 | TC |
| rs10513055 | PIK3CB | 0.047249 | −11.5433 | AC |
| rs521674 | ADRA2A | 0.049089 | −9.463 | AT |

HDL Cholesterol

| SNP | Gene | p | Coeff. | Allele |
|---|---|---|---|---|
| rs849404 | PIK3CG | 0.000167 | 9.587355 | AG |
| rs1532624 | CETP | 0.000363 | 6.370909 | TG |
| rs711752 | CETP | 0.01407 | 4.661647 | AG |
| rs10513055 | PIK3CB | 0.016067 | 5.934702 | AC |
| rs132642 | APOL3 | 0.017338 | −6.40653 | TA |
| rs916829 | ABCC8 | 0.019536 | −6.71266 | TC |
| rs1433099 | LDLR | 0.022109 | −4.64908 | AG |
| rs1556478 | LIPA | 0.022948 | −4.22922 | AG |
| rs5927 | LDLR | 0.026179 | −4.94688 | AG |
| rs1935349 | HTR7 | 0.026968 | 6.356268 | AG |
| rs2067477 | CHRM1 | 0.029144 | 7.737937 | AC |
| rs10460960 | LOC391530 | 0.033308 | −4.9791 | AG |
| rs722341 | ABCC8 | 0.034767 | 6.385556 | TC |
| rs3764261 | CETP | 0.03957 | 4.298277 | TG |
| rs1438732 | NR3C1 | 0.039901 | −5.33097 | CG |
| rs1801282 | PPARG | 0.040087 | −6.1934 | CG |
| rs2514869 | ANGPT1 | 0.041908 | −6.06258 | TC |
| rs573542 | ADRA1A | 0.041928 | 8.049963 | AG |
| rs132653 | APOL3 | 0.045271 | −4.95306 | AC |
| rs903361 | ADORA1 | 0.049902 | 4.053673 | TC |

Triglycerides (TG) as log (TG)

| SNP | Gene | p | Coeff. | Allele |
|---|---|---|---|---|
| rs1049793 | ABP1 | 0.004532 | 0.207526 | GC |
| rs4531 | DBH | 0.006808 | −0.33274 | TG |
| rs3791850 | GAD1 | 0.006847 | 0.224689 | TC |
| rs7211875 | TADA2L | 0.014373 | −0.24949 | TC |
| rs7412 | APOE | 0.017561 | 0.341852 | TC |
| rs1001293 | APOL2 | 0.018884 | −0.30888 | TC |
| rs686874 | HRH2 | 0.022611 | −0.44532 | TC |
| rs3764261 | CETP | 0.026459 | 0.168949 | TG |
| rs3771892 | TNFAIP6 | 0.027902 | −0.19775 | AG |
| rs1046668 | TNFAIP6 | 0.027902 | −0.19775 | AG |
| rs7247515 | AKT2 | 0.03024 | 0.252216 | TC |
| rs10508244 | PFKP | 0.032423 | −0.30876 | TC |
| rs2807071 | OAT | 0.037849 | −0.21125 | TC |
| rs11212515 | ACAT1 | 0.03906 | 0.156983 | AT |
| rs1611115 | DBH | 0.039706 | 0.179453 | TC |
| rs10890819 | ACAT1 | 0.040812 | 0.155058 | TC |
| rs758857 | ADORA2B | 0.042602 | 0.160714 | AG |

Ratio of Total Cholesterol to HDL Cholesterol

| SNP | Gene | p | Coeff. | Allele |
|---|---|---|---|---|
| rs10513055 | PIK3CB | 0.000417 | −0.6816 | AC |
| rs11212515 | ACAT1 | 0.001159 | 0.530754 | AT |
| rs10890819 | ACAT1 | 0.001357 | 0.521826 | TC |
| rs1801282 | PPARG | 0.00146 | 0.75362 | CG |
| rs903361 | ADORA1 | 0.002079 | −0.49993 | TC |
| rs916829 | ABCC8 | 0.002507 | 0.685811 | TC |
| rs11044082 | PIK3C2G | 0.009089 | 0.466704 | TG |
| rs2514869 | ANGPT1 | 0.013431 | 0.583976 | TC |
| rs1935349 | HTR7 | 0.021689 | −0.52506 | AG |
| rs521674 | ADRA2A | 0.027569 | −0.35846 | AT |
| rs1532624 | CETP | 0.027789 | −0.3194 | TG |
| rs9904270 | RARA | 0.031437 | −0.50417 | TC |
| rs1800544 | ADRA2A | 0.033748 | −0.32761 | GC |
| rs4531 | DBH | 0.036081 | −0.56644 | TG |
| rs2807071 | OAT | 0.042835 | −0.45071 | TC |
| rs6032470 | GHRH | 0.043166 | −0.41778 | TC |
| rs2221223 | CHRNA7 | 0.044664 | 0.461246 | AC |
| rs132642 | APOL3 | 0.045964 | 0.429822 | TA |
| rs745075 | MTP | 0.048066 | −0.61686 | AG |
| rs6809631 | PPARG | 0.048472 | 0.318943 | AT |

Blood Glucose Level

| SNP | Gene | p | Coeff. | Allele |
|---|---|---|---|---|
| rs3771892 | TNFAIP6 | 0.008177 | −10.271 | AG |
| rs1046668 | TNFAIP6 | 0.008177 | −10.271 | AG |
| rs1800588 | LIPC | 0.008419 | 11.17577 | TC |
| rs2296189 | FLT1 | 0.013562 | 9.078293 | AG |
| rs10934502 | GSK3B | 0.015109 | 9.188489 | TC |
| rs1801105 | HNMT | 0.017791 | 11.50366 | TC |
| rs1040410 | DTNBP1 | 0.018143 | −11.2598 | TC |
| rs2743867 | DTNBP1 | 0.018143 | −11.2598 | AG |
| rs1018381 | DTNBP1 | 0.018143 | −11.2598 | TC |
| rs5092 | APOA4 | 0.01889 | −9.74029 | AG |
| rs659734 | HTR2A | 0.020241 | 12.39458 | TC |
| rs26312 | GHRL | 0.020508 | 11.16645 | AG |
| rs7247515 | AKT2 | 0.031294 | 11.04629 | TC |
| rs107540 | CRHR2 | 0.037255 | −7.05952 | AG |
| rs4149056 | SLCO1B1 | 0.038841 | 7.89813 | TC |
| rs446037 | APOE | 0.044594 | 30.76295 | AC |
| rs1356413 | PIK3CA | 0.045483 | 14.99419 | GC |
| rs132642 | APOL3 | 0.048311 | −8.52411 | TA |
| rs12691940 | HNMT | 0.04906 | 6.351026 | AG |

Systolic Blood Pressure

| SNP | Gene | p | Coeff. | Allele |
|---|---|---|---|---|
| rs157864 | RXRG | 0.007033 | −5.4985 | TC |
| rs1611115 | DBH | 0.007497 | 4.266524 | TC |
| rs3847063 | ACHE | 0.00936 | −3.23301 | AG |
| rs11632618 | LIPC | 0.010777 | 7.40404 | AG |
| rs2020933 | SLC6A4 | 0.011829 | 5.19419 | AT |
| rs2278718 | MDH1 | 0.012499 | 4.10129 | AC |
| rs573542 | ADRA1A | 0.013255 | −6.5604 | AG |
| rs167770 | DRD3 | 0.028298 | 2.79318 | AG |
| rs10515521 | NR3C1 | 0.030187 | −3.97406 | AG |
| rs4646450 | CYP3A5 | 0.031668 | 3.239881 | TC |
| rs334555 | GSK3B | 0.035254 | 4.168216 | CG |
| rs10507383 | FLT1 | 0.047122 | 4.95 | CG |
| rs34274 | ACACB | 0.048146 | 2.825677 | TC |

Diastolic Blood Pressure

| SNP | Gene | p | Coeff. | Allele |
|---|---|---|---|---|
| rs1532624 | CETP | 0.000672 | 3.431632 | TG |
| rs2015353 | ADRA2B | 0.001135 | 3.194454 | AG |
| rs334555 | GSK3B | 0.002007 | 5.054833 | CG |
| rs711752 | CETP | 0.002165 | 3.251072 | AG |
| rs3847063 | ACHE | 0.003419 | −3.03509 | AG |
| rs4646450 | CYP3A5 | 0.003756 | 3.623853 | TC |
| rs2288911 | APOC4 | 0.005099 | −3.28419 | AC |
| rs167770 | DRD3 | 0.00634 | 2.88953 | AG |
| rs891087 | INSR | 0.007021 | 5.097546 | AG |
| rs1049793 | ABP1 | 0.008505 | 2.920394 | GC |
| rs2058112 | ADIPOR2 | 0.010034 | 3.910813 | TC |
| rs931490 | AGTR1 | 0.011462 | −3.82066 | AG |
| rs1396862 | CRHR1 | 0.012197 | −3.84848 | TC |
| rs6700734 | TNFSF6 | 0.01298 | −3.68074 | AG |
| rs7975375 | ADIPOR2 | 0.013235 | 3.833333 | TC |
| rs6578993 | TH | 0.014221 | −3.6173 | TC |
| rs3764261 | CETP | 0.016267 | 2.815101 | TG |
| rs1951795 | HIF1A | 0.022656 | 2.588957 | AC |
| rs676210 | APOB | 0.028343 | −3.147 | AG |
| rs3766560 | ADORA1 | 0.030057 | −3.21849 | AG |
| rs7072137 | GAD2 | 0.030798 | −4.69916 | AG |
| rs2807071 | OAT | 0.031387 | −3.39646 | TC |
| rs34274 | ACACB | 0.0333 | 2.544004 | TC |
| rs12691940 | HNMT | 0.040459 | 2.318693 | AG |
| rs6078 | LIPC | 0.042439 | −5.72446 | AG |
| rs2867383 | DRD5 | 0.042497 | −2.06108 | AG |

Body Mass

| SNP | Gene | p | Coeff. | Allele |
|---|---|---|---|---|
| rs8179183 | LEPR | 0.000988 | −11.1401 | CG |
| rs705381 | PON1 | 0.001184 | −9.19215 | TC |
| rs6837793 | NPY5R | 0.002384 | 12.83107 | AG |
| rs2807071 | OAT | 0.005651 | −10.1917 | TC |
| rs1801282 | PPARG | 0.005839 | 10.93761 | CG |
| rs4784642 | GNAO1 | 0.006622 | −6.16455 | AG |
| rs6578993 | TH | 0.00836 | −9.14217 | TC |
| rs6032470 | GHRH | 0.008911 | 8.934572 | TC |

TABLE 5-continued

Risperidone

| SNP | Gene | p | Coeff. | Allele |
|---|---|---|---|---|
| rs854572 | PON1 | 0.01022 | −6.32248 | CG |
| rs132653 | APOL3 | 0.010662 | 8.326152 | AC |
| rs2241220 | ACACB | 0.014934 | 8.478585 | TC |
| rs6901 | PFKP | 0.015417 | 7.144869 | AG |
| rs1611115 | DBH | 0.015742 | 7.622235 | TC |
| rs931490 | AGTR1 | 0.016355 | −8.63382 | AG |
| rs136163 | APOL1 | 0.017456 | −8.39594 | TG |
| rs3853188 | SCARB2 | 0.022371 | 9.670086 | AC |
| rs334555 | GSK3B | 0.023294 | 8.839278 | CG |
| rs4802071 | AKT2 | 0.028691 | −5.53247 | TC |
| rs1433099 | LDLR | 0.032383 | 5.774847 | AG |
| rs7247515 | AKT2 | 0.032488 | 9.043362 | TC |
| rs891087 | INSR | 0.032929 | 9.563677 | AG |
| rs4994 | ADRB3 | 0.037363 | −8.98778 | TC |
| rs157864 | RXRG | 0.038632 | −8.38123 | TC |
| rs235249 | TNFRSF1B | 0.049395 | −5.97766 | TC |

Body Mass Index

| SNP | Gene | p | Coeff. | Allele |
|---|---|---|---|---|
| rs8179183 | LEPR | 0.001833 | −3.20688 | CG |
| rs705381 | PON1 | 0.009591 | −2.24937 | TC |
| rs1801282 | PPARG | 0.010029 | 3.107561 | CG |
| rs6837793 | NPY5R | 0.010389 | 3.306633 | AG |
| rs1532624 | CETP | 0.011457 | −1.84709 | TG |
| rs2807071 | OAT | 0.014478 | −2.74386 | TC |
| rs2241220 | ACACB | 0.018863 | 2.484713 | TC |
| rs2734830 | UCP3 | 0.022128 | 8.917172 | AG |
| rs132653 | APOL3 | 0.023546 | 2.248329 | AC |
| rs6032470 | GHRH | 0.023627 | 2.356124 | TC |
| rs334555 | GSK3B | 0.024036 | 2.668402 | CG |
| rs854572 | PON1 | 0.025565 | −1.67466 | CG |
| rs4784642 | GNAO1 | 0.02567 | −1.54639 | AG |
| rs7247515 | AKT2 | 0.027453 | 2.827675 | TC |
| rs711752 | CETP | 0.029743 | −1.66622 | AG |
| rs833060 | VEGF | 0.030174 | −2.11956 | TG |
| rs6078 | LIPC | 0.031632 | −4.32715 | AG |
| rs157864 | RXRG | 0.031737 | −2.63894 | TC |
| rs1800808 | SELP | 0.034302 | −2.5363 | TC |
| rs660339 | UCP2 | 0.035545 | 1.770583 | TC |
| rs3853188 | SCARB2 | 0.036343 | 2.694731 | AC |
| rs235249 | TNFRSF1B | 0.037316 | −1.91972 | TC |
| rs1001293 | APOL2 | 0.041144 | −2.97129 | TC |
| rs1478290 | GYS2 | 0.041887 | 1.813052 | TG |
| rs891087 | INSR | 0.049589 | 2.676196 | AG |

Waist circumference

| SNP | Gene | p | Coeff. | Allele |
|---|---|---|---|---|
| rs8179183 | LEPR | 0.002406 | −8.06046 | CG |
| rs931490 | AGTR1 | 0.005809 | −7.88352 | AG |
| rs10841044 | PIK3C2G | 0.005846 | 7.001126 | TG |
| rs3791850 | GAD1 | 0.008186 | 6.255743 | TC |
| rs334555 | GSK3B | 0.009273 | 7.895669 | CG |
| rs2807071 | OAT | 0.009452 | −7.46654 | TC |
| rs1001293 | APOL2 | 0.009795 | −9.61956 | TC |
| rs705381 | PON1 | 0.01489 | −5.47129 | TC |
| rs6078 | LIPC | 0.022112 | −11.8435 | AG |
| rs10890819 | ACAT1 | 0.032828 | 4.590877 | TC |
| rs1611115 | DBH | 0.032976 | 5.301875 | TC |
| rs2076672 | APOL5 | 0.036192 | −3.70057 | TC |
| rs6837793 | NPY5R | 0.036679 | 7.097203 | AG |
| rs11212515 | ACAT1 | 0.038906 | 4.461923 | AT |
| rs5092 | APOA4 | 0.04185 | −5.51407 | AG |
| rs6136 | SELP | 0.047598 | 6.285743 | AC |

Metabolic Syndromes Index (MSI)

| SNP | Gene | p | Coeff. | Allele |
|---|---|---|---|---|
| rs2807071 | OAT | 0.000979 | −0.7058 | TC |
| rs7412 | APOE | 0.002457 | 0.923059 | TC |
| rs1935349 | HTR7 | 0.002612 | −0.66764 | AG |
| rs8179183 | LEPR | 0.002946 | −0.59432 | CG |
| rs1801282 | PPARG | 0.003285 | 0.68412 | CG |
| rs7247515 | AKT2 | 0.004808 | 0.695328 | TC |
| rs10513055 | PIK3CB | 0.007068 | −0.51604 | AC |
| rs11212515 | ACAT1 | 0.009036 | 0.421514 | AT |
| rs10890819 | ACAT1 | 0.011394 | 0.407459 | TC |
| rs3771892 | TNFAIP6 | 0.012464 | −0.47835 | AG |
| rs1046668 | TNFAIP6 | 0.012464 | −0.47835 | AG |
| rs4933200 | ANKRD1 | 0.013341 | −0.54664 | TC |
| rs6578993 | TH | 0.013485 | −0.50476 | TC |
| rs2241220 | ACACB | 0.013954 | 0.503461 | TC |
| rs1611115 | DBH | 0.018634 | 0.437048 | TC |
| rs132653 | APOL3 | 0.018979 | 0.450974 | AC |
| rs1049793 | ABP1 | 0.020195 | 0.36606 | GC |
| rs849404 | PIK3CG | 0.031332 | −0.43805 | AG |
| rs1001293 | APOL2 | 0.033894 | −0.59768 | TC |
| rs931490 | AGTR1 | 0.034987 | −0.4499 | AG |
| rs3758987 | HTR3B | 0.045451 | 0.358931 | AG |
| rs10934502 | GSK3B | 0.046833 | 0.370729 | TC |
| rs1433099 | LDLR | 0.049471 | 0.312369 | AG |

TABLE 6

Ziprasidone

| SNP | Gene | p | Coeff. | Allele |
|---|---|---|---|---|

Total Cholesterol

| SNP | Gene | p | Coeff. | Allele |
|---|---|---|---|---|
| rs6976017 | CYP3A5 | 6.84E−03 | −46.9421 | AG |
| rs6967107 | WBSCR14 | 1.12E−02 | −36.877 | AC |
| rs2856929 | PKM2 | 1.15E−02 | −25.5311 | AG |
| rs1415793 | ADORA3 | 1.43E−02 | −34.1892 | AG |
| rs737865 | TXNRD2 | 1.64E−02 | −20.8261 | TC |
| rs6700734 | TNFSF6 | 1.70E−02 | 22.61342 | AG |
| rs2228139 | IL1R1 | 2.46E−02 | −43.6237 | GC |
| rs2740574 | CYP3A4 | 3.20E−02 | −23.4693 | AG |
| rs1851426 | CYP3A4 | 3.20E−02 | −23.4693 | TC |
| rs2241220 | ACACB | 3.30E−02 | −23.3964 | TC |
| rs5085 | APOA2 | 3.72E−02 | 23.24462 | GC |
| rs762551 | CYP1A2 | 3.81E−02 | −20.3578 | AC |
| rs1322783 | DISC1 | 3.88E−02 | −25.9228 | TC |

LDL Cholesterol

| SNP | Gene | p | Coeff. | Allele |
|---|---|---|---|---|
| rs6976017 | CYP3A5 | 4.34E−03 | −45.408 | AG |
| rs2301108 | HIF1A | 4.60E−03 | 27.40929 | AG |
| rs6700734 | TNFSF6 | 1.15E−02 | 21.52701 | AG |
| rs1322783 | DISC1 | 1.26E−02 | −27.8566 | TC |
| rs2269935 | PFKM | 1.38E−02 | −29.0481 | AC |
| rs2228139 | IL1R1 | 1.74E−02 | −42.4134 | GC |
| rs10082776 | RARG | 1.92E−02 | −24.15 | AG |
| rs2856929 | PKM2 | 2.55E−02 | −21.0303 | AG |
| rs3816873 | MTP | 2.73E−02 | −19.1531 | TC |
| rs1951795 | HIF1A | 2.81E−02 | 17.20549 | AC |
| rs1614845 | HRH3 | 4.20E−02 | −21.1697 | TC |
| rs7816340 | ADRA1A | 4.22E−02 | 24.97225 | TC |
| rs2067477 | CHRM1 | 4.47E−02 | −23.7833 | AC |
| rs40318 | PIK3R1 | 4.80E−02 | 22.72104 | TC |
| rs6967107 | WBSCR14 | 5.00E−02 | −28.3763 | AC |

HDL Cholesterol

| SNP | Gene | p | Coeff. | Allele |
|---|---|---|---|---|
| rs4531 | DBH | 2.51E−03 | 18.09091 | TG |
| rs5369 | EDN1 | 4.90E−03 | 10.80675 | AG |
| rs5085 | APOA2 | 2.03E−02 | 8.153465 | GC |
| rs3757868 | ACHE | 2.11E−02 | 9.221154 | AG |
| rs722341 | ABCC8 | 2.50E−02 | 9.377622 | TC |
| rs10422283 | LIPE | 2.55E−02 | −7.84975 | TC |
| rs2070586 | DAO | 2.65E−02 | 7.543779 | AG |
| rs1001293 | APOL2 | 3.23E−02 | 9.575397 | TC |
| rs2228309 | FASN | 4.60E−02 | −5.10825 | TC |
| rs10841044 | PIK3C2G | 4.72E−02 | −8.0915 | TG |
| rs12691940 | HNMT | 4.73E−02 | 6.193487 | AG |

Triglycerides (TG) as log (TG)

| SNP | Gene | p | Coeff. | Allele |
|---|---|---|---|---|
| rs2807071 | OAT | 2.37E−03 | 0.580852 | TC |
| rs675 | APOA4 | 6.41E−03 | −0.49519 | TA |
| rs1801253 | ADRB1 | 9.61E−03 | 0.312206 | GC |
| rs6960931 | PRKAG2 | 1.49E−02 | −0.47605 | TC |
| rs748253 | FLT1 | 2.25E−02 | −0.25527 | TG |
| rs132661 | APOL3 | 2.48E−02 | 0.279847 | AG |
| rs2856929 | PKM2 | 2.62E−02 | −0.3179 | AG |
| rs167770 | DRD3 | 3.74E−02 | 0.232794 | AG |
| rs231460 | PYY | 3.78E−02 | 0.296538 | TC |

TABLE 6-continued

Ziprasidone

| SNP | Gene | p | Coeff. | Allele |
|---|---|---|---|---|
| rs1058046 | PYY | 3.79E−02 | 0.237088 | CG |
| rs6312 | HTR2A | 4.11E−02 | −0.47083 | AG |
| rs659734 | HTR2A | 4.11E−02 | −0.47083 | TC |
| rs10460960 | LOC391530 | 4.11E−02 | −0.24163 | AG |
| rs504714 | AVEN | 4.65E−02 | 0.409721 | AT |
| rs324651 | CHRM2 | 4.92E−02 | 0.357684 | TG |
| Ratio of Total Cholesterol to HDL Cholesterol |
| rs916829 | ABCC8 | 5.14E−03 | 1.186726 | TC |
| rs2856929 | PKM2 | 6.39E−03 | −0.85543 | AG |
| rs1322783 | DISC1 | 8.09E−03 | −1.01048 | TC |
| rs167770 | DRD3 | 9.33E−03 | 0.638128 | AG |
| rs8179183 | LEPR | 1.27E−02 | 0.960745 | CG |
| rs4072032 | PECAM1 | 1.41E−02 | 0.658682 | TC |
| rs3757868 | ACHE | 2.47E−02 | −0.88686 | AG |
| rs6700734 | TNFSF6 | 2.49E−02 | 0.657908 | AG |
| rs3822222 | CCKAR | 4.05E−02 | 0.874718 | TC |
| rs2070424 | SOD1 | 4.17E−02 | 1.129791 | AG |
| rs10509676 | CYP2C19 | 4.49E−02 | 0.649904 | TA |
| Blood Glucose Level |
| rs1801253 | ADRB1 | 8.35E−04 | 13.83333 | GC |
| rs235249 | TNFRSF1B | 8.16E−03 | 15.95833 | TC |
| rs1058167 | CYP2D6 | 1.54E−02 | 8.826899 | TC |
| rs1061622 | TNFRSF1B | 1.58E−02 | 11.71681 | TG |
| rs4531 | DBH | 2.56E−02 | 20.5 | TG |
| rs5369 | EDN1 | 2.75E−02 | 12.91429 | AG |
| rs3808607 | CYP7A1 | 3.01E−02 | −9.19403 | TG |
| rs6837793 | NPY5R | 3.02E−02 | 19.9375 | AG |
| rs2298191 | ADORA3 | 3.09E−02 | −10.3025 | TC |
| rs1041163 | VCAM1 | 3.58E−02 | −11.1318 | TC |
| rs3917550 | PON1 | 3.73E−02 | −11.6657 | TC |
| rs295 | LPL | 4.20E−02 | 11.02703 | AC |
| rs5950584 | LOC441514 | 4.27E−02 | 10.80208 | TG |
| rs3024492 | IL10 | 4.75E−02 | −8.93506 | TA |
| rs2429511 | ADRB1 | 4.88E−02 | −8.05488 | AG |
| Systolic Blood Pressure |
| rs5880 | CETP | 2.01E−03 | 15.23378 | CG |
| rs26312 | GHRL | 4.59E−03 | 11.01497 | AG |
| rs324651 | CHRM2 | 6.74E−03 | 10.68624 | TG |
| rs2076672 | APOL5 | 6.81E−03 | 5.923627 | TC |
| rs3791981 | APOB | 9.54E−03 | 13.0392 | AG |
| rs2856929 | PKM2 | 1.10E−02 | −7.99528 | AG |
| rs2067477 | CHRM1 | 1.15E−02 | 9.930635 | AC |
| rs7641983 | PIK3CA | 2.01E−02 | −10.2652 | TC |
| rs4727666 | PIK3CG | 2.69E−02 | 6.511042 | AG |
| rs504714 | AVEN | 2.84E−02 | 9.966639 | AT |
| rs931992 | TCAP | 2.93E−02 | −7.16129 | AC |
| rs1029947 | PRKAG2 | 3.07E−02 | −8.11197 | AG |
| rs107540 | CRHR2 | 4.55E−02 | −7.54295 | AG |
| rs10422283 | LIPE | 4.90E−02 | 6.837915 | TC |
| Diastolic Blood Pressure |
| rs4765623 | SCARB1 | 6.14E−03 | −5.49732 | TC |
| rs2067477 | CHRM1 | 6.54E−03 | 8.222796 | AC |
| rs324651 | CHRM2 | 6.88E−03 | 8.257257 | TG |
| rs1799821 | CPT2 | 7.25E−03 | −6.04121 | AG |
| rs2269935 | PFKM | 1.16E−02 | 7.767091 | AC |
| rs2228502 | CPT1A | 1.90E−02 | −10.9398 | TC |
| rs334555 | GSK3B | 1.93E−02 | 5.925818 | CG |
| rs1801253 | ADRB1 | 2.06E−02 | 4.849245 | GC |
| rs903361 | ADORA1 | 2.36E−02 | −5.14973 | TC |
| rs2867383 | DRD5 | 2.45E−02 | −5.50902 | AG |
| rs3816873 | MTP | 2.72E−02 | 5.006082 | TC |
| rs5880 | CETP | 3.17E−02 | 8.494969 | CG |
| rs1800783 | NOS3 | 3.89E−02 | 3.772508 | TA |
| rs8178990 | CHAT | 4.68E−02 | −12.8796 | TC |
| Body Mass |
| rs324651 | CHRM2 | 6.49E−05 | 29.85233 | TG |
| rs1468271 | NPY | 2.85E−04 | 79.76806 | AG |
| rs5927 | LDLR | 1.54E−03 | −18.167 | AG |
| rs600728 | TEK | 2.70E−03 | 28.09976 | AG |
| rs1283718 | ANGPT1 | 8.61E−03 | 28.60813 | TG |
| rs3756450 | SLC6A3 | 1.26E−02 | 17.35732 | TC |
| rs1433099 | LDLR | 1.78E−02 | −14.2532 | AG |
| rs4765623 | SCARB1 | 1.95E−02 | −12.3335 | TC |
| rs6196 | NR3C1 | 2.04E−02 | −16.2114 | AG |
| rs2807071 | OAT | 2.82E−02 | 19.32361 | TC |
| rs2856929 | PKM2 | 2.90E−02 | −13.9615 | AG |
| rs1800808 | SELP | 3.27E−02 | 19.55321 | TC |
| rs10513055 | PIK3CB | 3.29E−02 | −19.6168 | AC |
| rs439401 | APOE | 3.96E−02 | −11.489 | TC |
| rs1438732 | NR3C1 | 4.38E−02 | −14.2465 | CG |
| rs936960 | LIPC | 4.41E−02 | 17.82599 | AC |
| Body Mass Index |
| rs324651 | CHRM2 | 1.36E−03 | 7.184667 | TG |
| rs439401 | APOE | 3.90E−03 | −4.51994 | TC |
| rs5927 | LDLR | 5.46E−03 | −4.67645 | AG |
| rs1468271 | NPY | 7.80E−03 | 17.61389 | AG |
| rs6196 | NR3C1 | 9.21E−03 | −5.20455 | AG |
| rs936960 | LIPC | 9.27E−03 | 6.525 | AC |
| rs3756450 | SLC6A3 | 1.03E−02 | 5.141667 | TC |
| rs405509 | APOE | 1.04E−02 | −3.78462 | AC |
| rs1438732 | NR3C1 | 1.18E−02 | −5.05443 | CG |
| rs2807071 | OAT | 1.83E−02 | 5.967064 | TC |
| rs3750546 | RXRA | 2.12E−02 | −3.99209 | AG |
| rs1283718 | ANGPT1 | 2.21E−02 | 7.281875 | TG |
| rs2742115 | OLR1 | 2.64E−02 | 4.045918 | AG |
| rs600728 | TEK | 3.14E−02 | 6.001905 | AG |
| rs2125489 | KDR | 3.30E−02 | −6.32043 | TC |
| rs235249 | TNFRSF1B | 3.40E−02 | 4.952333 | TC |
| rs2856929 | PKM2 | 3.42E−02 | −3.91925 | AG |
| rs2229126 | ADRA1A | 3.79E−02 | 14.01667 | AT |
| rs1061622 | TNFRSF1B | 4.06E−02 | 3.828298 | TG |
| rs1801253 | ADRB1 | 4.76E−02 | 3.140701 | GC |
| rs10508244 | PFKP | 4.83E−02 | −5.8828 | TC |
| rs5092 | APOA4 | 4.84E−02 | 3.623061 | AG |
| Waist circumference |
| rs324651 | CHRM2 | 2.03E−03 | 16.16883 | TG |
| rs6196 | NR3C1 | 5.87E−03 | −12.7097 | AG |
| rs5491 | ICAM1 | 1.36E−02 | −17.2978 | AT |
| rs894251 | SCARB2 | 1.54E−02 | −14.2088 | TC |
| rs1871143 | GYS2 | 2.10E−02 | −9.1324 | TG |
| rs1951795 | HIF1A | 2.25E−02 | −8.11175 | AC |
| rs10515521 | NR3C1 | 2.69E−02 | −15.2101 | AG |
| rs4762 | AGT | 2.74E−02 | −13.5825 | TC |
| rs1438732 | NR3C1 | 2.89E−02 | −10.3014 | CG |
| rs1801253 | ADRB1 | 3.04E−02 | 7.934166 | GC |
| rs2301108 | HIF1A | 3.61E−02 | −9.46431 | AG |
| rs140700 | SLC6A4 | 3.73E−02 | −23.4298 | AG |
| rs4726107 | LOC441301 | 3.81E−02 | −14.7148 | TC |
| rs2269935 | PFKM | 3.91E−02 | 11.21882 | AC |
| rs1800783 | NOS3 | 3.91E−02 | 6.564373 | TA |
| rs2125489 | KDR | 4.39E−02 | −13.9371 | TC |
| rs5927 | LDLR | 4.49E−02 | −8.05176 | AG |
| rs2856929 | PKM2 | 4.76E−02 | −8.55473 | AG |
| rs1283718 | ANGPT1 | 4.99E−02 | 14.64448 | TG |
| Metabloic Syndrome Index (MSI) |
| rs324651 | CHRM2 | 1.81E−04 | 1.447605 | TG |
| rs1801253 | ADRB1 | 6.00E−04 | 0.910939 | GC |
| rs2856929 | PKM2 | 4.15E−03 | −0.91353 | AG |
| rs2125489 | KDR | 8.27E−03 | −1.36095 | TC |
| rs1800783 | NOS3 | 8.99E−03 | 0.62109 | TA |
| rs2429511 | ADRB1 | 1.10E−02 | −0.67981 | AG |
| rs11568728 | CYP2D6 | 1.88E−02 | 0.728924 | AG |
| rs2070424 | SOD1 | 2.06E−02 | 1.30091 | AG |
| rs1877394 | PIK3C2B | 2.23E−02 | −2.71011 | AG |
| rs2807071 | OAT | 2.41E−02 | 1.012098 | TC |
| rs1356413 | PIK3CA | 2.77E−02 | 0.932247 | GC |
| rs619698 | SSTR5 | 3.02E−02 | 0.510918 | AC |
| rs2228502 | CPT1A | 3.10E−02 | −1.34148 | TC |
| rs4072032 | PECAM1 | 3.34E−02 | 0.589433 | TC |
| rs894251 | SCARB2 | 3.46E−02 | −0.95221 | TC |
| rs504714 | AVEN | 4.12E−02 | 0.95686 | AT |
| rs4765623 | SCARB1 | 4.56E−02 | −0.54475 | TC |
| rs6196 | NR3C1 | 4.81E−02 | −0.69664 | AG |

TABLE 7

| SNP | Gene | p | Coeff. | Allele |
|---|---|---|---|---|
| Drug Class | | | | |
| Total Cholesterol | | | | |
| rs3816873 | MTP | 0.002358 | −11.5156 | TC |
| rs2125489 | KDR | 0.003458 | 16.32529 | TC |
| rs3756450 | SLC6A3 | 0.008782 | 10.84155 | TC |
| rs9659997 | HTR6 | 0.01024 | 9.063308 | TC |
| rs2228502 | CPT1A | 0.012943 | 16.55381 | TC |
| rs4149056 | SLCO1B1 | 0.020066 | −7.95964 | TC |
| rs849404 | PIK3CG | 0.022662 | 11.11702 | AG |
| rs2298122 | DRD1IP | 0.022958 | −8.7104 | TG |
| rs3791981 | APOB | 0.025096 | 9.922727 | AG |
| rs6967107 | WBSCR14 | 0.028595 | −12.6042 | AC |
| rs4646450 | CYP3A5 | 0.028627 | −7.59158 | TC |
| rs429358 | APOE | 0.029953 | 9.965427 | TC |
| rs5368 | SELE | 0.040002 | 11.01929 | TC |
| rs6700734 | TNFSF6 | 0.04529 | 7.517918 | AG |
| rs2228139 | IL1R1 | 0.048307 | −11.8786 | GC |
| LDL Cholesterol | | | | |
| rs686874 | HRH2 | 0.00355 | 15.2072 | TC |
| rs2125489 | KDR | 0.007167 | 11.95727 | TC |
| rs3791981 | APOB | 0.007775 | 9.402099 | AG |
| rs3756450 | SLC6A3 | 0.009712 | 8.640275 | TC |
| rs2228502 | CPT1A | 0.01202 | 13.54827 | TC |
| rs6700734 | TNFSF6 | 0.014509 | 7.303434 | AG |
| rs3816873 | MTP | 0.019158 | −7.09744 | TC |
| rs6967107 | WBSCR14 | 0.022653 | −11.0704 | AC |
| rs7412 | APOE | 0.029002 | −8.49832 | TC |
| rs5030390 | ICAM1 | 0.030029 | −9.62556 | AG |
| rs1176744 | HTR3B | 0.031983 | 5.200979 | TG |
| rs1468271 | NPY | 0.036079 | 14.30161 | AG |
| rs1049793 | ABP1 | 0.036682 | −5.54658 | GC |
| rs745075 | MTP | 0.037089 | −9.64542 | AG |
| rs264 | LPL | 0.040193 | −7.16211 | AG |
| rs2298122 | DRD1IP | 0.040437 | −6.27851 | TG |
| rs5368 | SELE | 0.041124 | 8.769493 | TC |
| rs1045642 | ABCB1 | 0.044412 | −5.01533 | TC |
| rs908867 | BDNF | 0.044442 | −8.78483 | AG |
| rs2856929 | PKM2 | 0.044462 | −6.01823 | AG |
| rs40318 | PIK3R1 | 0.048052 | 7.691795 | TC |
| rs3808607 | CYP7A1 | 0.049216 | 5.280183 | TG |
| HDL Cholesterol | | | | |
| rs7072137 | GAD2 | 0.000317 | 5.889298 | AG |
| rs4727666 | PIK3CG | 0.000697 | 3.885888 | AG |
| rs10890819 | ACAT1 | 0.000832 | −3.67111 | TC |
| rs1935349 | HTR7 | 0.001205 | 4.088468 | AG |
| rs849404 | PIK3CG | 0.001538 | 4.90131 | AG |
| rs1057910 | CYP2C9 | 0.001876 | −3.59452 | AC |
| rs11212515 | ACAT1 | 0.002337 | −3.32614 | AT |
| rs701492 | GAD1 | 0.002378 | 4.165665 | TC |
| rs1532624 | CETP | 0.002506 | 3.137294 | TG |
| rs3764261 | CETP | 0.004457 | 3.253212 | TG |
| rs711752 | CETP | 0.005173 | 2.94954 | AG |
| rs264 | LPL | 0.005375 | 3.871475 | AG |
| rs4646458 | CYP3A5 | 0.005481 | 5.254293 | AC |
| rs826082 | UCP3 | 0.005557 | 4.583308 | TA |
| rs2076672 | APOL5 | 0.007275 | −2.50753 | TC |
| rs814628 | LIPF | 0.010282 | −3.38191 | AG |
| rs4933200 | ANKRD1 | 0.011763 | 3.219459 | TC |
| rs4301822 | APOF | 0.012139 | 4.433299 | TC |
| rs2298191 | ADORA3 | 0.012894 | −2.77504 | TC |
| rs10515521 | NR3C1 | 0.015161 | 3.47137 | AG |
| rs4646450 | CYP3A5 | 0.017436 | 2.623565 | TC |
| rs2162189 | SST | 0.017808 | 3.318663 | AG |
| rs2192752 | IL1R1 | 0.01881 | −3.08108 | AC |
| rs3842726 | TH | 0.020049 | 4.703695 | CG |
| rs2020933 | SLC6A4 | 0.020986 | 3.83513 | AT |
| rs5880 | CETP | 0.021397 | −4.55368 | CG |
| rs3771892 | TNFAIP6 | 0.021861 | 3.309755 | AG |
| rs1396862 | CRHR1 | 0.021939 | −3.16076 | TC |
| rs2742115 | OLR1 | 0.021969 | −2.69948 | AG |
| rs1046668 | TNFAIP6 | 0.023331 | 3.191831 | AG |
| rs916829 | ABCC8 | 0.024865 | −3.64832 | TC |
| rs1438732 | NR3C1 | 0.026286 | −3.01006 | CG |
| rs2227852 | DRD5 | 0.030625 | 4.091046 | AG |
| rs136163 | APOL1 | 0.031169 | 2.411966 | TG |
| rs1143634 | IL1B | 0.031207 | −2.59194 | TC |
| rs4802071 | AKT2 | 0.031336 | −1.96513 | TC |
| rs776746 | CYP3A5 | 0.031521 | 2.774078 | AG |
| rs12333983 | CYP3A4 | 0.03187 | 2.64483 | TA |
| rs40318 | PIK3R1 | 0.03322 | −3.29153 | TC |
| rs1801282 | PPARG | 0.033242 | −3.4473 | CG |
| rs1468271 | NPY | 0.034544 | −5.77009 | AG |
| rs167771 | DRD3 | 0.035166 | 2.331589 | AG |
| rs6489738 | GNB3 | 0.03597 | 2.078931 | TC |
| rs676643 | HTR1D | 0.037571 | −2.7865 | AG |
| rs461404 | PRKAA1 | 0.038144 | 2.273432 | TC |
| rs6032470 | GHRH | 0.03875 | 2.553331 | TC |
| rs3176921 | CRH | 0.047842 | 2.33487 | TC |
| rs1951795 | HIF1A | 0.048917 | 2.067027 | AC |
| Triglycerides (TG) as log (TG) | | | | |
| rs2838549 | PFKL | 0.008363 | −0.13627 | AG |
| rs6078 | LIPC | 0.008616 | 0.286858 | AG |
| rs686874 | HRH2 | 0.00922 | −0.21314 | TC |
| rs4646450 | CYP3A5 | 0.009405 | −0.11203 | TC |
| rs3791850 | GAD1 | 0.010643 | 0.123579 | TC |
| rs11188092 | CYP2C19 | 0.02542 | −0.11702 | AC |
| rs2229169 | ADRA2B | 0.028696 | 0.095306 | AC |
| rs10890819 | ACAT1 | 0.028847 | 0.094357 | TC |
| rs2292459 | PIK3C2B | 0.033313 | −0.22579 | TC |
| rs4333 | ACE | 0.034898 | 0.085601 | TC |
| rs10460960 | LOC391530 | 0.035916 | −0.09318 | AG |
| rs11212515 | ACAT1 | 0.036578 | 0.089865 | AT |
| rs7072137 | GAD2 | 0.036658 | −0.13589 | AG |
| rs3756007 | GABRA2 | 0.040299 | 0.193943 | TC |
| rs2276307 | HTR3B | 0.0444 | 0.098571 | AG |
| Ratio of Total Cholesterol to HDL Cholesterol | | | | |
| rs3756450 | SLC6A3 | 0.000857 | 0.404097 | TC |
| rs10890819 | ACAT1 | 0.000993 | 0.33343 | TC |
| rs11212515 | ACAT1 | 0.001265 | 0.324802 | AT |
| rs264 | LPL | 0.005348 | −0.357 | AG |
| rs2228502 | CPT1A | 0.009231 | 0.508518 | TC |
| rs916829 | ABCC8 | 0.011091 | 0.380539 | TC |
| rs701492 | GAD1 | 0.014455 | −0.3157 | TC |
| rs7072137 | GAD2 | 0.016128 | −0.36665 | AG |
| rs1468271 | NPY | 0.019107 | 0.588927 | AG |
| rs4646450 | CYP3A5 | 0.019917 | −0.2369 | TC |
| rs1532624 | CETP | 0.020927 | −0.22249 | TG |
| rs711752 | CETP | 0.022459 | −0.22264 | AG |
| rs6586179 | LIPA | 0.024978 | 0.344192 | TC |
| rs3762272 | PKLR | 0.02591 | 0.988226 | AG |
| rs1801282 | PPARG | 0.028577 | 0.326612 | CG |
| rs6809631 | PPARG | 0.028839 | 0.232461 | AT |
| rs2301108 | HIF1A | 0.029147 | 0.268533 | AG |
| rs5369 | EDN1 | 0.034961 | −0.29478 | AG |
| rs3816873 | MTP | 0.04139 | −0.2276 | TC |
| rs3764261 | CETP | 0.043853 | −0.21314 | TG |
| rs1935349 | HTR7 | 0.048724 | −0.23048 | AG |
| rs854572 | PON1 | 0.049032 | 0.175421 | CG |
| Blood Glucose Level | | | | |
| rs3176921 | CRH | 0.000106 | 6.664646 | TC |
| rs2241220 | ACACB | 0.00049 | 6.770076 | TC |
| rs2229126 | ADRA1A | 0.001594 | 15.58602 | AT |
| rs3842726 | TH | 0.002167 | 9.356469 | CG |
| rs446037 | APOE | 0.00896 | 19.25842 | AC |
| rs877172 | OXT | 0.014921 | 3.749715 | AC |
| rs1049793 | ABP1 | 0.017893 | 3.627758 | GC |
| rs5742612 | IGF1 | 0.018395 | 10.2451 | TC |
| rs659734 | HTR2A | 0.020969 | 7.11232 | TC |
| rs1440451 | HTR5A | 0.021173 | 6.642692 | CG |
| rs10494851 | PIK3C2B | 0.024342 | 12.82075 | AG |
| rs2162189 | SST | 0.030039 | 4.39572 | AG |
| rs6578993 | TH | 0.030905 | −4.59916 | TC |
| rs1058167 | CYP2D6 | 0.03843 | 2.940465 | TC |
| rs3813065 | PIK3C3 | 0.039425 | 4.017745 | TC |
| rs1801278 | IRS1 | 0.04342 | 5.524347 | AG |
| rs2240403 | CRHR2 | 0.045209 | −5.01437 | TC |
| rs563895 | AVEN | 0.046231 | 3.554641 | TC |

TABLE 7-continued

Drug Class

| SNP | Gene | p | Coeff. | Allele |
|---|---|---|---|---|
| rs10934502 | GSK3B | 0.047825 | 3.539527 | TC |
| rs6489738 | GNB3 | 0.048332 | 2.839347 | TC |
| rs4121817 | PIK3C3 | 0.049505 | 3.899782 | AG |
| Systolic Blood Pressure | | | | |
| rs4784642 | GNAO1 | 0.004862 | −2.41132 | AG |
| rs3853188 | SCARB2 | 0.015086 | 3.688517 | AC |
| rs707922 | APOM | 0.017685 | 3.212498 | AC |
| rs1556478 | LIPA | 0.02222 | 1.988161 | AG |
| rs4301822 | APOF | 0.023463 | 3.352318 | TC |
| rs10846744 | SCARB1 | 0.025452 | 2.29167 | CG |
| rs3847063 | ACHE | 0.027587 | −1.79576 | AG |
| rs1800206 | PPARA | 0.030135 | −4.07895 | GC |
| rs1001293 | APOL2 | 0.034602 | 2.752037 | TC |
| rs931992 | TCAP | 0.034776 | −1.75114 | AC |
| rs2740574 | CYP3A4 | 0.034874 | 2.589535 | AG |
| rs5880 | CETP | 0.037434 | 3.461357 | CG |
| rs2515449 | MCPH1 | 0.037743 | −3.33185 | AG |
| rs748253 | FLT1 | 0.043454 | 1.764121 | TG |
| rs1143634 | IL1B | 0.043686 | −2.03033 | TC |
| rs1800794 | IL1A | 0.049068 | −1.88267 | TC |
| Diastolic Blood Pressure | | | | |
| rs2229169 | ADRA2B | 0.000601 | 2.358133 | AC |
| rs2287754 | GYS1 | 0.001047 | −4.00044 | AG |
| rs1801253 | ADRB1 | 0.00193 | 2.229732 | GC |
| rs707922 | APOM | 0.002646 | 3.016561 | AC |
| rs931992 | TCAP | 0.022886 | −1.3987 | AC |
| rs711752 | CETP | 0.024168 | 1.478059 | AG |
| rs1800794 | IL1A | 0.026831 | −1.5697 | TC |
| rs1532624 | CETP | 0.028195 | 1.426516 | TG |
| rs4784642 | GNAO1 | 0.030391 | −1.3773 | AG |
| rs5742612 | IGF1 | 0.031605 | 3.957474 | TC |
| rs11632618 | LIPC | 0.031833 | −2.90693 | AG |
| rs10513055 | PIK3CB | 0.032316 | −1.8368 | AC |
| rs5070 | APOA1 | 0.034801 | 1.390141 | AG |
| rs4688046 | GSK3B | 0.034978 | 1.678459 | TC |
| rs10934502 | GSK3B | 0.036827 | 1.604019 | TC |
| rs936960 | LIPC | 0.037146 | −2.14186 | AC |
| rs2033447 | RARB | 0.039626 | −1.6278 | TC |
| rs3769671 | POMC | 0.041005 | −3.76597 | AC |
| rs6578993 | TH | 0.048468 | −1.80869 | TC |
| Body Mass | | | | |
| rs10934502 | GSK3B | 0.003641 | 5.479386 | TC |
| rs4890109 | RARA | 0.007977 | −11.9733 | TG |
| rs405509 | APOE | 0.008111 | −4.0616 | AC |
| rs4688046 | GSK3B | 0.008866 | 5.078073 | TC |
| rs1356413 | PIK3CA | 0.010924 | 8.181701 | GC |
| rs2429511 | ADRB1 | 0.012499 | −3.77327 | AG |
| rs4802071 | AKT2 | 0.012763 | −3.50489 | TC |
| rs1190762 | GNAO1 | 0.012933 | 7.006901 | AC |
| rs3853188 | SCARB2 | 0.017827 | 6.596256 | AC |
| rs3760396 | CCL2 | 0.018069 | 4.642731 | GC |
| rs676643 | HTR1D | 0.020292 | 4.7413 | AG |
| rs3810947 | CHAT | 0.020345 | 5.230027 | AG |
| rs619698 | SSTR5 | 0.021703 | 3.810354 | AC |
| rs6032470 | GHRH | 0.022168 | 4.312747 | TC |
| rs1801253 | ADRB1 | 0.022625 | 4.044925 | GC |
| rs854572 | PON1 | 0.024727 | 3.316257 | CG |
| rs2515449 | MCPH1 | 0.026692 | −6.4646 | AG |
| rs4784642 | GNAO1 | 0.030202 | −3.40857 | AG |
| rs7412 | APOE | 0.031427 | 5.090636 | TC |
| rs7556371 | PIK3C2B | 0.034553 | 3.375996 | AG |
| rs3771892 | TNFAIP6 | 0.035215 | −4.66373 | AG |
| rs324651 | CHRM2 | 0.035746 | 4.983706 | TG |
| rs504714 | AVEN | 0.03577 | 5.794365 | AT |
| rs833060 | VEGF | 0.035795 | −3.80789 | TG |
| rs903361 | ADORA1 | 0.036013 | 3.421146 | TC |
| rs439401 | APOE | 0.037343 | −3.28745 | TC |
| rs132653 | APOL3 | 0.037557 | 4.204654 | AC |
| rs10082776 | RARG | 0.044948 | 4.261507 | AG |
| rs235249 | TNFRSF1B | 0.04654 | −3.5051 | TC |
| rs1046668 | TNFAIP6 | 0.047938 | −4.25817 | AG |

TABLE 7-continued

Drug Class

| SNP | Gene | p | Coeff. | Allele |
|---|---|---|---|---|
| Body Mass Index | | | | |
| rs619698 | SSTR5 | 0.000276 | 1.888092 | AC |
| rs3853188 | SCARB2 | 0.006329 | 2.386221 | AC |
| rs1801253 | ADRB1 | 0.008532 | 1.470889 | GC |
| rs2515449 | MCPH1 | 0.009148 | −2.40175 | AG |
| rs5896 | F2 | 0.010941 | 2.071369 | TC |
| rs405509 | APOE | 0.012524 | −1.21019 | AC |
| rs10934502 | GSK3B | 0.012676 | 1.4867 | TC |
| rs4890109 | RARA | 0.016631 | −3.42259 | TG |
| rs3760396 | CCL2 | 0.017789 | 1.467532 | GC |
| rs1356413 | PIK3CA | 0.019681 | 2.352268 | GC |
| rs3810947 | CHAT | 0.019918 | 1.660325 | AG |
| rs4784642 | GNAO1 | 0.024029 | −1.11783 | AG |
| rs1355920 | CHRNA7 | 0.026455 | 1.543432 | AG |
| rs885834 | CHAT | 0.028301 | 1.039369 | AG |
| rs10515070 | PIK3R1 | 0.032285 | 1.164202 | AT |
| rs4688046 | GSK3B | 0.034848 | 1.299963 | TC |
| rs5092 | APOA4 | 0.035858 | −1.32647 | AG |
| rs2429511 | ADRB1 | 0.036514 | −0.99896 | AG |
| rs1058046 | PYY | 0.038132 | 1.00792 | CG |
| rs3842726 | TH | 0.038372 | 2.010312 | CG |
| rs10513055 | PIK3CB | 0.039359 | −1.34514 | AC |
| rs6032470 | GHRH | 0.040926 | 1.217706 | TC |
| rs2740574 | CYP3A4 | 0.041286 | 1.444238 | AG |
| rs1549758 | NOS3 | 0.042201 | 1.120038 | TC |
| Waist circumference | | | | |
| rs2515449 | MCPH1 | 0.001853 | −7.0002 | AG |
| rs1356413 | PIK3CA | 0.002401 | 7.455618 | GC |
| rs619698 | SSTR5 | 0.0026 | 3.877905 | AC |
| rs10934502 | GSK3B | 0.006136 | 4.042208 | TC |
| rs4688046 | GSK3B | 0.008254 | 3.995048 | TC |
| rs4890109 | RARA | 0.008912 | −9.12914 | TG |
| rs2071521 | APOC3 | 0.012697 | −2.90581 | TC |
| rs7412 | APOE | 0.013699 | 4.489459 | TC |
| rs4784642 | GNAO1 | 0.015525 | −2.94036 | AG |
| rs1058046 | PYY | 0.016638 | 2.825047 | CG |
| rs5092 | APOA4 | 0.019169 | −3.62226 | AG |
| rs5896 | F2 | 0.020655 | 4.656972 | TC |
| rs6196 | NR3C1 | 0.025789 | −3.56383 | AG |
| rs5742612 | IGF1 | 0.025861 | 7.734528 | TC |
| rs324651 | CHRM2 | 0.028224 | 4.025291 | TG |
| rs405509 | APOE | 0.030493 | −2.57422 | AC |
| rs231460 | PYY | 0.031009 | 3.152169 | TC |
| rs1438271 | NR3C1 | 0.035337 | −3.36893 | CG |
| rs140700 | SLC6A4 | 0.038852 | −4.56659 | AG |
| rs8179183 | LEPR | 0.040078 | −3.22459 | CG |
| rs132653 | APOL3 | 0.041055 | 3.234938 | AC |
| rs707922 | APOM | 0.044765 | −3.83538 | AC |
| rs7975375 | ADIPOR2 | 0.048017 | 2.547379 | TC |
| rs3024492 | IL10 | 0.049687 | −2.677 | TA |
| Metabolic Syndromes Index (MSI) | | | | |
| rs2515449 | MCPH1 | 0.001536 | −0.53679 | AG |
| rs619698 | SSTR5 | 0.004279 | 0.273064 | AC |
| rs5742612 | IGF1 | 0.004624 | 0.742662 | TC |
| rs10934502 | GSK3B | 0.006778 | 0.297499 | TC |
| rs10890819 | ACAT1 | 0.007428 | 0.26217 | TC |
| rs10513055 | PIK3CB | 0.0082 | −0.32027 | AC |
| rs11212515 | ACAT1 | 0.008419 | 0.256723 | AT |
| rs686874 | HRH2 | 0.010989 | −0.47356 | TC |
| rs7072137 | GAD2 | 0.012045 | −0.36967 | AG |
| rs3846662 | HMGCR | 0.015441 | 0.210518 | TC |
| rs854572 | PON1 | 0.019329 | 0.200947 | CG |
| rs4792887 | CRHR1 | 0.023634 | −0.29535 | TC |
| rs4784642 | GNAO1 | 0.026101 | −0.20314 | AG |
| rs1935349 | HTR7 | 0.026764 | −0.24965 | AG |
| rs8179183 | LEPR | 0.031001 | −0.25013 | CG |
| rs2429511 | ADRB1 | 0.031121 | −0.18982 | AG |
| rs2229169 | ADRA2B | 0.033172 | 0.210899 | AC |
| rs4688046 | GSK3B | 0.035201 | 0.236128 | TC |
| rs1468271 | NPY | 0.037455 | 0.505009 | AG |
| rs1046668 | TNFAIP6 | 0.037524 | −0.26038 | AG |
| rs2742115 | OLR1 | 0.040169 | 0.215112 | AG |

TABLE 7-continued

| | Drug Class | | | |
|---|---|---|---|---|
| SNP | Gene | p | Coeff. | Allele |
| rs3771892 | TNFAIP6 | 0.042269 | −0.26163 | AG |
| rs1356413 | PIK3CA | 0.04352 | 0.374351 | GC |

Example 2

In the SNP screen (step 2), the p-values for each SNP were obtained by adding the SNP to the covariate model and comparing the resulting model improvement with up to 10,000 simulated model improvements using the same data set, but with the genotype data randomly permuted to remove any true association. This method produces a p-value that is a direct, unbiased, and model-free estimate of the probability of finding a model as good as the one tested when the null hypothesis of no association is true. All SNPs with a screening p-value of better than 0.003 were selected to be included in the physiogenomic model (step 3).

Data Analysis. Covariates were analyzed using multiple linear regression and the stepwise procedure. An extended linear model was constructed including the significant covariate and the SNP genotype. SNP genotype was coded quantitatively as a numerical variable indicating the number of minor alleles: 0 for major homozygotes, 1 for heterozygotes, and 2 for minor homozygotes. The F-statistic p-value for the SNP variable was used to evaluate the significance of association. The validity of the p-values were tested by performance of an independent calculation of the p-values using permutation testing. To account for the multiple testing of multiple SNPs, adjusted p-values were calculated using Benjamini and Hochbergs false discovery rate (FDR) procedure [Reinere A, Yekutiele D, Benjamini Y: Identifying differentially expressed genes using false discovery rate controlling procedures. Bioinformatics 19:368-375 (2003); Benjamini Y, Hochberg Y: Controlling the false discovery rate: a practical and powerful approach to multiple testing. Journal of the Royal Statistical Society, Series B 57:289-300 (1995); Benjamini Y, Hochberg Y: On the adaptive control of the false discovery rate in multiple testing with independent statistics. Journal of Educational and Behavioral Statistics 25:60-83 (2000)]. In addition, the power for detecting an association based on the Bonferroni multiple comparison adjustment was evaluated. For each SNP, the effect size in standard deviations that was necessary for detection of an association at a power of 80% (20% false negative rate) was calculated using the formula:

$$\Delta = \frac{z_{\alpha/c} + z_{\beta}}{\sqrt{Nf(1-f)}}$$

where α was the desired false positive rate (α=0.05), β the false negative rate (β=1−Power=0.2), c the number of SNPs, z a standard normal deviate, N the number of subjects, f the carrier proportion, and Δ the difference in change in response between carriers and non-carriers expressed relative to the standard deviation [Rosner B: Fundamentals of Biostatistics. Belmont, Calif.: Wadsworth Publishing Co. (1995).].

LOESS representation. A locally smoothed function of the SNP frequency as it varies with each response was used to visually represent the nature of an association. LOESS (LOcally wEighted Scatter plot Smooth) is a method to smooth data using a locally weighted linear regression [Cleveland, WS: Robust locally weighted regression and smoothing scatterplots. *Journal of American Statistical Association* 74, 829-836 (1979); Cleveland W S, Devlin S J: Locally Weighted Regression: An Approach to Regression Analysis by Local Fitting. *Journal of the American Statistical Association* Vol. 83, pp. 596-610 (1988)]. At each point in the LOESS curve, a quadratic polynomial was fitted to the data in the vicinity of that point. The data were weighted such that they contributed less if they were further away, according to the following tricubic function where x was the abscissa of the point to be estimated, the $x_i$ were the data points in the vicinity, and d(x) was the maximum distance of x to the $x_i$.

$$w_i = \left(1 - \left|\frac{x - x_i}{d(x)}\right|^3\right)^3$$

The distribution of change in each parameter in the study population are approximately normal. The potential covariates of age, gender, race, are tested for association with each parameter using multiple linear regression. The LOESS curve will show the localized frequency of the least common allele for sectors of the distribution. For SNPs with a strong association, the marker frequency is significantly different between the high end and the low end of the distribution. Conversely, if a marker is neutral, the frequency is independent of the response and the LOESS curve is essentially flat.

If an allele is more common among patients with high response than among those with low response, the allele is likely to be associated with increased response. Similarly, when the allele is less common in those with high response, the allele is associated with decreased response. Thus, the slope of the curve is an indication of the degree of association.

a. Data analysis. The objective of the statistical analysis is to find a set of physiogenomic factors that together provide a way of predicting the outcome of interest. The association of an individual factor with the outcome may not have sufficient discrimination ability to provide the necessary sensitivity and specificity, but by combining the effect of several such factors the objective is reached. Increased sensitivity and specificity for the cumulative effect on prediction can be achieved through the use of common factors that are statistically independent. The assumptions on which these calculations are based are (a) the factors are independent of each other, (b) the association between each factor and the outcome can be summarized by a modest odds ratio of 1.7, and (c) the prevalence of each physiogenomic factor in the population is 50% and independent of the others. Clearly, the prediction becomes even stronger if the association with the response is stronger or one finds additional predictors. However, factors that are less useful for these types of prediction are those that are less common in the population, or collinear with factors that have already been identified in the prediction model.

b. Model Building. Discovery of markers affecting metabolic syndromes in response to psychotropic drugs. A model was developed for the purpose of predicting a given response (Y) to psychotropic drugs. A linear model for subjects in a group of patients subjected to psychotropic drugs was used in which the response of interest can be expressed as follows:

$$Y = R_0 + \sum_i \alpha_i M_i + \sum_j \beta_j D_j + \varepsilon$$

where $M_i$ are the dummy marker variables indicating the presence of specified genotypes and $D_j$ are demographic and clinical covariates. The model parameters that are to be estimated from the data are $R_0$, $\alpha_i$ and $\beta_j$. This model employs standard regression techniques that enable the systematic search for the best predictors. S-plus provides very good support for algorithms that provide these estimates for the initial linear regression models, as well other generalized linear models that may be used when the error distribution is not normal. For continuous variables, generalized additive models, including cubic splines in order to appropriately assess the form for the dose-response relationship may also be considered [Hastie T, Tibshirani R. Generalized additive models. *Stat. Sci.* 1: 297-318 (1986); Durrleman S, Simon R. Flexible regression models with cubic splines. *Statistics in Medicine* 8:551-561 (1989)].

In addition to optimizing the parameters, model refinement is performed. The first phase of the regression analysis will consist of considering a set of simplified models by eliminating each variable in turn and re-optimizing the likelihood function. The ratio between the two maximum likelihoods of the original vs. the simplified model then provides a significance measure for the contribution of each variable to the model.

The association between each physiogenomic factor and the outcome is calculated using logistic regression models, controlling for the other factors that have been found to be relevant. The magnitude of these associations are measured with the odds ratio and the corresponding 95% confidence interval, and statistical significance assessed using a likelihood ratio test. Multivariate analyses is used which includes all factors that have been found to be important based on univariate analyses.

Because the number of possible comparisons can become very large in analyses that evaluate the combined effects of two or more genes, the results include a random permutation test for the null hypothesis of no effect for two through five combinations of genes. This is accomplished by randomly assigning the outcome to each individual in the study, which is implied by the null distribution of no genetic effect, and estimating the test statistic that corresponds to the null hypothesis of the gene combination effect. Repeating this process 1000 times will provide an empirical estimate of the distribution for the test statistic, and hence a p-value that takes into account the process that gave rise to the multiple comparisons. In addition, hierarchical regression analysis is considered to generate estimates incorporating prior information about the biological activity of the gene variants. In this type of analysis, multiple genotypes and other risk factors can be considered simultaneously as a set, and estimates will be adjusted based on prior information and the observed covariance, theoretically improving the accuracy and precision of effect estimates [Steenland K, Bray I, Greenland S, Boffetta P. Empirical Bayes adjustments for multiple results in hypothesis-generating or surveillance studies. Ca Epidemiol Biomarkers Prev. 9:895-903 (2000).].

c. Power calculations. The power available for detecting an odds ratio (OR) of a specified size for a particular allele was determined on the basis of a significance test on the corresponding difference in proportions using a 5% level of significance. The approach for calculating power involved the adaptation of the method given by Rosner [Rosner B: *Fundamentals of Biostatistics*. Belmont, Calif.: Wadsworth Publishing Co. (1995)]. The SNPs that are explored in this research are not so common as to have prevalence of more than 35%, but rather in the range of 10-15%. Therefore, it is apparent that the study has at least 80% power to detect odds ratios in the range of 1.6-1.8, which are modest effects.

d. Model validation. A cross-validation approach is used to evaluate the performance of models by separating the data used for parameterization (training set) from the data used for testing (test set). The approach randomly divides the population into the training set, which will comprise 80% of the subjects, and the remaining 20% will be the test set. The algorithmic approach is used for finding a model that can be used for prediction of exercise response that will occur in a subject using the data in the training set. This prediction equation is then used to prepare an ROC curve that provides an independent estimate of the relationship between sensitivity and specificity for the prediction model.

e. Patient Physiotype. The outcome variables broken down by demographic factors are shown in Tables 8, 11a, 13, 16, 19, and 22. Each of the below-identified SNPs are preferred embodiments of the present invention. Tables 9, 11b, 14, 17, 20, and 23 show the covariate models for each drug.

Tables 10, 12, 15, 18, 21, and 24 show a collection of physiotypes for the outcomes total cholesterol (TC) level, LDL cholesterol level, HDL cholesterol level, total cholesterol to HDL cholesterol ratio, triglyceride level, blood glucose level, systolic blood pressure, diastolic blood pressure, body mass (BMS), body mass index (BMI), waist circumference, and metabolic syndromes index (MSI). Each physiotype in this particular embodiment consists of a selection of markers, and intercept value (C), and a coefficient (ci) for each marker. For example, the LDL physiotype of Arapiprazole consists of the markers rs1057910, rs9904270, rs2229416, rs7412, rs701492, rs5030390, rs7816340, rs10509676, rs2227852, rs1805002, rs2192752, and rs2070937, and the corresponding coefficients −0.69332, 0.92074, 0.304557, 0.24679, 0.533415, 0.137428, 0.438641, 0.438448, −0.56042, 0.573261, −0.4248, and −0.30652, respectively. The predicted LDL response for a given individual is then given by the formula:

$$\Delta LDL = C + \sum_i c_i g_i$$

where C is the intercept, the $c_i$ are the coefficients and the $g_i$ are the genotypes, coded 0 for the wild type allele homozygote, 1 for the heterozygote, and 2 for the variant allele homozygote.

In this embodiment, the physiotype consists of a linear regression model. In other embodiments, the physiotype might consist of a generalized linear regression model, a structural equation model, a Baysian probability network, or any other modeling tool known to the practitioner of the art of statistics.

TABLE 8

| | | | | | | | | | |
|---|---|---|---|---|---|---|---|---|---|
| | | Arapiprazole Covariates | | | | | | | |
| | | Gender | | Age | | | | Heritage | |
| Sample (N) | All 36 | female 10 | male 26 | 20-30 8 | 30-40 16 | 40-50 8 | 50-60 4 | African Am 3 | Caucasian 33 |
| TC (N) | 179.78 (36) | 174 (10) | 182 (26) | 173.625 (8) | 189.44 (16) | 176.25 (8) | 160.5 (4) | 183.33 (3) | 179.45 (33) |
| LDL (N) | 93.47 (36) | 87 (10) | 95.96 (26) | 90.5 (8) | 97.19 (16) | 94.25 (8) | 83 (4) | 104 (3) | 92.52 (33) |

TABLE 8-continued

Arapiprazole Covariates

| Sample (N) | All 36 | Gender | | Age | | | | Heritage | |
|---|---|---|---|---|---|---|---|---|---|
| | | female 10 | male 26 | 20-30 8 | 30-40 16 | 40-50 8 | 50-60 4 | African Am 3 | Caucasian 33 |
| HDL | 51.75 | 58.4 | 49.19 | 49.63 | 52.19 | 52.63 | 52.5 | 54.333 | 51.52 |
| (N) | (36) | (10) | (26) | (8) | (16) | (8) | (4) | (3) | (33) |
| Log (TG) | 5.045 | 4.929 | 5.09 | 5.097 | 5.152 | 4.904 | 4.798 | 4.768 | 5.071 |
| (N) | (36) | (10) | (26) | (8) | (16) | (8) | (4) | (3) | (33) |
| TC/HDL | 3.808 | 3.127 | 4.07 | 3.886 | 4.059 | 3.557 | 3.148 | 3.418 | 3.843 |
| (N) | (36) | (10) | (26) | (8) | (16) | (8) | (4) | (3) | (33) |
| Glucose | 95.29 | 97.7 | 94.32 | 86.5 | 95.93 | 104.25 | 92.5 | 91.67 | 95.63 |
| (N) | (35) | (10) | (25) | (8) | (15) | (8) | (4) | (3) | (32) |
| Systolic BP | 122.17 | 118.8 | 123.46 | 130.25 | 122.38 | 114.75 | 120 | 107.33 | 123.52 |
| (N) | (36) | (10) | (26) | (8) | (16) | (8) | (4) | (3) | (33) |
| Diastolic BP | 75.86 | 75 | 76.19 | 76.625 | 75.25 | 74.75 | 79 | 65.33 | 76.82 |
| (N) | (36) | (10) | (26) | (8) | (16) | (8) | (4) | (3) | (33) |
| Body Mass | 86.58 | 80.61 | 88.97 | 75.47 | 84.69 | 97.8 | 91.125 | 74.8 | 87.68 |
| (N) | (35) | (10) | (25) | (7) | (16) | (8) | (4) | (3) | (32) |
| BMI | 28.56 | 29.47 | 28.22 | 28.28 | 28.44 | 28.09 | 30.6 | 24.17 | 28.96 |
| (N) | (36) | (10) | (26) | (8) | (16) | (8) | (4) | (3) | (33) |
| Waist circumference | 101.34 | 100.65 | 101.61 | 97.48 | 101.74 | 102.78 | 104.63 | 86.83 | 102.66 |
| (N) | (36) | (10) | (26) | (8) | (16) | (8) | (4) | (3) | (33) |
| MSI | 0.0619 | −0.2967 | 0.1998 | −0.1379 | 0.1839 | 0.0187 | 0.0595 | −1.2227 | 0.1787 |
| (N) | (36) | (10) | (26) | (8) | (16) | (8) | (4) | (3) | (33) |

TABLE 9

Arapiprazole Covariate Model

| response | variable | explains | p |
|---|---|---|---|
| TC | Total | 0 | 1 |
| LDL | Total | 0 | 1 |
| HDL | Gender | 0.069386 | 0.12 |
| HDL | Total | 0.069386 | 0.12 |
| Log(TG) | Total | 0 | 1 |
| TC/HDL | Gender | 0.103671 | 0.055 |
| TC/HDL | Total | 0.103671 | 0.055 |
| Glucose | Age | 0.078958 | 0.1 |
| Glucose | Total | 0.078958 | 0.1 |
| sBP | Age | 0.126991 | 0.025 |
| sBP | Heritage | 0.088631 | 0.057 |
| sBP | Gender | 0.053972 | 0.134 |
| sBP | Total | 0.269595 | 0.017 |
| dBP | Heritage | 0.188499 | 0.0082 |
| dBP | Total | 0.188499 | 0.0082 |
| BM | Total | 0 | 1 |
| BMI | Total | 0 | 1 |
| Waist | Total | 0 | 1 |
| MSI | Heritage | 0.106382 | 0.048 |
| MSI | Gender | 0.063872 | 0.121 |
| MSI | Total | 0.170253 | 0.046 |

TABLE 10

Arapiprazole Physiotypes

| SNP | Gene | Allele | $c_i$ |
|---|---|---|---|
| Total Cholesterol Physiotype | | | |
| rs1057910 | CYP2C9 | AC | −0.3308 |
| rs9904270 | RARA | TC | 0.608703 |
| rs2288911 | APOC4 | AC | −0.4205 |
| rs3760396 | CCL2 | GC | 0.558444 |
| rs3024492 | IL10 | TA | −0.21807 |
| rs2301108 | HIF1A | AG | −0.4038 |
| rs2229416 | ACACA | AG | 0.443364 |
| rs7254060 | INSR | AG | 0.523456 |
| rs7412 | APOE | TC | 0.305044 |

TABLE 10-continued

Intercept (C) = 0.024589

| SNP | Gene | Allele | $c_i$ |
|---|---|---|---|
| LDL Cholesterol Physiotype | | | |
| rs1057910 | CYP2C9 | AC | −0.69332 |
| rs9904270 | RARA | TC | 0.92074 |
| rs2229416 | ACACA | AG | 0.304557 |
| rs7412 | APOE | TC | 0.24679 |
| rs701492 | GAD1 | TC | 0.533415 |
| rs5030390 | ICAM1 | AG | 0.137428 |
| rs7816340 | ADRA1A | TC | 0.438641 |
| rs10509676 | CYP2C19 | TA | 0.438448 |
| rs2227852 | DRD5 | AG | −0.56042 |
| rs1805002 | CCKBR | AG | 0.573261 |
| rs2192752 | IL1R1 | AC | −0.4248 |
| rs2070937 | HP | AG | −0.30652 |
| Intercept (C) = 0.244116 | | | |
| HDL Cholesterol Physiotype | | | |
| rs701492 | GAD1 | TC | 0.597956 |
| rs3771892 | TNFAIP6 | AG | 0.698562 |
| rs3792822 | PRKAA1 | AG | 0.64794 |
| rs814628 | LIPF | AG | −0.64177 |
| rs8192708 | PCK1 | AG | −0.25086 |
| rs10515521 | NR3C1 | AG | 0.368471 |
| rs3853188 | SCARB2 | AC | 0.581254 |
| rs6837793 | NPY5R | AG | 0.305743 |
| rs3761422 | ADORA2A | TC | −0.16746 |
| rs5880 | CETP | CG | −0.31943 |
| rs295 | LPL | AC | 0.161313 |
| Intercept (C) = −0.37056 | | | |
| Log (TG) Physiotype | | | |
| rs2288911 | APOC4 | AC | −0.26688 |
| rs3024492 | IL10 | TA | −0.21706 |
| rs2301108 | HIF1A | AG | −0.16209 |
| rs814628 | LIPF | AG | −0.29863 |
| rs573542 | ADRA1A | AG | −0.02354 |
| rs4149578 | TNFRSF1A | AG | 0.150318 |
| rs1003854 | AIRE | TC | −0.2079 |
| rs617333 | TEK | TG | −0.29189 |
| rs1061622 | TNFRSF1B | TG | −0.40453 |
| rs1860743 | PRKAG2 | AG | −0.73163 |
| rs3769671 | POMC | AC | 1.134519 |
| rs1801282 | PPARG | CG | −0.13973 |
| rs1478290 | GYS2 | TG | 0.109532 |

TABLE 10-continued

| | | | |
|---|---|---|---|
| rs7072137 | GAD2 | AG | −0.32128 |

Intercept (C) = 0.916667

Total Cholesterol/HDL Cholesterol Ratio Physiotype

| | | | |
|---|---|---|---|
| rs701492 | GAD1 | TC | 0.586989 |
| rs3771892 | TNFAIP6 | AG | 0.41526 |
| rs3792822 | PRKAA1 | AG | 0.687957 |
| rs814628 | LIPF | AG | −0.34903 |
| rs5880 | CETP | CG | −0.4592 |
| rs1860743 | PRKAG2 | AG | −0.35154 |
| rs1478290 | GYS2 | TG | 0.193831 |
| rs2228502 | CPT1A | TC | −0.46379 |
| rs3176921 | CRH | TC | 0.389355 |

Intercept (C) = −0.34981

Blood Glucose Physiotype

| | | | |
|---|---|---|---|
| rs1356413 | PIK3CA | GC | −1.21132 |
| rs2066470 | MTHFR | TC | 0.439807 |
| rs659734 | HTR2A | TC | −1.20256 |
| rs132642 | APOL3 | TA | −0.42628 |
| rs4245232 | LIPG | AC | −0.57374 |
| rs1800206 | PPARA | GC | −0.77956 |

Intercept (C) = 0.366514

Systolic Blood Pressure Physiotype

| | | | |
|---|---|---|---|
| rs2229416 | ACACA | AG | −0.56301 |
| rs6265 | BDNF | AG | 0.381994 |
| rs3766560 | ADORA1 | AG | 0.513186 |
| rs10507383 | FLT1 | CG | 0.712754 |
| rs4531 | DBH | TG | −0.57352 |
| rs2015353 | ADORA2B | AG | −0.29789 |
| rs854572 | PON1 | CG | 0.192613 |

Intercept (C) = −0.18621

Diastolic Blood Pressure Physiotype

| | | | |
|---|---|---|---|
| rs10515521 | NR3C1 | AG | 0.323752 |
| rs3853188 | SCARB2 | AC | −0.36312 |
| rs3766560 | ADORA1 | AG | 0.107639 |
| rs11632618 | LIPC | AG | 0.809303 |
| rs849404 | PIK3CG | AG | −0.40551 |
| rs10890819 | ACAT1 | TC | 1.559462 |
| rs231460 | PYY | AG | −0.59519 |
| rs2069827 | IL6 | TG | −0.3329 |
| rs6083 | LIPC | AG | 0.44463 |
| rs12333983 | CYP3A4 | TA | 0.722335 |
| rs877172 | OXT | AC | 0.185439 |
| rs833060 | VEGF | TG | −0.36059 |
| rs11212515 | ACAT1 | AT | −1.23221 |
| rs748253 | FLT1 | TG | −0.23313 |
| rs1799821 | CPT2 | AG | −0.21295 |
| rs722341 | ABCC8 | TC | −0.31313 |

Intercept (C) = −0.05506

Body Mass Physiotype

| | | | |
|---|---|---|---|
| rs854572 | PON1 | CG | 0.217607 |
| rs11632618 | LIPC | AG | 0.803778 |
| rs231460 | PYY | TC | −0.24949 |
| rs3846662 | HMGCR | TC | −0.21286 |
| rs1800545 | ADRA2A | AG | −0.69588 |
| rs4680 | COMT | AG | 0.50542 |
| rs2070586 | DAO | AG | −0.48428 |
| rs3764261 | CETP | TG | −0.22463 |
| rs1611115 | DBH | TC | −0.42568 |

Intercept (C) = 0.184512

Body Mass Index Physiotype

| | | | |
|---|---|---|---|
| rs5030390 | ICAM1 | AG | −1.17589 |
| rs1877394 | PIK3C2B | AG | −3.14895 |
| rs2298122 | DRD1IP | TG | 0.831378 |
| rs10515070 | PIK3R1 | AT | −0.58294 |
| rs4762 | AGT | TC | −0.60445 |
| rs8178990 | CHAT | TC | −0.72565 |
| rs1396862 | CRHR1 | TC | −0.23991 |
| rs4784642 | GNAO1 | AG | 0.312765 |

Intercept (C) = 0.27634

Waist circumference Physiotype

| | | | |
|---|---|---|---|
| rs231460 | PYY | TC | 0.68651 |
| rs3764261 | CETP | TG | 0.226497 |
| rs10515070 | PIK3R1 | AT | 0.753063 |
| rs4762 | AGT | TC | 0.526671 |
| rs2515449 | MCPH1 | AG | −0.6936 |
| rs264 | LPL | AG | 0.291085 |

Intercept (C) = −0.88804

Metabolic Syndromes Index (MSI) Physiotype

| | | | |
|---|---|---|---|
| rs2301108 | HIF1A | AG | −0.40998 |
| rs11632618 | LIPC | AG | 0.388122 |
| rs231460 | PYY | TC | −0.38818 |
| rs833060 | VEGF | TG | 0.35826 |
| rs3846662 | HMGCR | TC | −0.31492 |
| rs4784642 | GNAO1 | AG | 0.506564 |
| rs6809631 | PPARG | AT | −0.3585 |
| rs10082776 | RARG | AG | −0.51342 |

Intercept (C) = −0.04177

TABLE 11a

| | | Olanzapine Covariates | | | | | |
|---|---|---|---|---|---|---|---|
| | | Gender | | Age | | | |
| Sample | All | female | male | <20 | 20-30 | 30-40 | 40-50 |
| (N) | 67 | 19 | 48 | 1 | 20 | 22 | 20 |
| TC | 192.60 | 212.16 | 184.85 | 120.00 | 189.00 | 189.82 | 202.00 |
| (N) | (67) | (19) | (48) | (1) | (20) | (22) | (20) |
| LDL | 104.11 | 118.94 | 98.54 | 68.00 | 104.10 | 103.73 | 107.00 |
| (N) | (66) | (18) | (48) | (1) | (20) | (22) | (19) |
| HDL | 49.45 | 51.89 | 48.48 | 28.00 | 48.55 | 47.68 | 52.40 |
| (N) | (67) | (19) | (48) | (1) | (20) | (22) | (20) |
| Log (TG) | 5.072 | 4.985 | 5.107 | 4.787 | 5.086 | 5.168 | 4.968 |
| (N) | (67) | (19) | (48) | (1) | (20) | (22) | (20) |
| TC/HDL | 4.145 | 4.411 | 4.040 | 4.300 | 4.068 | 4.203 | 4.205 |
| (N) | (67) | (19) | (48) | (1) | (20) | (22) | (20) |
| Glucose | 91.22 | 97.53 | 88.98 | 109.00 | 88.65 | 92.29 | 92.47 |
| (N) | (65) | (17) | (48) | (1) | (20) | (21) | (19) |
| sBP | 118.58 | 116.79 | 119.29 | 109.00 | 118.20 | 117.32 | 119.10 |
| (N) | (67) | (19) | (48) | (1) | (20) | (22) | (20) |
| dBP | 76.12 | 75.84 | 76.23 | 77.00 | 75.15 | 74.14 | 78.10 |
| (N) | (67) | (19) | (48) | (1) | (20) | (22) | (20) |
| BM | 82.90 | 82.39 | 83.10 | 65.00 | 87.06 | 83.17 | 79.34 |
| (N) | (67) | (19) | (48) | (1) | (20) | (22) | (20) |

TABLE 11a-continued

| | | | Olanzapine Covariates | | | | |
|---|---|---|---|---|---|---|---|
| BMI | 27.12 | 30.50 | 25.78 | 25.39 | 28.05 | 26.93 | 27.02 |
| (N) | (67) | (19) | (48) | (1) | (20) | (22) | (20) |
| Waist | 98.21 | 100.74 | 97.21 | 96.00 | 99.18 | 97.82 | 98.32 |
| (N) | (67) | (19) | (48) | (1) | (20) | (22) | (20) |
| MSI | −0.129 | −0.075 | −0.151 | −0.196 | −0.109 | −0.169 | −0.138 |
| (N) | (67) | (19) | (48) | (1) | (20) | (22) | (20) |

| | Age | | Heritage | | | |
|---|---|---|---|---|---|---|
| Sample | 50-60 | 70-80 | AA | Cauc. | Hisp. | Other |
| (N) | 3 | 1 | 14 | 50 | 1 | 2 |
| TC | 204.67 | 174.0 | 197.57 | 193.30 | 216.00 | 128.50 |
| (N) | (3) | (1) | (14) | (50) | (1) | (2) |
| LDL | 104.00 | 94.00 | 109.14 | 103.53 | 147.00 | 61.50 |
| (N) | (3) | (1) | (14) | (49) | (1) | (2) |
| HDL | 49.67 | 68.00 | 54.00 | 48.16 | 47.00 | 51.00 |
| (N) | (3) | (1) | (14) | (50) | (1) | (2) |
| Log (TG) | 5.373 | 4.159 | 5.060 | 5.115 | 4.700 | 4.263 |
| (N) | (3) | (1) | (14) | (50) | (1) | (2) |
| TC/HDL | 4.316 | 2.559 | 3.836 | 4.264 | 4.600 | 3.100 |
| (N) | (3) | (1) | (14) | (50) | (1) | (2) |
| Glucose | 86.67 | 92.00 | 98.31 | 89.24 | 91.00 | 93.50 |
| (N) | (3) | (1) | (13) | (49) | (1) | (2) |
| sBP | 136.33 | 100.0 | 119.79 | 118.38 | 132.00 | 108.50 |
| (N) | (3) | (1) | (14) | (50) | (1) | (2) |
| dBP | 87.00 | 66.00 | 77.00 | 75.48 | 91.00 | 78.50 |
| (N) | (3) | (1) | (14) | (50) | (1) | (2) |
| BM | 95.73 | 44.40 | 87.38 | 81.98 | 110.91 | 60.45 |
| (N) | (3) | (1) | (14) | (50) | (1) | (2) |
| BMI | 27.23 | 15.90 | 28.16 | 26.87 | 34.61 | 22.26 |
| (N) | (3) | (1) | (14) | (50) | (1) | (2) |
| Waist | 105.80 | 65.00 | 96.82 | 98.17 | 144.00 | 86.00 |
| (N) | (3) | (1) | (14) | (50) | (1) | (2) |
| MSI | 0.919 | −2.52 | −0.086 | −0.126 | 1.402 | −1.272 |
| (N) | (3) | (1) | (14) | (5) | (1) | (2) |

TABLE 11b

| Olanzapine Covariate Model | | | |
|---|---|---|---|
| response | variable | explains | p |
| TC | Gender | 0.059989 | 0.046 |
| TC | Total | 0.059989 | 0.046 |
| LDL | Site | 0.072682 | 0.021 |
| LDL | Heritage | 0.112048 | 0.043 |
| LDL | Gender | 0.036398 | 0.099 |
| LDL | Total | 0.221129 | 0.009 |
| HDL | Total | 0 | 1 |
| log(TG) | Site | 0.044131 | 0.088 |
| log(TG) | Total | 0.044131 | 0.088 |
| TC/HDL | Site | 0.034284 | 0.13 |
| TC/HDL | Total | 0.034284 | 0.13 |
| Glucose | Gender | 0.042175 | 0.1 |
| Glucose | Total | 0.042175 | 0.1 |
| sBP | Total | 0 | 1 |
| dBP | Site | 0.057953 | 0.05 |
| dBP | Total | 0.057953 | 0.05 |
| BM | Heritage | 0.091797 | 0.11 |
| BM | Total | 0.091797 | 0.11 |
| BMI | Gender | 0.125548 | 0.0033 |
| BMI | Total | 0.125548 | 0.0033 |
| Waist | Heritage | 0.151288 | 0.014 |
| Waist | Site | 0.029753 | 0.138 |
| Waist | Total | 0.181041 | 0.014 |
| MSI | Total | 0 | 1 |

TABLE 12

| Olanzapine Physiotypes | | | |
|---|---|---|---|
| SNP | Gene | Allele | $c_i$ |
| Total Cholesterol Physiotype | | | |
| rs1801253 | ADRB1 | GC | −0.23422 |
| rs1176744 | HTR3B | TG | −0.21674 |
| rs9659997 | HTR6 | TC | −0.25515 |
| rs26312 | GHRL | AG | 0.336429 |
| rs3761422 | ADORA2A | TC | −0.42738 |
| rs5030390 | ICAM1 | AG | −0.7513 |
| rs3024492 | IL10 | TA | 0.269953 |
| rs3769671 | POMC | AC | −0.67161 |
| rs12695902 | AGTR1 | AG | 0.502822 |
| rs1049793 | ABP1 | GC | 0.24705 |
| rs2241220 | ACACB | TC | −0.32029 |
| Intercept (C) = 0.695095 | | | |
| LDL Cholesterol Physiotype | | | |
| rs1176744 | HTR3B | TG | −0.23004 |
| rs1049793 | ABP1 | GC | 0.259861 |
| rs2241220 | ACACB | TC | −0.44936 |
| rs1468271 | NPY | AG | −0.38604 |
| rs7412 | APOE | TC | 0.307709 |
| rs894251 | SCARB2 | TC | 0.33676 |
| rs1801278 | IRS1 | AG | 0.546773 |
| rs3847063 | ACHE | AG | −0.19611 |
| rs4680 | COMT | AG | −0.21793 |
| rs3219177 | RETN | TC | −0.23289 |
| rs1322783 | DISC1 | TC | −0.24648 |
| rs1556478 | LIPA | AG | −0.17346 |
| rs1478290 | GYS2 | TG | −0.20589 |
| Intercept (C) = 0.605582 | | | |

TABLE 12-continued

HDL Cholesterol Physiotype

| | | | |
|---|---|---|---|
| Intercept | | | −0.77544 |
| rs931992 | TCAP | AC | 0.164429 |
| rs676643 | HTR1D | AG | −0.53546 |
| rs2471857 | DRD2 | AG | 0.401311 |
| rs701492 | GAD1 | TC | 0.672668 |
| rs11044082 | PIK3C2G | TG | 0.452712 |
| rs132642 | APOL3 | TA | −0.51732 |
| rs334555 | GSK3B | CG | −0.37538 |
| rs405509 | APOE | AC | 0.251575 |
| rs167771 | DRD3 | AG | −0.26381 |
| rs9904270 | RARA | TC | 0.422562 |
| rs461404 | PRKAA1 | TC | 0.236608 |

Intercept (C) = −0.77544

Log(TG) Physiotype

| | | | |
|---|---|---|---|
| rs1801253 | ADRB1 | GC | −0.35894 |
| rs26312 | GHRL | AG | 0.397031 |
| rs4646450 | CYP3A5 | TC | 0.729464 |
| rs2296189 | FLT1 | AG | −0.3701 |
| rs2242480 | CYP3A4 | TC | −0.56627 |
| rs5369 | EDN1 | AG | 0.418791 |
| rs1042718 | ADRB2 | AC | 0.282758 |
| rs1547387 | SLC39A7 | GC | −0.66347 |
| rs2069827 | IL6 | TG | −0.43984 |
| rs4726107 | LOC441301 | TC | −0.47126 |
| rs1800794 | IL1A | TC | −0.27367 |

Intercept (C) = 0.255663

Total Cholesterol/HDL Cholesterol Ratio Physiotype

| | | | |
|---|---|---|---|
| rs1556478 | LIPA | AG | −0.34362 |
| rs701492 | GAD1 | TC | 0.265293 |
| rs11044082 | PIK3C2G | TG | 0.379559 |
| rs334555 | GSK3B | CG | −0.35789 |
| rs9904270 | RARA | TC | 0.309321 |
| rs776746 | CYP3A5 | AG | 0.297857 |
| rs4994 | ADRB3 | TC | −0.64021 |
| rs1800808 | SELP | TC | −0.70387 |
| rs2298122 | DRD1IP | TG | 0.349292 |
| rs1801105 | HNMT | TC | −0.37359 |
| rs3762272 | PKLR | AG | −1.49503 |
| rs5880 | CETP | CG | −0.73777 |
| rs758857 | ADORA2B | AG | −0.33693 |
| rs936960 | LIPC | AC | 0.301791 |

Intercept (C) = 0.237794

Blood Glucose Physiotype

| | | | |
|---|---|---|---|
| rs1001293 | APOL2 | TC | −0.45931 |
| rs5070 | APOA1 | AG | −0.33846 |
| rs6967107 | WBSCR14 | AC | 0.71023 |
| rs429358 | APOE | TC | −0.51256 |
| rs722341 | ABCC8 | TC | 0.39478 |

Intercept (C) = 0.346762

Systolic Blood Pressure Physiotype

| | | | |
|---|---|---|---|
| rs1801253 | ADRB1 | GC | −0.27455 |
| rs701492 | GAD1 | TC | 0.393014 |
| rs1058167 | CYP2D6 | TC | 0.266929 |
| rs3762611 | GABRA4 | AG | 0.374479 |
| rs659734 | HTR2A | TC | −1.27217 |
| rs694066 | GAL | AG | −0.42236 |
| rs2702285 | AVEN | AG | −0.36275 |
| rs2298191 | ADORA3 | TC | −0.35781 |
| rs3791850 | GAD1 | TC | −0.38316 |
| rs2306179 | GYS2 | AG | −0.32341 |

Intercept (C) = 0.57794

Diastolic Blood Pressure Physiotype

| | | | |
|---|---|---|---|
| rs5742612 | IGF1 | TC | −0.53278 |
| rs5766741 | PPARA | TC | −0.37718 |
| rs3757868 | ACHE | AG | −0.59012 |
| rs1871143 | GYS2 | TG | −0.56262 |
| rs167770 | DRD3 | AG | 0.360872 |
| rs8178847 | APOH | AG | 0.427114 |
| rs11188092 | CYP2C19 | AC | −0.26322 |

Intercept (C) = 0.560526

Body Mass Physiotype

| | | | |
|---|---|---|---|
| rs7412 | APOE | TC | −0.47086 |
| rs9904270 | RARA | TC | 0.631676 |
| rs1547387 | SLC39A7 | GC | −0.42197 |
| rs5092 | APOA4 | AG | 0.496704 |
| rs4149056 | SLCO1B1 | TC | 0.396704 |
| rs6032470 | GHRH | TC | −0.28514 |
| rs4765623 | SCARB1 | TC | −0.23389 |

Intercept (C) = 0.077815

Body Mass Index Physiotype

| | | | |
|---|---|---|---|
| rs3024492 | IL10 | TA | 0.23525 |
| rs132642 | APOL3 | TA | 0.293474 |
| rs9904270 | RARA | TC | 0.606388 |
| rs1547387 | SLC39A7 | GC | −0.59075 |
| rs1128503 | ABCB1 | TC | 0.170075 |
| rs891087 | INSR | AG | −0.93335 |
| rs2067477 | CHRM1 | AC | 1.539077 |
| rs6901 | PFKP | AG | 0.35015 |
| rs619698 | SSTR5 | AC | −0.22381 |
| rs1549758 | NOS3 | TC | −0.1818 |

Intercept (C) = −0.05469

Waist circumference Physiotype

| | | | |
|---|---|---|---|
| rs7412 | APOE | TC | 0.480991 |
| rs9904270 | RARA | TC | −0.62718 |
| rs1547387 | SLC39A7 | GC | 0.428165 |
| rs5092 | APOA4 | AG | −0.33032 |
| rs4149056 | SLCO1B1 | TC | −0.26043 |
| rs2067477 | CHRM1 | AC | −0.90248 |
| rs1029947 | PRKAG2 | AG | −0.45428 |

Intercept (C) = 0.219704

Metabolic Sysndrome Index Physiotype

| | | | |
|---|---|---|---|
| rs9904270 | RARA | TC | 0.761315 |
| rs936960 | LIPC | AC | 0.668552 |
| rs5742612 | IGF1 | TC | −0.72108 |
| rs1128503 | ABCB1 | TC | 0.383472 |
| rs891087 | INSR | AG | −1.02516 |
| rs1549758 | NOS3 | TC | −0.97906 |
| rs814628 | LIPF | AG | −0.622 |
| rs10509676 | CYP2C19 | TA | 0.317557 |
| rs1799983 | NOS3 | TG | 0.681573 |

Intercept (C) = −0.26092

TABLE 13

Quetiapine Covariates

| | | Gender | | Age | | | | | | Heritage | |
|---|---|---|---|---|---|---|---|---|---|---|---|
| | All | female | male | <20 | 20-30 | 30-40 | 40-50 | 50-60 | 60-70 | AA | Cauc. |
| N | 95 | 38 | 57 | 5 | 20 | 37 | 24 | 6 | 3 | 8 | 87 |
| TC | 192.33 | 186.84 | 195.98 | 160.60 | 180.15 | 201.57 | 197.13 | 185.50 | 187.67 | 191.63 | 192.39 |
| (N) | (95) | (38) | (57) | (5) | (20) | (37) | (24) | (6) | (3) | (8) | (87) |
| LDL | 96.71 | 92.89 | 99.19 | 87.40 | 91.35 | 102.92 | 94.39 | 97.33 | 88.00 | 94.38 | 96.93 |
| (N) | (94) | (37) | (57) | (5) | (20) | (37) | (23) | (6) | (3) | (8) | (86) |
| HDL | 49.79 | 50.34 | 49.42 | 47.20 | 52.05 | 47.32 | 50.96 | 57.50 | 44.67 | 50.25 | 49.75 |
| (N) | (95) | (38) | (57) | (5) | (20) | (37) | (24) | (6) | (3) | (8) | (87) |

TABLE 13-continued

Quetiapine Covariates

| N | All 95 | Gender | | Age | | | | | | Heritage | |
|---|---|---|---|---|---|---|---|---|---|---|---|
| | | female 38 | male 57 | <20 5 | 20-30 20 | 30-40 37 | 40-50 24 | 50-60 6 | 60-70 3 | AA 8 | Cauc. 87 |
| Log (TG) | 5.263 | 5.185 | 5.315 | 4.737 | 5.118 | 5.390 | 5.320 | 5.000 | 5.620 | 5.220 | 5.267 |
| (N) | (95) | (38) | (57) | (5) | (20) | (37) | (24) | (6) | (3) | (8) | (87) |
| TC/HDL | 4.023 | 3.913 | 4.098 | 3.729 | 3.607 | 4.401 | 4.041 | 3.211 | 4.245 | 3.552 | 4.061 |
| (N) | (94) | (38) | (56) | (5) | (20) | (36) | (24) | (6) | (3) | (7) | (87) |
| Glucose | 92.08 | 97.74 | 88.32 | 89.60 | 81.45 | 90.54 | 100.17 | 103.00 | 99.67 | 91.00 | 92.18 |
| (N) | (95) | (38) | (57) | (5) | (20) | (37) | (24) | (6) | (3) | (8) | (87) |
| sBP | 120.07 | 117.32 | 121.91 | 118.80 | 117.65 | 122.11 | 116.17 | 127.67 | 129.33 | 125.00 | 119.62 |
| (N) | (95) | (38) | (57) | (5) | (20) | (37) | (24) | (6) | (3) | (8) | (87) |
| dBP | 75.04 | 74.58 | 75.35 | 66.80 | 72.55 | 78.00 | 72.67 | 79.00 | 80.00 | 74.50 | 75.09 |
| (N) | (95) | (38) | (57) | (5) | (20) | (37) | (24) | (6) | (3) | (8) | (87) |
| BM | 87.05 | 81.79 | 90.61 | 91.84 | 78.57 | 89.99 | 90.05 | 84.22 | 81.93 | 98.56 | 85.97 |
| (N) | (94) | (38) | (56) | (5) | (20) | (36) | (24) | (6) | (3) | (8) | (86) |
| BMI | 29.44 | 31.15 | 28.30 | 24.46 | 24.51 | 31.31 | 31.78 | 30.07 | 27.53 | 32.00 | 29.20 |
| (N) | (95) | (38) | (57) | (5) | (20) | (37) | (24) | (6) | (3) | (8) | (87) |
| Waist | 102.05 | 100.20 | 103.21 | 88.00 | 93.15 | 102.78 | 109.57 | 107.17 | 108.00 | 108.55 | 101.43 |
| (M) | (93) | (36) | (57) | (5) | (20) | (36) | (23) | (6) | (3) | (8) | (85) |
| MSI | 0.263 | 0.267 | 0.260 | −0.933 | −0.546 | 0.586 | 0.597 | 0.231 | 1.040 | 0.403 | 0.250 |
| (N) | (95) | (38) | (57) | (5) | (20) | (37) | (24) | ( ) | (3) | (8) | (87_ |

TABLE 14

Quetiapine Covariate Model

| response | variable | explains | p |
|---|---|---|---|
| TC | Total | 0 | 1 |
| LDL | Total | 0 | 1 |
| HDL | Total | 0 | 1 |
| Log(TG) | Age | 0.022702 | 0.14 |
| Log(TG) | Total | 0.022702 | 0.14 |
| TC/HDL | Total | 0 | 1 |
| Glucose | Age | 0.130704 | 0.00028 |
| Glucose | Gender | 0.02867 | 0.07981 |
| Glucose | Total | 0.159375 | 0.00034 |
| sBP | Gender | 0.036838 | 0.06 |
| sBP | Age | 0.030598 | 0.086 |
| sBP | Total | 0.067436 | 0.04 |
| dBP | Age | 0.044866 | 0.039 |
| dBP | Total | 0.044866 | 0.039 |
| BM | Gender | 0.040775 | 0.051 |
| BM | Total | 0.040775 | 0.051 |
| BMI | Age | 0.053872 | 0.023 |
| bmi | Gender | 0.022535 | 0.137 |
| BMI | Total | 0.076407 | 0.026 |
| Waist | Age | 0.09002 | 0.0035 |
| Waist | Total | 0.09002 | 0.0035 |
| MSI | Age | 0.092414 | 0.0027 |
| MSI | Total | 0.092414 | 0.0027 |

TABLE 15

Quetiapine Physiotypes

| SNP | Gene | Allele | $c_i$ |
|---|---|---|---|
| Total Cholesterol Physiotype | | | |
| rs2228139 | IL1R1 | GC | 0.8446253 |
| rs2230461 | PIK3CA | AG | −0.4577208 |
| rs3791981 | APOB | AG | −0.4491035 |
| rs12695902 | AGTR1 | AG | −0.5795818 |
| rs4149056 | SLCO1B1 | TC | 0.2330744 |
| rs659734 | HTR2A | TC | −0.708202 |
| rs6586179 | LIPA | TC | −0.3113458 |
| rs2287754 | GYS1 | AG | 0.4863012 |
| rs3219177 | RETN | TC | −0.2826261 |
| rs2020933 | SLC6A4 | AT | −0.4206228 |
| Intercept (C) = 0.315259 | | | |
| LDL Cholesterol Physiotype | | | |
| rs2228139 | IL1R1 | GC | 0.5683075 |
| rs659734 | HTR2A | TC | −0.7202465 |
| rs6586179 | LIPA | TC | −0.2747396 |
| rs7247515 | AKT2 | TC | 0.4498296 |
| rs3087454 | CHRNA7 | TG | −0.3336563 |
| rs7520974 | CHRM3 | AG | −0.3109356 |
| rs1061622 | TNFRSF1B | TG | 1.1516671 |
| rs10934502 | GSK3B | TC | −0.4751683 |
| rs662 | PON1 | AG | 0.3441443 |
| rs235249 | TNFRSF1B | TC | −0.8223309 |
| rs2162189 | SST | AG | −0.2582274 |
| Intercept (C) = 0.4327661 | | | |
| HDL Cholesterol Physiotpye | | | |
| rs3791981 | APOB | AG | 0.7393231 |
| rs6083 | LIPC | AG | −0.378628 |
| rs264 | LPL | AG | 0.6648935 |
| rs6078 | LIPC | AG | −1.4269562 |
| rs686874 | HRH2 | TC | 0.5900095 |
| rs9904270 | RARA | TC | −0.4640902 |
| rs7975375 | ADIPOR2 | TC | 0.2573861 |
| rs4726107 | LOC441301 | TC | −0.3750104 |
| rs7072137 | GAD2 | AG | 0.4030395 |
| Intercept (C) = −0.1239112 | | | |
| Log(TG) Physiotype | | | |
| rs2228139 | IL1R1 | GC | 0.57925743 |
| rs2230461 | PIK3CA | AG | −0.50927596 |
| rs2287754 | GYS1 | AG | 0.53917211 |
| rs3219177 | RETN | TC | −0.51955564 |
| rs6078 | LIPC | AG | −1.02487437 |
| rs686874 | HRH2 | TC | 0.48217025 |
| rs4646450 | CYP3A5 | TC | 0.29350287 |
| rs1801253 | ADRB1 | GC | 0.37746753 |
| rs4765623 | SCARB1 | TC | −0.29206157 |
| Intercept (C) = −0.01594963 | | | |
| Total Cholesterol/HDL Cholesterol Ratio Physiotype | | | |
| rs3219177 | RETN | TC | −0.36572327 |
| rs4646450 | CYP3A5 | TC | 0.28423071 |
| rs4765623 | SCARB1 | TC | −0.49481924 |
| rs854572 | PON1 | CG | 0.35946264 |
| rs3756450 | SLC6A3 | TC | −0.57762651 |
| rs8192708 | PCK1 | AG | −0.49094802 |
| rs6489738 | GNB3 | TC | 0.19850829 |
| Intercept (C) = 0.05619099 | | | |

TABLE 15-continued

Blood Glucose Level Physiotype

| | | | |
|---|---|---|---|
| rs6078 | LIPC | AG | −0.659331 |
| rs1176744 | HTR3B | TG | −0.2918175 |
| rs1801278 | IRS1 | AG | −0.5541505 |
| rs4890109 | RARA | TG | 0.9890193 |
| rs2229126 | ADRA1A | AT | −1.0958059 |
| rs1042718 | ADRB2 | AC | −0.4086878 |
| rs1355920 | CHRNA7 | AG | −0.3105216 |
| rs877172 | OXT | AC | −0.1992673 |

Intercept (C) = 0.6773349

Systolic Blood Pressure Physiotype

| | | | |
|---|---|---|---|
| rs1800794 | IL1A | TC | 0.1763215 |
| rs231460 | PYY | TC | −0.5085002 |
| rs11100494 | NPY5R | AC | −0.5659215 |
| rs5070 | APOA1 | AG | −0.4188293 |
| rs3847063 | ACHE | AG | 0.2227394 |
| rs2066470 | MTHFR | TC | −0.4730293 |
| rs821616 | DISC1 | TA | 0.2775048 |
| rs132642 | APOL3 | TA | 0.4083551 |
| rs1356413 | PIK3CA | GC | −0.4870594 |
| rs4301822 | APOF | TC | −0.6378576 |

Intercept (C) = 0.2075119

Diastolic Blood Pressure Physiotype

| | | | |
|---|---|---|---|
| rs2228139 | IL1R1 | GC | 0.5356126 |
| rs2287754 | GYS1 | AG | 0.6617706 |
| rs7072137 | GAD2 | AG | 0.3024 |
| rs5070 | APOA1 | AG | −0.2527833 |
| rs3822222 | CCKAR | TC | −0.3798421 |
| rs10515521 | NR3C1 | AG | 0.2827272 |
| rs1891311 | HTR7 | AG | 0.4293275 |
| rs4149578 | TNFRSF1A | AG | 0.2960228 |

Intercept (C) = −0.1979255

Body Mass Physiotype

| | | | |
|---|---|---|---|
| rs7247515 | AKT2 | TC | −0.4002793 |
| rs8192708 | PCK1 | AG | −0.4216469 |
| rs1042718 | ADRB2 | AC | −0.4178315 |
| rs1800794 | IL1A | TC | 0.188392 |
| rs1891311 | HTR7 | AG | 0.3007671 |
| rs3810947 | CHAT | AG | −0.4850037 |
| rs1801105 | HNMT | TC | −0.9658364 |
| rs1290443 | RARB | AG | −0.4523848 |
| rs849404 | PIK3CG | AG | −0.5240701 |
| rs1190762 | GNAO1 | AC | −0.5410892 |
| rs1800871 | IL10 | TC | 0.2050435 |
| rs7556371 | PIK3C2B | AG | −0.155293 |

Intercept (C) = 0.7612757

Body Mass Index Physiotype

| | | | |
|---|---|---|---|
| rs1042718 | ADRB2 | AC | −0.3466831 |
| rs3822222 | CCKAR | TC | −0.5383191 |
| rs3810947 | CHAT | AG | −0.5540299 |
| rs1801105 | HNMT | TC | −0.6372697 |
| rs12691940 | HNMT | AG | −0.2471322 |
| rs5742612 | IGF1 | TC | −0.9476108 |
| rs891087 | INSR | AG | 0.3963335 |
| rs5896 | F2 | TC | −0.5820443 |
| rs3176921 | CRH | TC | −0.4984213 |
| rs3808607 | CYP7A1 | TG | 0.1769625 |
| rs2430683 | ACACB | TG | 0.2260372 |

Intercept (C) = 0.6033885

Waist circumference Physiotype

| | | | |
|---|---|---|---|
| rs7975375 | ADIPOR2 | TC | 0.302242 |
| rs4890109 | RARA | TG | −0.6608065 |
| rs1356413 | PIK3CA | GC | 0.6114784 |
| rs1290443 | RARB | AG | 0.2631902 |
| rs1800871 | IL10 | TC | −0.2540711 |
| rs5742612 | IGF1 | TC | 0.6762822 |
| rs1283694 | ANGPT1 | TA | 0.2954879 |
| rs405509 | APOE | AC | −0.1906541 |
| rs4762 | AGT | TC | 0.451414 |
| rs597316 | CPT1A | GC | −0.1695007 |
| rs885834 | CHAT | AG | 0.3144139 |
| rs132653 | APOL3 | AC | 0.36752 |

Intercept (C) = −0.461696

Metabolic Syndromes Index (MSI) Physiotype

| | | | |
|---|---|---|---|
| rs2287754 | GYS1 | AG | 0.4483793 |
| rs6078 | LIPC | AG | −1.2221601 |
| rs686874 | HRH2 | TC | 0.5007266 |
| rs7072137 | GAD2 | AG | 0.2338508 |
| rs4646450 | CYP3A5 | TC | 0.192429 |
| rs1042718 | ADRB2 | AC | −0.3830149 |
| rs5070 | APOA1 | AG | −0.2078434 |
| rs3176921 | CRH | TC | −0.299163 |
| rs11503016 | GABRA2 | TA | −0.3435109 |
| rs619698 | SSTR5 | AC | −0.2349905 |
| rs4792887 | CRHR1 | TC | 0.3416708 |

Intercept (C) = 0.2604994

TABLE 16

Risperidone Covariates

| | All | Gender | | Age | | | | | | Heritage | |
| | | female | male | <20 | 20-30 | 30-40 | 40-50 | 50-60 | 60-70 | AA | Cauc. |
|---|---|---|---|---|---|---|---|---|---|---|---|
| N | 101 | 38 | 63 | 3 | 20 | 26 | 41 | 10 | 1 | 10 | 91 |
| TC | 180.69 | 179.74 | 181.27 | 197.33 | 166.80 | 185.54 | 181.71 | 185.70 | 191.00 | 173.80 | 181.45 |
| (N) | (101) | (38) | (63) | (3) | (20) | (26) | (41) | (10) | (1) | (10) | (91) |
| LDL | 96.18 | 94.32 | 97.30 | 113.00 | 93.20 | 92.69 | 100.78 | 85.80 | 111.00 | 95.50 | 96.25 |
| (N) | (101) | (38) | (63) | (3) | (20) | (26) | (41) | (10) | (1) | (10) | (91) |
| HDL | 51.37 | 55.74 | 48.73 | 60.00 | 43.50 | 52.19 | 52.00 | 59.50 | 54.00 | 58.50 | 50.58 |
| (N) | (101) | (38) | (63) | (3) | (20) | (26) | (41) | (10) | (1) | (10) | (91) |
| log (TG) | 4.958 | 4.861 | 5.017 | 4.778 | 4.801 | 5.129 | 4.888 | 5.182 | 4.875 | 4.478 | 5.011 |
| (N) | (101) | (38) | (63) | (3) | (20) | (26) | (41) | (10) | (1) | (10) | (91) |
| TC/HDL | 3.747 | 3.430 | 3.938 | 3.374 | 3.997 | 3.822 | 3.687 | 3.428 | 3.537 | 3.016 | 3.827 |
| (N) | (101) | (38) | (63) | (3) | (20) | (26) | (41) | (10) | (1) | (10) | (91) |
| Glucose | 94.14 | 91.57 | 95.68 | 91.67 | 85.42 | 93.38 | 95.03 | 109.00 | 103.00 | 115.56 | 92.00 |
| (N) | (99) | (37) | (62) | (3) | (19) | (26) | (40) | (10) | (1) | (9) | (90) |
| sBP | 117.58 | 116.84 | 118.03 | 123.33 | 116.80 | 118.04 | 115.73 | 123.80 | 118.00 | 117.80 | 117.56 |
| (N) | (101) | (38) | (63) | (3) | (20) | (26) | (41) | (10) | (1) | (10) | (91) |
| dBP | 75.40 | 74.74 | 75.79 | 71.33 | 75.20 | 76.77 | 75.10 | 74.20 | 80.00 | 78.00 | 75.11 |
| (N) | (101) | (38) | (63) | (3) | (20) | (26) | (41) | (10) | (1) | (10) | (91) |
| BM | 78.42 | 73.38 | 81.45 | 97.73 | 77.82 | 77.98 | 77.81 | 76.52 | 87.60 | 80.46 | 78.19 |
| (N) | (101) | (38) | (63) | (3) | (20) | (26) | (41) | (10) | (1) | (10) | (91) |
| BMI | 26.16 | 27.05 | 25.62 | 28.93 | 25.55 | 25.60 | 25.80 | 29.45 | 26.40 | 27.14 | 26.05 |
| (N) | (101) | (38) | (63) | (3) | (20) | (26) | (41) | (10) | (1) | (10) | (91) |

TABLE 16-continued

Risperidone Covariates

| | All | Gender | | Age | | | | | | Heritage | |
| | | female | male | <20 | 20-30 | 30-40 | 40-50 | 50-60 | 60-70 | AA | Cauc. |
|---|---|---|---|---|---|---|---|---|---|---|---|
| N | 101 | 38 | 63 | 3 | 20 | 26 | 41 | 10 | 1 | 10 | 91 |
| Waist (N) | 95.90 (100) | 95.39 (38) | 96.20 (62) | 110.33 (3) | 92.78 (20) | 92.34 (25) | 97.23 (41) | 100.50 (10) | 103.00 (1) | 92.90 (10) | 96.23 (90) |
| MSI (N) | −0.1630 (101) | −0.4377 (38) | 0.0027 (63) | −0.3383 (3) | −0.2001 (20) | −0.0747 (26) | −0.2285 (41) | −0.0295 (10) | 0.1587 (1) | −0.2807 (10) | −0.1501 (91) |

TABLE 17

Risperidone Covariate Model

| response | variable | explains | p |
|---|---|---|---|
| TC | Total | 0 | 1 |
| LDL | Total | 0 | 1 |
| HDL | Age | 0.071127 | 0.0061 |
| HDL | Gender | 0.032973 | 0.0593 |
| HDL | Heritage | 0.017908 | 0.1628 |
| HDL | Total | 0.122008 | 0.0054 |
| Log(TG) | Heritage | 0.093569 | 0.0019 |
| Log(TG) | Total | 0.093569 | 0.0019 |
| TC/HDL | Gender | 0.047232 | 0.027 |
| TC/HDL | Heritage | 0.038691 | 0.044 |
| TC/HDL | Total | 0.085923 | 0.012 |
| Glucose | Heritage | 0.084789 | 0.0027 |
| Glucose | Age | 0.042537 | 0.0313 |
| Glucose | Gender | 0.026647 | 0.0869 |
| Glucose | Total | 0.153973 | 0.0012 |
| sBP | Total | 0 | 1 |
| dBP | Total | 0 | 1 |
| BM | Gender | 0.045099 | 0.033 |
| BM | Total | 0.045099 | 0.033 |
| BMI | Total | 0 | 1 |
| Waist | Total | 0 | 1 |
| MSI | Gender | 0.039057 | 0.048 |
| MSI | Total | 0.039057 | 0.048 |

TABLE 18

Risperidone Physiotypes

| SNP | Gene | Alleles | $c_i$ |
|---|---|---|---|
| *Total Cholesterol Physiotype* | | | |
| rs2125489 | KDR | TC | −0.3801373 |
| rs3764261 | CETP | TG | −0.4035776 |
| rs417344 | LIPC | TC | −0.296332 |
| rs6809631 | PPARG | AT | −0.3617604 |
| rs2071710 | SSTR3 | AG | 0.3804884 |
| rs9288993 | DRD3 | AG | 0.6720526 |
| rs3808607 | CYP7A1 | TG | −0.3030441 |
| rs870995 | PIK3CA | AC | −0.2316652 |
| rs3791850 | GAD1 | TC | −0.2487316 |
| rs334555 | GSK3B | CG | −0.2444791 |
| Intercept (C) = 0.9291515 | | | |
| *LDL Cholesterol Physiotype* | | | |
| rs2125489 | KDR | TC | −0.2866556 |
| rs2071710 | SSTR3 | AG | 0.3482362 |
| rs3808607 | CYP7A1 | TG | −0.3589403 |
| rs916829 | ABCC8 | TC | −0.511492 |
| rs7641983 | PIK3CA | TC | 0.4339894 |
| rs231460 | PYY | TC | −0.3843004 |
| rs6700734 | TNFSF6 | AG | −0.3923427 |
| rs3846662 | HMGCR | TC | −0.1859564 |
| rs10513055 | PIK3CB | AC | 0.2796233 |
| rs1041163 | VCAM1 | TC | −0.2446807 |
| rs5896 | F2 | TC | 0.2404249 |
| Intercept (C) = 0.5145117 | | | |
| *HDL Cholesterol Physiotype* | | | |
| rs10513055 | PIK3CB | AC | 0.2480021 |
| rs1532624 | CETP | TG | 0.2902225 |
| rs849404 | PIK3CG | AG | 0.5195725 |
| rs5927 | LDLR | AG | −0.3694786 |
| rs2067477 | CHRM1 | AC | 0.4894724 |
| rs2514869 | ANGPT1 | TC | −0.3782286 |
| rs132642 | APOL3 | TA | −0.3852479 |
| rs722341 | ABCC8 | TC | 0.3323135 |
| rs10460960 | LOC391530 | AG | −0.2723704 |
| rs903361 | ADORA1 | TC | 0.1706511 |
| rs1935349 | HTR7 | AG | 0.2163707 |
| Intercept (C) = −0.3188026 | | | |
| *Log(TG) Physiotype* | | | |
| rs3764261 | CETP | TG | −0.2542046 |
| rs3791850 | GAD1 | TC | −0.3214188 |
| rs1049793 | ABP1 | GC | −0.4241085 |
| rs10890819 | ACAT1 | TC | −0.2837058 |
| rs7412 | APOE | TC | −0.5084908 |
| rs4531 | DBH | TG | 0.4592429 |
| rs686874 | HRH2 | TC | 0.6021593 |
| rs10508244 | PFKP | TC | 0.4316706 |
| rs1611115 | DBH | TC | −0.2387492 |
| Intercept (C) = 0.7350341 | | | |
| *Total Cholesterol/HDL Cholesterol Physiotype* | | | |
| rs916829 | ABCC8 | TC | −0.38656 |
| rs10513055 | PIK3CB | AC | 0.4000884 |
| rs1532624 | CETP | TG | 0.2361921 |
| rs903361 | ADORA1 | TC | 0.2572632 |
| rs1935349 | HTR7 | AG | 0.2347352 |
| rs4531 | DBH | TG | 0.2553185 |
| rs745075 | MTP | AG | 0.5495861 |
| rs11212515 | ACAT1 | AT | −0.1700176 |
| rs1801282 | PPARG | CG | −0.2432642 |
| rs11044082 | PIK3C2G | TG | −0.2452818 |
| rs521674 | ADRA2A | AT | 0.1946359 |
| rs2221223 | CHRNA7 | AC | −0.2900779 |
| Intercept (C) = −0.3738828 | | | |
| *Blood Glucose Level Physiotype* | | | |
| rs132642 | APOL3 | TA | 0.3697498 |
| rs3771892 | TNFAIP6 | AG | 0.2585305 |
| rs1040410 | DTNBP1 | TC | 0.4213591 |
| rs4149056 | SLCO1B1 | TC | −0.2990431 |
| rs10934502 | GSK3B | TC | −0.3091298 |
| rs107540 | CRHR2 | AG | 0.2128632 |
| rs1356413 | PIK3CA | GC | −0.4510575 |
| rs659734 | HTR2A | TC | −0.5185546 |
| rs446037 | APOE | AC | −1.2154331 |
| rs1801105 | HNMT | TC | −0.343568 |
| rs7247515 | AKT2 | TC | −0.3241213 |
| Intercept (C) = 0.0542416 | | | |
| *Systolic Blood Pressure Physiotype* | | | |
| rs1611115 | DBH | TC | −0.4484675 |
| rs157864 | RXRG | TC | 0.518778 |
| rs11632618 | LIPC | AG | −0.8969153 |
| rs2020933 | SLC6A4 | AT | −0.5986657 |
| rs10507383 | FLT1 | CG | −0.5564933 |
| rs3847063 | ACHE | AG | 0.2428151 |

TABLE 18-continued

| | | | |
|---|---|---|---|
| rs2278718 | MDH1 | AC | −0.3223085 |
| rs10515521 | NR3C1 | AG | 0.3152054 |
| rs4646450 | CYP3A5 | TC | −0.1882325 |
| Intercept (C) = 0.2696056 | | | |
| Diastolic Blood Pressure Physiotype | | | |
| rs334555 | GSK3B | CG | −0.3498349 |
| rs1532624 | CETP | TG | −0.3762468 |
| rs1049793 | ABP1 | GC | −0.4034175 |
| rs3847063 | ACHE | AG | 0.3500923 |
| rs7975375 | ADIPOR2 | TC | −0.4447176 |
| rs7072137 | GAD2 | AG | 0.486301 |
| rs2288911 | APOC4 | AC | 0.3057084 |
| rs6578993 | TH | TC | 0.3552778 |
| rs891087 | INSR | AG | −0.3808809 |
| rs2807071 | OAT | TC | 0.2848368 |
| rs931490 | AGTR1 | AG | 0.3419456 |
| rs3766560 | ADORA1 | AG | 0.2817746 |
| Intercept (C) = −0.224888 | | | |
| Body Mass Physiotype | | | |
| rs334555 | GSK3B | CG | −0.643725 |
| rs1801282 | PPARG | CG | −0.4141217 |
| rs7247515 | AKT2 | TC | −0.4474754 |
| rs6578993 | TH | TC | 0.3330665 |
| rs931490 | AGTR1 | AG | 0.4303632 |
| rs8179183 | LEPR | CG | 0.4333986 |
| rs235249 | TNFRSF1B | TC | 0.4165127 |
| rs1433099 | LDLR | AG | −0.3087876 |
| rs4994 | ADRB3 | TC | 0.3841408 |
| rs854572 | PON1 | CG | 0.3225061 |
| rs132653 | APOL3 | AC | −0.2718488 |
| rs2241220 | ACACB | TC | −0.1869208 |
| Intercept (C) = −0.2909216 | | | |
| Body Mass Index Physiotype | | | |
| rs334555 | GSK3B | CG | −0.4886589 |
| rs1801282 | PPARG | CG | −0.5711612 |
| rs157864 | RXRG | TC | 0.3366619 |
| rs8179183 | LEPR | CG | 0.4859235 |
| rs235249 | TNFRSF1B | TC | 0.4290026 |
| rs2734830 | UCP3 | AG | −1.4501404 |
| rs1800808 | SELP | TC | 0.4807932 |
| rs1478290 | GYS2 | TG | −0.2640122 |
| rs705381 | PON1 | TC | 0.2641122 |
| rs711752 | CETP | AG | 0.2728384 |
| rs6837793 | NPY5R | AG | −0.3096726 |
| rs1001293 | APOL2 | TC | 0.3064519 |
| rs6078 | LIPC | AG | 0.4611091 |
| rs3853188 | SCARB2 | AC | −0.2837581 |
| Intercept (C) = −0.4313253 | | | |
| Waist circumference Physiotype | | | |
| rs334555 | GSK3B | CG | 0.2984838 |
| rs1611115 | DBH | TC | 0.291663 |
| rs2807071 | OAT | TC | −0.2409202 |
| rs931490 | AGTR1 | AG | −0.2927931 |
| rs8179183 | LEPR | CG | −0.375565 |
| rs705381 | PON1 | TC | −0.3001027 |
| rs6837793 | NPY5R | AG | 0.358247 |
| rs1001293 | APOL2 | TC | −0.6563472 |
| rs6078 | LIPC | AG | −0.4646088 |
| rs10841044 | PIK3C2G | TG | 0.2123296 |
| rs6136 | SELP | AC | 0.3367276 |
| rs2076672 | APOL5 | TC | −0.2426366 |
| rs5092 | APOA4 | AG | −0.2191696 |
| Intercept (C) = 0.4007562 | | | |
| Metabolic Syndromes Index (MSI) Physiotype | | | |
| rs849404 | PIK3CG | AG | 0.2275768 |
| rs1935349 | HTR7 | AG | 0.3878974 |
| rs1049793 | ABP1 | GC | −0.3217375 |
| rs7412 | APOE | TC | −0.422049 |
| rs1611115 | DBH | TC | −0.2517752 |
| rs11212515 | ACAT1 | AT | −0.2356584 |
| rs1801282 | PPARG | CG | −0.3273775 |
| rs7247515 | AKT2 | TC | −0.3867755 |
| rs6578993 | TH | TC | 0.2736106 |
| rs2807071 | OAT | TC | 0.2293947 |
| rs931490 | AGTR1 | AG | 0.312779 |
| rs8179183 | LEPR | CG | 0.3293557 |
| rs1433099 | LDLR | AG | −0.3123375 |
| rs2241220 | ACACB | TC | −0.1865932 |
| rs1001293 | APOL2 | TC | 0.3027646 |
| Intercept (C) = 0.3366409 | | | |

TABLE 19

Ziprasidone Covariates

| | | Gender | | Age | | | | | | Heritage | |
|---|---|---|---|---|---|---|---|---|---|---|---|
| | All | female | male | <20 | 20-30 | 30-40 | 40-50 | 50-60 | 60-70 | AA | Cauc. |
| N | 37 | 18 | 19 | 2 | 10 | 12 | 11 | 1 | 1 | 6 | 31 |
| TC | 172.14 | 186.39 | 158.63 | 176.00 | 159.20 | 180.17 | 161.27 | 220.00 | 269.00 | 145.17 | 177.35 |
| (N) | (37) | (18) | (19) | (2) | (10) | (12) | (11) | (1) | (1) | (6) | (31) |
| LDL | 88.32 | 98.11 | 79.05 | 89.50 | 79.20 | 98.42 | 75.18 | 135.00 | 154.00 | 63.17 | 93.19 |
| (N) | (37) | (18) | (19) | (2) | (10) | (12) | (11) | (1) | (1) | (6) | (31) |
| HDL | 51.86 | 54.17 | 49.68 | 60.00 | 51.90 | 48.17 | 54.45 | 57.00 | 46.00 | 56.33 | 51.00 |
| (N) | (37) | (18) | (19) | (2) | (10) | (12) | (11) | (1) | (1) | (6) | (31) |
| log (TG) | 4.97 | 5.039 | 4.900 | 4.852 | 4.783 | 4.925 | 5.127 | 4.934 | 5.852 | 4.996 | 4.963 |
| (N) | (37) | (18) | (19) | (2) | (10) | (12) | (11) | (1) | (1) | (6) | (31) |
| TC/HDL | 3.49 | 3.57 | 3.417 | 3.083 | 3.161 | 3.914 | 3.158 | 3.860 | 5.848 | 2.705 | 3.644 |
| (N) | (37) | (18) | (19) | (2) | (10) | (12) | (11) | (1) | (1) | (6) | (31) |
| Glucose | 92.78 | 93.82 | 91.84 | 98.00 | 87.10 | 90.25 | 100.73 | 82.00 | NA | 96.67 | 92.00 |
| (N) | (36) | (17) | (19) | (2) | (10) | (12) | (11) | (1) | | (6) | (30) |
| sBP | 119.51 | 117.78 | 121.16 | 106.00 | 118.80 | 120.67 | 121.09 | 122.00 | 120.00 | 130.00 | 117.48 |
| (N) | (37) | (18) | (19) | (2) | (10) | (12) | (11) | (1) | (1) | (6) | (31) |
| dBP | 76.16 | 74.56 | 77.68 | 67.00 | 73.40 | 76.17 | 81.09 | 64.00 | 80.00 | 81.33 | 75.16 |
| (N) | (37) | (18) | (19) | (2) | (10) | (12) | (11) | (1) | (1) | (6) | (31) |
| BM | 88.09 | 84.5 | 91.49 | 87.75 | 86.76 | 81.85 | 98.45 | 67.30 | 83.70 | 93.60 | 87.02 |
| (N) | (37) | (18) | (19) | (2) | (10) | (12) | (11) | (1) | (1) | (6) | (31) |
| BMI | 29.66 | 30.87 | 28.52 | 33.20 | 29.31 | 27.99 | 31.85 | 23.20 | 28.60 | 32.58 | 29.10 |
| (N) | (37) | (18) | (19) | (2) | (10) | (12) | (11) | (1) | (1) | (6) | (31) |
| Waist | 102.04 | 101.06 | 102.96 | 105.50 | 97.46 | 96.11 | 112.99 | 77.50 | 116.00 | 111.72 | 100.16 |
| (N) | (37) | (18) | (19) | (2) | (10) | (12) | (11) | (1) | (1) | (6) | (31) |
| MSI | 0.0383 | 79.053 | 0.1326 | −0.5870 | −0.4351 | −0.1184 | 0.6624 | −1.7497 | 2.8249 | 0.4766 | −0.0465 |
| (N) | (37) | (18) | (19) | (2) | (10) | (12) | (11) | (1) | (1) | (6) | (31) |

TABLE 20

Ziprasidone Covariate Model

| response | variable | explains | p |
|---|---|---|---|
| TC | Gender | 0.109776 | 0.037 |
| TC | Age | 0.066934 | 0.1 |
| TC | Heritage | 0.054311 | 0.136 |
| TC | Total | 0.23102 | 0.032 |
| LDL | Heritage | 0.091709 | 0.065 |
| LDL | Gender | 0.049213 | 0.172 |
| LDL | Total | 0.140922 | 0.076 |
| HDL | Total | 0 | 1 |
| log(TG) | Age | 0.075516 | 0.1 |
| log(TG) | Total | 0.075516 | 0.1 |
| TC/HDL | Heritage | 0.083355 | 0.083 |
| TC/HDL | Total | 0.083355 | 0.083 |
| Glucose | Total | 0 | 1 |
| sBP | Heritage | 0.140144 | 0.022 |
| sBP | Total | 0.140144 | 0.022 |
| dBP | Age | 0.062036 | 0.13 |
| dBP | Heritage | 0.061409 | 0.13 |
| dBP | Total | 0.123445 | 0.11 |
| BM | Total | 0 | 1 |
| BMI | Total | 0 | 1 |
| Waist | Heritage | 0.066736 | 0.12 |
| Waist | Age | 0.05904 | 0.14 |
| Waist | Total | 0.125776 | 0.1 |
| MSI | Age | 0.134986 | 0.025 |
| MSI | Total | 0.134986 | 0.025 |

TABLE 21

Ziprasidone Physiotpyes

| SNP | Gene | Allele | |
|---|---|---|---|
| *Total Cholesterol Physiotype* | | | |
| rs5085 | APOA2 | GC | −0.1976552 |
| rs2856929 | PKM2 | AG | 0.3291855 |
| rs2228139 | IL1R1 | GC | 2.0668791 |
| rs6967107 | WBSCR14 | AC | 1.0802695 |
| rs1415793 | ADORA3 | AG | 0.8220207 |
| rs762551 | CYP1A2 | AC | 0.4197551 |
| rs6976017 | CYP3A5 | AC | −0.7672715 |
| rs6700734 | TNFSF6 | AG | −0.2607411 |
| Intercept (C) = −0.7291502 | | | |
| *LDL Cholesterol Physiotype* | | | |
| rs2856929 | PKM2 | AG | 0.2860976 |
| rs2228139 | IL1R1 | GC | 1.30876234 |
| rs6967107 | WBSCR14 | AC | 1.16126538 |
| rs6700734 | TNFSF6 | AG | −0.51431591 |
| rs2301108 | HIF1A | AG | −0.95392249 |
| rs7816340 | ADRA1A | TC | 1.00702348 |
| rs40318 | PIK3R1 | TC | −0.56923672 |
| rs10082776 | RARG | AG | 0.20552934 |
| Intercept (C) = −0.04978917 | | | |
| *HDL Cholesterol Physiotype* | | | |
| rs5085 | APOA2 | GC | 0.3538266 |
| rs4531 | DBH | TG | 0.8572798 |
| rs12691940 | HNMT | AG | 0.553912 |
| rs1001293 | APOL2 | TC | 0.7004438 |
| rs3757868 | ACHE | AG | 0.5545349 |
| rs10841044 | PIK3C2G | TG | −0.4058614 |
| Intercept (C) = −0.887848 | | | |
| *Log(TG) Physiotype* | | | |
| rs2856929 | PKM2 | AG | 0.5995107 |
| rs2807071 | OAT | TC | −0.5414189 |
| rs675 | APOA4 | TA | 0.4093944 |
| rs1801253 | ADRB1 | GC | −0.240143 |
| rs10460960 | LOC391530 | AG | 0.3661926 |
| rs1058046 | PYY | CG | −0.574242 |
| rs324651 | CHRM2 | TG | −0.3865682 |
| rs6960931 | PRKAG2 | TC | 0.3268052 |
| Intercept (C) = 0.1462115 | | | |
| *Total Cholesterol/HDL Cholesterol Physiotype* | | | |
| rs2856929 | PKM2 | AG | 0.6203526 |
| rs3757868 | ACHE | AG | 0.6158538 |
| rs916829 | ABCC8 | TC | −0.7555133 |
| rs1322783 | DISC1 | TC | 0.636995 |
| rs10509676 | CYP2C19 | TA | −0.1901375 |
| rs3822222 | CCKAR | TC | −0.4005971 |
| Intercept (C) = −0.259638 | | | |
| *Blood Glucose Level Physiotype* | | | |
| rs1801253 | ADRB1 | GC | −0.3829259 |
| rs3808607 | CYP7A1 | TG | 0.5196444 |
| rs5369 | EDN1 | AG | −0.301745 |
| rs1058167 | CYP2D6 | TC | −0.3109408 |
| rs3917550 | PON1 | TC | 0.5669915 |
| rs1041163 | VCAM1 | TC | 0.3472771 |
| rs235249 | TNFRSF1B | TC | −0.3901891 |
| rs5950584 | LOC441514 | TG | −0.2950186 |
| Intercept (C) = 0.1538298 | | | |
| *Systolic Blood Pressure Physiotype* | | | |
| rs2856929 | PKM2 | AG | 0.27182897 |
| rs324651 | CHRM2 | TG | −0.52271193 |
| rs26312 | GHRL | AG | −0.57374919 |
| rs2076672 | APOL5 | TC | −0.16423581 |
| rs931992 | TCAP | AC | 0.21406474 |
| rs3791981 | APOB | AG | −0.79622137 |
| rs1029947 | PRKAG2 | AG | 0.49981286 |
| rs107540 | CRHR2 | AG | 0.29001894 |
| rs2067477 | CHRM1 | AC | −0.25408548 |
| Intercept (C) = 0.01811896 | | | |
| *Diastolic Blood Pressure Physiotype* | | | |
| rs4765623 | SCARB1 | TG | 0.4327264 |
| rs3816873 | MTP | TC | −0.3898652 |
| rs1800783 | NOS3 | TA | −0.3080836 |
| rs2867383 | DRD5 | AG | 0.323809 |
| Intercept (C) = −0.2116728 | | | |
| *Body Mass Physiotype* | | | |
| rs324651 | CHRM2 | TG | −0.7514575 |
| rs4765623 | SCARB1 | TC | 0.4370727 |
| rs1468271 | NPY | AG | −3.33548 |
| rs5927 | LDLR | AG | 0.4545137 |
| rs1438732 | NR3C1 | CG | 0.3307272 |
| rs1800808 | SELP | TC | 0.4240058 |
| Intercept (C) = −0.5308041 | | | |
| *Body Mass Index Physiotype* | | | |
| rs2807071 | OAT | TC | −0.38108779 |
| rs1801253 | ADRB1 | GC | −0.5765789 |
| rs1468271 | NPY | AG | −1.09542135 |
| rs439401 | APOE | TC | 0.62485469 |
| rs5092 | APOA4 | AG | −0.57861064 |
| rs3750546 | RXRA | AG | 0.34021279 |
| rs10508244 | PFKP | TC | 0.85307048 |
| Intercept (C) = 0.08505914 | | | |
| *Waist circumference Physiotype* | | | |
| rs2856929 | PKM2 | AG | −0.4149646 |
| rs1801253 | ADRB1 | GC | 0.2234329 |
| rs6196 | NR3C1 | AG | −0.5146913 |
| rs10515521 | NR3C1 | AG | −0.4591251 |
| rs4726107 | LOC441301 | TC | −0.3893138 |
| rs2269935 | PFKM | AC | 0.4404594 |
| rs1871143 | GYS2 | TG | −0.4088495 |
| rs1283718 | ANGPT1 | TG | 0.7653365 |
| rs894251 | SCARB2 | TC | −0.4765622 |
| Intercept (C) = 0.4750982 | | | |

TABLE 21-continued

Metabolic Syndromes Index (MSI) Physiotype

| | | | |
|---|---|---|---|
| rs2856929 | PKM2 | AG | 0.5948673 |
| rs2807071 | OAT | TC | −0.5883151 |
| rs1801253 | ADRB1 | GC | −0.3782497 |
| rs6196 | NR3C1 | AG | 0.5467795 |
| rs1877394 | PIK3C2B | AG | 1.547238 |
| rs2429511 | ADRB1 | AG | 0.2352037 |

Intercept (C) = −0.3147052

TABLE 22

Drug Class Covariates

| | | Drug | | | | | | Heritage | | | |
|---|---|---|---|---|---|---|---|---|---|---|---|
| N | All 347 | arapiprazole 36 | clozapine 11 | olanzapine 67 | quetiapine 95 | risperidone 101 | ziprasidone 37 | AA 43 | Cauc. 299 | Hispanic 2 | Other 3 |
| TC | 185.69 | 179.78 | 197.09 | 192.60 | 192.33 | 180.69 | 172.14 | 183.23 | 186.08 | 212.50 | 163.67 |
| (N) | (347) | (36) | (11) | (67) | (95) | (101) | (37) | (43) | (299) | (2) | (3) |
| LDL | 96.93 | 93.47 | 104.33 | 104.11 | 96.71 | 96.18 | 88.32 | 96.47 | 96.88 | 147.00 | 92.00 |
| (N) | (343) | (36) | (9) | (66) | (94) | (101) | (37) | (43) | (296) | (1) | (3) |
| HDL | 50.43 | 51.75 | 44.18 | 49.45 | 49.79 | 51.37 | 51.86 | 54.07 | 49.98 | 44.50 | 47.00 |
| (N) | (347) | (36) | (11) | (67) | (95) | (101) | (37) | (43) | (299) | (2) | (3) |
| Log (TG) | 5.09 | 5.045 | 5.430 | 5.072 | 5.263 | 4.958 | 4.968 | 4.954 | 5.110 | 5.438 | 4.621 |
| (N) | (347) | (36) | (11) | (67) | (95) | (101) | (37) | (43) | (299) | (2) | (3) |
| TC/HDL | 3.91 | 3.808 | 4.773 | 4.145 | 4.023 | 3.747 | 3.491 | 3.467 | 3.966 | 4.800 | 4.067 |
| (N) | (346) | (36) | (11) | (67) | (94) | (101) | (37) | (42) | (299) | (2) | (3) |
| Glucose | 93.26 | 95.29 | 102.73 | 91.22 | 92.08 | 94.14 | 92.78 | 99.95 | 92.26 | 92.50 | 100.33 |
| (N) | (341) | (35) | (11) | (65) | (95) | (99) | (36) | (41) | (295) | (2) | (3) |
| sBP | 119.41 | 122.17 | 126.18 | 118.58 | 120.07 | 117.58 | 119.51 | 121.95 | 119.09 | 122.00 | 113.33 |
| (N) | (347) | (36) | (11) | (67) | (95) | (101) | (37) | (43) | (299) | (2) | (3) |
| dBP | 75.78 | 75.86 | 82.00 | 76.12 | 75.04 | 75.40 | 76.16 | 76.67 | 75.52 | 83.00 | 84.33 |
| (N) | (347) | (36) | (11) | (67) | (95) | (101) | (37) | (43) | (299) | (2) | (3) |
| BM | 83.98 | 86.58 | 93.22 | 82.90 | 87.05 | 78.42 | 88.09 | 88.44 | 83.43 | 96.14 | 66.21 |
| (N) | (345) | (35) | (11) | (67) | (94) | (101) | (37) | (43) | (297) | (2) | (3) |
| BMI | 27.97 | 28.56 | 29.45 | 27.12 | 29.44 | 26.16 | 29.66 | 29.05 | 27.82 | 33.20 | 23.49 |
| (N) | (347) | (36) | (11) | (67) | (95) | (101) | (37) | (43) | (299) | (2) | (3) |
| Waist | 99.53 | 101.34 | 105.08 | 98.21 | 102.05 | 95.90 | 102.04 | 99.69 | 99.47 | 119.00 | 90.33 |
| (N) | (344) | (36) | (11) | (67) | (93) | (100) | (37) | (43) | (296) | (2) | (3) |
| Msi. N | 347 | 36 | 11 | 67 | 95 | 101 | 37 | 43 | 299 | 2 | 3 |
| MSI | 0.0204 | 0.0619 | 0.3259 | −0.1290 | 0.2625 | −0.1630 | 0.0383 | −0.0240 | 0.0270 | 0.8483 | −0.5532 |
| (N) | (347) | (36) | (11) | (67) | (95) | (101) | (37) | (43) | (299) | (2) | (3) |

| | Gender | | Age | | | | | | | Site | |
|---|---|---|---|---|---|---|---|---|---|---|---|
| N | female 125 | Male 222 | <20 12 | 20-30 82 | 30-40 117 | 40-50 106 | 50-60 24 | 60-70 5 | 70-80 1 | Population A 25 | Population B 322 |
| TC | 187.73 | 184.54 | 169.83 | 177.11 | 191.27 | 187.28 | 185.25 | 204.60 | 174.00 | 195.12 | 184.96 |
| (N) | (125) | (222) | (12) | (82) | (117) | (106) | (24) | (5) | (1) | (25) | (322) |
| LDL | 97.53 | 96.60 | 90.50 | 93.54 | 99.55 | 97.96 | 92.54 | 105.80 | 94.00 | 115.52 | 95.60 |
| (N) | (122) | (221) | (12) | (80) | (117) | (104) | (24) | (5) | (1) | (23) | (320) |
| HDL | 53.50 | 48.70 | 49.75 | 48.46 | 49.16 | 52.06 | 56.50 | 46.80 | 68.00 | 45.20 | 50.84 |
| (N) | (125) | (222) | (12) | (82) | (117) | (106) | (24) | (5) | (1) | (25) | (322) |
| Log (TG) | 5.02 | 5.13 | 4.87 | 5.02 | 5.20 | 5.03 | 5.09 | 5.52 | 4.16 | 5.10 | 5.09 |
| (N) | (125) | (222) | (12) | (82) | (117) | (106) | (24) | (5) | (1) | (25) | (322) |
| TC/HDL | 3.73 | 4.01 | 3.70 | 3.87 | 4.13 | 3.82 | 3.46 | 4.42 | 2.56 | 4.70 | 3.85 |
| (N) | (125) | (221) | (12) | (82) | (116) | (106) | (24) | (5) | (1) | (25) | (321) |
| Glucose | 95.05 | 92.28 | 93.25 | 85.74 | 93.06 | 97.33 | 100.83 | 100.50 | 92.00 | 100.00 | 92.75 |
| (N) | (121) | (220) | (12) | (81) | (115) | (104) | (24) | (4) | (1) | (24) | (317) |
| sBP | 117.24 | 120.64 | 118.67 | 118.91 | 120.27 | 117.43 | 125.63 | 125.20 | 100.00 | 121.60 | 119.24 |
| (N) | (125) | (222) | (12) | (82) | (117) | (106) | (24) | (5) | (1) | (25) | (322) |
| dBP | 74.94 | 76.25 | 69.50 | 74.65 | 76.65 | 75.93 | 77.38 | 80.00 | 66.00 | 81.40 | 75.34 |
| (N) | (125) | (222) | (12) | (82) | (117) | (106) | (24) | (5) | (1) | (25) | (322) |
| BM | 79.55 | 86.49 | 90.32 | 81.65 | 84.66 | 84.94 | 82.90 | 83.42 | 44.40 | 88.15 | 83.65 |
| (N) | (125) | (220) | (12) | (81) | (116) | (106) | (24) | (5) | (1) | (25) | (320) |
| BMI | 29.61 | 27.04 | 27.58 | 26.82 | 28.40 | 28.26 | 29.26 | 27.52 | 15.90 | 28.73 | 27.91 |
| (N) | (125) | (222) | (12) | (82) | (117) | (106) | (24) | (5) | (1) | (25) | (322) |
| Waist | 98.88 | 99.90 | 97.83 | 95.86 | 98.96 | 102.43 | 102.56 | 108.60 | 65.00 | 104.60 | 99.14 |
| (N) | (123) | (221) | (12) | (82) | (115) | (105) | (24) | (5) | (1) | (25) | (319) |
| MSI | −0.1015 | 0.0890 | −0.5657 | −0.2611 | 0.1609 | 0.0992 | 0.0975 | 1.2208 | −2.5194 | 1.20E−10 | 0.0219 |
| (N) | (125) | (222) | (12) | (82) | (117) | (106) | (24) | (5) | (1) | (25) | (322) |

TABLE 23

Drug Class Covariate Model

| response | variable | explains | p |
|---|---|---|---|
| TC | Age | 0.009377 | 0.069 |
| TC | Drug | 0.031006 | 0.054 |
| TC | Total | 0.040383 | 0.029 |
| LDL | Site | 0.021482 | 0.0065 |
| LDL | Total | 0.021482 | 0.0065 |
| HDL | Gender | 0.027673 | 0.0017 |
| HDL | Age | 0.016219 | 0.0159 |
| HDL | Site | 0.008846 | 0.0744 |
| HDL | Total | 0.052738 | 0.00033 |
| Log(TG) | Drug | 0.061649 | 0.00049 |
| Log(TG) | Gender | 0.007385 | 0.09942 |
| Log(TG) | Heritage | 0.019257 | 0.07018 |
| Log(TG) | Total | 0.088291 | 0.00025 |
| TC/HDL | Site | 0.029554 | 0.0012 |
| TC/HDL | Gender | 0.011176 | 0.0448 |
| TC/HDL | Heritage | 0.022478 | 0.0445 |
| TC/HDL | Total | 0.063208 | 0.00046 |
| Glucose | Age | 0.055834 | 9.20E-06 |
| Glucose | Site | 0.013631 | 0.027 |
| Glucose | Total | 0.069465 | 5.20E-06 |
| sBP | Gender | 0.020525 | 0.0075 |
| sBP | Total | 0.020525 | 0.0075 |
| dBP | Site | 0.033199 | 0.00058 |
| dBP | Age | 0.015677 | 0.01751 |
| dBP | Gender | 0.007616 | 0.09704 |
| dBP | Total | 0.056492 | 0.00017 |
| BM | Gender | 0.024759 | 0.003 |
| BM | Drug | 0.038853 | 0.017 |
| BM | Total | 0.063612 | 0.001 |
| BMI | Gender | 0.03338 | 0.00052 |
| BMI | Drug | 0.043379 | 0.00782 |
| BMI | Total | 0.076759 | 0.00013 |
| Waist | Age | 0.017124 | 0.014 |
| Waist | Drug | 0.035066 | 0.03 |
| Waist | Site | 0.007396 | 0.105 |
| Waist | Total | 0.059586 | 0.0041 |
| MSI | Age | 0.016455 | 0.017 |
| MSI | Gender | 0.008013 | 0.094 |
| MSI | Total | 0.024468 | 0.014 |

TABLE 24

Drug Class Physiotypes

| SNP | Gene | Alleles | $c_i$ |
|---|---|---|---|
| Total Cholesterol Physiotype | | | |
| rs2125489 | KDR | TC | -0.3329473 |
| rs6700734 | TNFSF6 | AG | -0.1974675 |
| rs9659997 | HTR6 | TC | -0.1852197 |
| rs3816873 | MTP | TC | 0.2138725 |
| rs6967107 | WBSCR14 | AC | 0.2562421 |
| rs2228502 | CPT1A | TC | -0.2992433 |
| rs5368 | SELE | TC | -0.1792623 |
| rs3756450 | SLC6A3 | TC | -0.1570249 |
| rs4646450 | CYP3A5 | TC | 0.1692742 |
| rs3791981 | APOB | AG | -0.1852733 |
| Intercept (C) = 0.3121911 | | | |
| LDL Cholesterol Physiotype | | | |
| rs2125489 | KDR | TC | -0.4837954 |
| rs6700734 | TNFSF6 | AG | -0.2634916 |
| rs3816873 | MTP | TC | 0.2639484 |
| rs6967107 | WBSCR14 | AC | 0.3306828 |
| rs3791981 | APOB | AG | -0.2470483 |
| rs686874 | HRH2 | TC | -0.6009673 |
| rs908867 | BDNF | AG | 0.3311764 |
| rs1176744 | HTR3B | TG | -0.2013788 |
| rs1045642 | ABCB1 | TC | 0.1932343 |
| rs5030390 | ICAM1 | AG | 0.2941507 |
| rs7412 | APOE | TC | 0.1905266 |
| rs1468271 | NPY | AG | -0.3038671 |
| rs264 | LPL | AG | 0.1953161 |
| rs3808607 | CYP7A1 | TG | -0.1629919 |
| rs40318 | PIK3R1 | TC | -0.2466071 |
| Intercept (C) = 0.1181403 | | | |
| HDL Cholesterol Physiotype | | | |
| rs264 | LPL | AG | 0.3034764 |
| rs4727666 | PIK3CG | AG | 0.1505281 |
| rs1935349 | HTR7 | AG | 0.2189365 |
| rs1057910 | CYP2C9 | AC | -0.2666764 |
| rs10515521 | NR3C1 | AG | 0.2922776 |
| rs1046668 | TNFAIP6 | AG | 0.1507264 |
| rs2298191 | ADORA3 | TC | -0.1587168 |
| rs676643 | HTR1D | AG | -0.1174074 |
| rs136163 | APOL1 | TG | 0.2012396 |
| rs2162189 | SST | AG | 0.1943337 |
| rs10890819 | ACAT1 | TC | -0.4679513 |
| rs1396862 | CRHR1 | TC | -0.1120195 |
| rs1532624 | CETP | TG | 0.295775 |
| rs2076672 | APOL5 | TC | -0.1013606 |
| rs7072137 | GAD2 | AG | 0.3479085 |
| rs1801282 | PPARG | CG | -0.1342516 |
| rs814628 | LIPF | AG | -0.1233003 |
| rs11212515 | ACAT1 | AT | 0.3603799 |
| Intercept (C) = -0.354794 | | | |
| Log(TG) Physiotype | | | |
| rs4646450 | CYP3A5 | TC | 0.1533167 |
| rs686874 | HRH2 | TC | 0.381515 |
| rs11212515 | ACAT1 | AT | -0.1104332 |
| rs6078 | LIPC | AG | -0.5830399 |
| rs4333 | ACE | TC | -0.1897409 |
| rs2838549 | PFKL | AG | 0.1830463 |
| rs2229169 | ADRA2B | AC | -0.1485697 |
| rs3791850 | GAD1 | TC | -0.1690057 |
| rs2276307 | HTR3B | AG | -0.1569379 |
| rs3756007 | GABRA2 | TC | -0.3040296 |
| rs11188092 | CYP2C19 | AC | 0.1419675 |
| rs2292459 | PIK3C2B | TC | 0.2584414 |
| Intercept (C) = 0.3359689 | | | |
| Total Cholesterol/HDL Cholesterol Physiotype | | | |
| rs3816873 | MTP | TC | 0.18171605 |
| rs2228502 | CPT1A | TC | -0.37859759 |
| rs3756450 | SLC6A3 | TC | -0.30672439 |
| rs4646450 | CYP3A5 | TC | 0.24912084 |
| rs1468271 | NPY | AG | -0.35918854 |
| rs264 | LPL | AG | 0.31643886 |
| rs1935349 | HTR7 | AG | 0.16409433 |
| rs10890819 | ACAT1 | TC | -0.22083525 |
| rs1532624 | CETP | TG | 0.18444396 |
| rs7072137 | GAD2 | AG | 0.1663205 |
| rs2301108 | HIF1A | AG | -0.31456751 |
| rs916829 | ABCC8 | TC | -0.31334971 |
| rs6586179 | LIPA | TC | -0.2942351 |
| rs3762272 | PKLR | AG | -0.5867706 |
| rs854572 | PON1 | CG | -0.12921136 |
| rs5369 | EDN1 | AG | 0.17941353 |
| rs701492 | GAD1 | TC | 0.16157623 |
| Intercept (C) = -0.01927497 | | | |
| Blood Glucose Level Physiotype | | | |
| rs3176921 | CRH | TC | -0.1887726 |
| rs2241220 | ACACB | TC | -0.3367315 |
| rs2229126 | ADRA1A | AT | -0.5889842 |
| rs5742612 | IGF1 | TC | -0.4651724 |
| rs877172 | OXT | AC | -0.2027319 |
| rs659734 | HTR2A | TC | -0.4018043 |
| rs2240403 | CRHR2 | TC | 0.2194478 |
| rs1801278 | IRS1 | AG | -0.2359617 |
| rs446037 | APOE | AC | -0.674555 |
| rs10934502 | GSK3B | TC | -0.1100436 |
| Intercept (C) = 0.4948069 | | | |
| Systolic Blood Pressure Physiotype | | | |
| rs4784642 | GNAO1 | AG | 0.1795747 |
| rs707922 | APOM | AC | -0.2118805 |
| rs1556478 | LIPA | AG | -0.1361368 |
| rs931992 | TCAP | AC | 0.2185462 |
| rs3853188 | SCARB2 | AC | -0.2953437 |

TABLE 24-continued

| | | | |
|---|---|---|---|
| rs2515449 | MCPH1 | AG | 0.3202011 |
| rs1800206 | PPARA | GC | 0.3432863 |
| rs3847063 | ACHE | AG | 0.1398181 |
| rs5880 | CETP | CG | −0.2750663 |
| rs1143634 | IL1B | TC | 0.135475 |
| rs1001293 | APOL2 | TC | −0.1591774 |

Intercept (C) = −0.3694449

Diastolic Blood Pressure Physiotype

| | | | |
|---|---|---|---|
| rs2229169 | ADRA2B | AC | −0.2655956 |
| rs5742612 | IGF1 | TC | −0.3361136 |
| rs10934502 | GSK3B | TC | −0.2210137 |
| rs4784642 | GNAO1 | AG | 0.1004943 |
| rs707922 | APOM | AC | −0.3548184 |
| rs931992 | TCAP | AC | 0.1906588 |
| rs2287754 | GYS1 | AG | 0.4584279 |
| rs711752 | CETP | AG | −0.1721751 |
| rs1801253 | ADRB1 | GC | −0.2122918 |
| rs11632618 | LIPC | AG | 0.3791051 |
| rs3769671 | POMC | AC | 0.3346736 |
| rs2033447 | RARB | TC | 0.1366534 |
| rs6578993 | TH | TC | 0.1497807 |

Intercept (C) = 0.1495525

Body Mass Physiotype

| | | | |
|---|---|---|---|
| rs1046668 | TNFAIP6 | AG | −1.4470851 |
| rs676643 | HTR1D | AG | −0.1836599 |
| rs854572 | PON1 | CG | −0.2708988 |
| rs10934502 | GSK3B | TC | −0.1856543 |
| rs2515449 | MCPH1 | AG | 0.2743354 |
| rs1801253 | ADRB1 | GC | −0.2065415 |
| rs405509 | APOE | AC | 0.1911381 |
| rs3810947 | CHAT | AG | −0.1931362 |
| rs3771892 | TNFAIP6 | AG | 1.7033878 |
| rs1356413 | PIK3CA | GC | −0.3041636 |
| rs324651 | CHRM2 | TG | −0.2784111 |
| rs235249 | TNFRSF1B | TC | 0.2069807 |
| rs3760396 | CCL2 | GC | −0.2424399 |
| rs4890109 | RARA | TG | 0.3664227 |
| rs903361 | ADORA1 | TC | −0.1727613 |
| rs6032470 | GHRH | TC | −0.180161 |
| rs1190762 | GNAO1 | AC | −0.2385288 |
| rs619698 | SSTR5 | AC | −0.1211843 |
| rs132653 | APOL3 | AC | −0.1713454 |

Intercept (C) = 0.7147183

Body Mass Index Physiotype

| | | | |
|---|---|---|---|
| rs4784642 | GNAO1 | AG | 0.1179121 |
| rs3853188 | SCARB2 | AC | −0.2427783 |
| rs2515449 | MCPH1 | AG | 0.3246919 |
| rs1801253 | ADRB1 | GC | −0.2015267 |
| rs405509 | APOE | AC | 0.0991574 |
| rs1356413 | PIK3CA | GC | −0.2884954 |
| rs3760396 | CCL2 | GC | −0.2726638 |
| rs4890109 | RARA | TG | 0.6160047 |
| rs619698 | SSTR5 | AC | −0.2063694 |
| rs5092 | APOA4 | AG | 0.152005 |
| rs1549758 | NOS3 | TC | −0.2188535 |
| rs10513055 | PIK3CB | AC | 0.2181249 |
| rs10515070 | PIK3R1 | AT | −0.1894383 |
| rs1058046 | PYY | CG | −0.1592878 |
| rs2740574 | CYP3A4 | AG | −0.1699935 |
| rs5896 | F2 | TC | −0.2374929 |

Intercept (C) = 0.4406539

Waist circumference Physiotype

| | | | |
|---|---|---|---|
| rs5742612 | IGF1 | TC | 0.3487992 |
| rs10934502 | GSK3B | TC | 0.1883028 |
| rs707922 | APOM | AC | −0.2398071 |
| rs2515449 | MCPH1 | AG | −0.3701831 |
| rs405509 | APOE | AC | −0.1786070 |
| rs1356413 | PIK3CA | GC | 0.3260912 |
| rs324651 | CHRM2 | TG | 0.2254508 |
| rs4890109 | RARA | TG | −0.4570859 |
| rs619698 | SSTR5 | AC | 0.1696043 |
| rs1058046 | PYY | CG | 0.1236385 |
| rs5896 | F2 | TC | 0.2397378 |
| rs2071521 | APOC3 | TC | −0.1667782 |
| rs6196 | NR3C1 | AG | −0.1978903 |
| rs8179183 | LEPR | CG | −0.1781411 |

TABLE 24-continued

| | | | |
|---|---|---|---|
| rs7975375 | ADIPOR2 | TC | 0.1476221 |
| rs140700 | SLC6A4 | AG | −0.2103497 |
| rs3024492 | IL10 | TA | −0.1167672 |

Intercept (C) = 0.1568334

Metabolic Syndromes Index (MSI) Physiotype

| | | | |
|---|---|---|---|
| rs686874 | HRH2 | TC | 0.3220468 |
| rs1468271 | NPY | AG | −0.33210411 |
| rs1046668 | TNFAIP6 | AG | 0.18655945 |
| rs7072137 | GAD2 | AG | 0.18646334 |
| rs11212515 | ACAT1 | AT | −0.15704565 |
| rs2229169 | ADRA2B | AC | −0.24932255 |
| rs5742612 | IGF1 | TC | −0.54721533 |
| rs10934502 | GSK3B | TC | −1.45357306 |
| rs2515449 | MCPH1 | AG | 0.34710956 |
| rs1356413 | PIK3CA | GC | −0.41024475 |
| rs619698 | SSTR5 | AC | −0.14659614 |
| rs10513055 | PIK3CB | AC | 0.14849687 |
| rs8179183 | LEPR | CG | 0.15984034 |
| rs2429511 | ADRB1 | AG | 0.14696402 |
| rs4792887 | CRHR1 | TC | 0.2020858 |
| rs4688046 | GSK3B | TC | 1.30193623 |

Intercept (C) = 0.08296655

Example 3

One patient's Physiotype for some of these physiological responses may be expressed. The values of each $c_i$ are given above or may be determined in accordance with the procedure set forth herein. The patient's genotype (0, 1, or 2) is multiplied by the coefficient corresponding to the effect of the particular on a particular response.

For each response, the sum $$\sum_i c_i g_i$$

is added to the intercept value C to determine the predicted response to psychotropic drugs for the patient. The patient's physiotype may be expressed in a convenient format for the practitioner's assessment of a patient's likely response to psychotropic drugs.

The physiotype report predicts and models the individual's innate physiological metabolic response to psychotropic drugs. These predictions are independent of baseline status. The ability to isolate the pure genetic contribution to metabolic syndromes in response to psychotropic drugs will be useful to the practitioner, especially in scenarios where baseline data may be difficult to obtain. This type of report enables a patient and physician to evaluate innate physiological capacity and to recommend a particular drug. For example, a given baseline measurement may not be clinically feasible if it is certain to be confounded with other factors. In such situations, the physiotype model can be utilized to predict the person's innate physiological metabolic response to psychotropic drugs.

The content of all patents, patent applications, published articles, abstracts, books, reference manuals, sequence accession numbers, as cited herein are hereby incorporated by reference in their entireties to more fully describe the state of the art to which the invention pertains.

The invention claimed is:

1. A method of identifying markers in an individual correlated with the individual's likelihood developing increased body mass associated with the use of olanzapine, comprising:

assaying genetic material from the individual for the presence of at least one positive coefficient marker and at least one negative coefficient marker to produce a physiotype for the individual, wherein the positive coefficient marker is rs7412 corresponding to SEQ ID NO. 297 and the negative coefficient marker is rs5092 corresponding to SEQ ID NO. 22, wherein at least one positive coefficient marker and at least one negative coefficient marker are oppositely associated with the likelihood of developing increased body mass associated with the use of olanzapine in the individual, wherein the presence of a variant allele at position 22 of SEQ ID NO: 297 is associated with a likelihood of an increase in body mass associated with the use of olanzapine in the human individual and the presence of a variant allele at position 22 of SEQ ID NO: 22 is associated with a likelihood of a decrease in body mass associated with the use of olanzapine in the human individual, and wherein position 22 of SEQ ID NO: 22 and position 22 of SEQ ID NO: 297 each include one variant allele and one wild type allele.

2. A method of selecting risperidone or olanzapine as a psychotropic drug for administration to an individual, comprising:

assaying genetic material from the individual for the presence of at least one first positive coefficient marker and at least one first negative coefficient marker to produce a first physiotype for the individual, wherein the first positive coefficient marker is rs7412 corresponding to SEQ ID NO. 297 and the first negative coefficient marker is rs5092 corresponding to SEQ ID NO. 22, wherein the at least one first positive coefficient marker and the at least one first negative coefficient marker are oppositely associated with the likelihood of developing increased body mass associated with the use of olanzapine in the individual, and wherein the presence of a variant allele at position 22 of SEQ ID NO: 297 is associated with a likelihood of an increase in body mass associated with the use of olanzapine in the human individual and the presence of a variant allele at position 22 of SEQ ID NO: 22 is associated with a likelihood of a decrease in body mass associated with the use of olanzapine in the human individual, assaying genetic material from the individual for the presence of at least one second positive coefficient marker and at least one second negative coefficient marker to produce a second physiotype for the individual, wherein the second positive coefficient marker is rs6837793 corresponding to SEQ ID NO. 243 and the second negative coefficient marker is rs8179183 corresponding to SEQ ID NO. 131, wherein the at least one second positive coefficient marker and at least the one second negative coefficient marker are oppositely associated with the likelihood of developing increased body mass associated with the use of risperidone in the individual, and wherein the presence of a variant allele at position 22 of SEQ ID NO: 243 is associated with a likelihood of an increase in body mass associated with the use of risperidone in the human individual and the presence of a variant allele at position 22 of SEQ ID NO: 131 is associated with a likelihood of a decrease in body mass associated with the use of risperidone in the human individual, and comparing the first physiotype to the second physiotype and selecting risperidone or olanzapine as the psychotropic drug for administration to the individual.

3. The method of claim 2, wherein comparing the first physiotype to the second physiotype and selecting risperidone or olanzapine as the psychotropic drug for administration to the individual includes determining a predicted likelihood of developing increased body mass response for the individual given by the formula:

$$C + \sum_i c_i g_i$$

where C is an intercept from the first and second physiotype, $c_i$ are coefficients from the first and second physiotype and the $g_i$ are genotypes from the first and second physiotype, coded 0 for a wild type allele homozygote, 1 for a heterozygote, and 2 for variant allele homozygote.

* * * * *

SEQUENCE LISTING

<160> NUMBER OF SEQ ID NOS: 484

<210> SEQ ID NO 1
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: M=A or C
<220> FEATURE:
<221> NAME/KEY: misc_feature
<222> LOCATION: (22)..(22)
<223> OTHER INFORMATION: m = a or c

<400> SEQUENCE: 1
actgctctct agttggaaag amgaaaggat aaggttggag ga                42

<210> SEQ ID NO 2
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 2
caagagaatg gccactggtc amctaccgtg ccaacctgcc aa                42

<210> SEQ ID NO 3
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 3
ctttacaaca ggcataaatt awttcttcag agaagttcaa tt                42

<210> SEQ ID NO 4
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 4 tccctcctc aggtggacgg crtgctagaa aactggatct gg                 42

<210> SEQ ID NO 5
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 5
gcagatgtct ttgtaaaact crtctcttta ttctggaaat ta                42

```
<210> SEQ ID NO 6
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 6
agtttcatgt acattaaata traatttctt ttggctggaa at            42

<210> SEQ ID NO 7
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 7
ccttactcag agtctctctg crcccagtgt gctagccttg tg            42

<210> SEQ ID NO 8
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 8
cctaaatgcc aagtcggctt trttatcatt gtggttgctg ct            42

<210> SEQ ID NO 9
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 9
agctttcaaa tgtcatgcat trtgtggcag gagtaggttt ta            42

<210> SEQ ID NO 10
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 10
aagagtccat tcaaagggt trtacagaca gaaaaccagt gg            42

<210> SEQ ID NO 11
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g
```

```
<400> SEQUENCE: 11
tgctcagcct tcttcaatga crgtgttttg ctattgtctc ta                              42

<210> SEQ ID NO 12
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 12
ttgtttttca agttttgatt tmtctgctaa aattcagacc tg                              42

<210> SEQ ID NO 13
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 13
ctctccctcc tgtcctctcc crcaagtaga ctgagggcag ct                              42

<210> SEQ ID NO 14
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 14
agcgggcttc ctcttgaaca crgtcctcaa tgctcctctt cc                              42

<210> SEQ ID NO 15
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 15
gacagagaga ggacccaagc asgcaactag ttggaggact tg                              42

<210> SEQ ID NO 16
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 16
tttcaactcc ttcctgcagt crttccaggt ggggcctgtg ac                              42

<210> SEQ ID NO 17
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: m = a or c

<400> SEQUENCE: 17
ctcccctctc agttcagggc tmtcttgggt ccctgccagc tg                            42

<210> SEQ ID NO 18
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 18
ccctcatctg aaacaagaac trgaggcctg ggctgctcct cc                            42

<210> SEQ ID NO 19
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 19
ttcaaggtca agttctttgg tragaaggtc ctagctgcat tg                            42

<210> SEQ ID NO 20
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 20
taaaaaacta agcccgcct gmgtcttgtt aatgaatgat ag                             42

<210> SEQ ID NO 21
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 21
gcataaagga agaaaccatc aratggttca gaattggtaa ga                            42

<210> SEQ ID NO 22
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 22
cagtgctgac caggtggcca crgtgatgtg ggactacttc ag                            42

<210> SEQ ID NO 23
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 23
ccgtgctctt aaccatctgc craacttgca ctgccagtca tt              42

<210> SEQ ID NO 24
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 24
ttcacatact ggggagttca gmatagtaat gtttttggaa aa              42

<210> SEQ ID NO 25
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 25
agcaaactga ggcacagaga trttacatca cctgtacaag gg              42

<210> SEQ ID NO 26
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 26
ccagccagcg ctgggatgtg crggaggacg gggacagcat tc              42

<210> SEQ ID NO 27
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 27
tactggtgct gacgcctggc csgccggccg cgggactatc ca              42

<210> SEQ ID NO 28
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 28
```
acccaataag gtgagtggat grtacatgga gaaggaggga gg    42

<210> SEQ ID NO 29
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 29
tcctgtgaga gagttgagag crataatttt agggtggtta tt    42

<210> SEQ ID NO 30
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 30
aagctgctgt aaatggaggc trcctagaga ggagagggcc tg    42

<210> SEQ ID NO 31
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 31
ggagagagca gccccctcaaa crcagccccct gggcaaggag ac    42

<210> SEQ ID NO 32
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 32
ctagcacatc tcttgcccga grgcctcagc gcttgctgtc gc    42

<210> SEQ ID NO 33
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 33
aaactaggaa ttacatggta arttgaaaga ggaagttagg gg    42

<210> SEQ ID NO 34
<211> LENGTH: 42
<212> TYPE: DNA
<213> ORGANISM: Homo sapiens
<220> FEATURE:
<221> NAME/KEY: misc_feature
<222> LOCATION: (22)..(22)

<223> OTHER INFORMATION: r = a or g

<400> SEQUENCE: 34
aaagagctct tttgtctttc artatctctt ccctgtttgg ac                            42

<210> SEQ ID NO 35
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 35
tctcttgaag gtgggtgggc crctaccacc aagaatatct cc                            42

<210> SEQ ID NO 36
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 36
gccactgagg gagaaggcca crgacgtgat gccgcagatg at                            42

<210> SEQ ID NO 37
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 37
atcttttaga gtccgacctc trgaaatgtg tgtatgatgt ga                            42

<210> SEQ ID NO 38
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 38
cgaagcatat tacccatgaa crcatatatc cacatgtatg ac                            42

<210> SEQ ID NO 39
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 39
tgcaaagttc tgtgacaata crtactcggg ctagaggtga ct                            42

<210> SEQ ID NO 40
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 40
cggggctggc tctcattgct grccttcact gtgcactgtg ag                42

<210> SEQ ID NO 41
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 41
ggtgttgggc ttcagcagga crttgatgcc ccccacgatg gc                42

<210> SEQ ID NO 42
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 42
cactgtactt actgctaaag gracccaaac ggtccattcc ct                42

<210> SEQ ID NO 43
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 43
atctttctgc cacaccacct crccctcctt tctcaaggtc tt                42

<210> SEQ ID NO 44
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 44
aaactgagtc ccagaaggat twagtcagtt acccaagttg tt                42

<210> SEQ ID NO 45
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 45
cacggagact tatgcaccag artgaaatgc tgagatgttc tt                42
```

```
<210> SEQ ID NO 46
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 46
gtcaagggta taacacctta grgtataatt tgttacagtg tt                              42

<210> SEQ ID NO 47
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 47
tgcatgagtg tgtccgtgtc crtggggtg attgtgggta ag                               42

<210> SEQ ID NO 48
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 48
agaatttgta tctcacacca artaattttt aaaaaggtca tt                              42

<210> SEQ ID NO 49
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 49
atgatgtgtg tgggggagga araagcttat caaatcaaag cc                              42

<210> SEQ ID NO 50
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 50
agtttgagac gtgggtgaaa crtaggtgga aaagtccagc aa                              42

<210> SEQ ID NO 51
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t
```

<400> SEQUENCE: 51
gagaaagaga gccaggacaa gwctctctcc ctccctgagc tg                             42

<210> SEQ ID NO 52
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 52
ctctccagtg tggccaagat craagatgta cctggtgacc cc                             42

<210> SEQ ID NO 53
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 53
ctatcctcaa atgctatata amccaactgg tggaaaaaaa tt                             42

<210> SEQ ID NO 54
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 54
agtgaatgag atagcagaca amccagatgc ctaccgacag gt                             42

<210> SEQ ID NO 55
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 55
ttgctgcctc ccgccagcga argccccgag ccgctgtctc ag                             42

<210> SEQ ID NO 56
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 56
gtgtgtgcct ctttgatgga traagtggcc aatcacctag gc                             42

<210> SEQ ID NO 57
<211> LENGTH: 42
<212> TYPE: DNA
<213> ORGANISM: Homo sapiens
<220> FEATURE:

-continued

<221> NAME/KEY: misc_feature
<222> LOCATION: (22)..(22)
<223> OTHER INFORMATION: r = a or g

<400> SEQUENCE: 57
gcaggtctcc acacacctgc crtccaggta gaagttgcgg ca           42

<210> SEQ ID NO 58
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 58
tgaatggctg aattatgata trtacattcc tgatcttcct cg           42

<210> SEQ ID NO 59
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 59
aacaaagatt ctcctttcct crttcaccac tttcttgctg tt           42

<210> SEQ ID NO 60
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 60
atagtgtgga cattgaaaga tmccctgacc ttccctatgt tt           42

<210> SEQ ID NO 61
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 61
aaaagtgttt cccagaaacc crccatccct ttatccttt at            42

<210> SEQ ID NO 62
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 62
cagactctag agactgaaat tsaaggccca gttcttgctg tt           42

<210> SEQ ID NO 63

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 63
tacctacgtt tgcaacactt crtgtttata agccatcagc tg                              42

<210> SEQ ID NO 64
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 64
ttcagtttca tctaacgtca craagaacgc tgctttctcc ac                              42

<210> SEQ ID NO 65
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 65
ttagggactt tcaaaaactc asactcttgg gttctgaccc tg                              42

<210> SEQ ID NO 66
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 66
tgggagttgg ccatgcagct csgggccgac ggagcagaac gc                              42

<210> SEQ ID NO 67
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 67
gccttcttgc tggcacccaa trgaagccat gcgccggacc ac                              42

<210> SEQ ID NO 68
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 68
```

```
ttgccaggag ctgaggtctg crggaggaga gttgtgagtg aa                              42
```

<210> SEQ ID NO 69
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 69

```
ccagcagggc cttgtagctg artacaccag agatgaggct gg                              42
```

<210> SEQ ID NO 70
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 70

```
agtgggaagc agcaacatag artggctttt caagaaataa ac                              42
```

<210> SEQ ID NO 71
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 71

```
cagcactccg aatgaaggct grcagtgaaa ctgaattact ta                              42
```

<210> SEQ ID NO 72
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 72

```
atgccgggtg ctagagatac arcagtgaac atgacaaagt tc                              42
```

<210> SEQ ID NO 73
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 73

```
gagaactgag ggggtgggag grgaagagag tgccggcggc tc                              42
```

<210> SEQ ID NO 74
<211> LENGTH: 42
<212> TYPE: DNA
<213> ORGANISM: Homo sapiens
<220> FEATURE:
<221> NAME/KEY: misc_feature
<222> LOCATION: (22)..(22)

<223> OTHER INFORMATION: r = a or g

<400> SEQUENCE: 74
gattaaatgc attctgccac arttctcatt attttcatag tc                              42

<210> SEQ ID NO 75
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 75
cacccgccat caatcctgcc grctctggcc gctctgcctc at                              42

<210> SEQ ID NO 76
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 76
accagaagct agcataatgg artatcgccc ctcactttgt tc                              42

<210> SEQ ID NO 77
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 77
cgtcagaaat gtgtggtggg gmcatattag tggtgacagg tt                              42

<210> SEQ ID NO 78
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 78
ggctggttgg agcctctccc crggcagcag ccctggtgga ga                              42

<210> SEQ ID NO 79
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 79
ccttctctct tgggccaagg artttctgct ctattgcatg tt                              42

<210> SEQ ID NO 80
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 80
aacctcactt aacattttgg crtgggaatg gcaattatct gc                           42

<210> SEQ ID NO 81
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 81
gattttgccc agtggctctc craggtggct gtactgatgg ac                           42

<210> SEQ ID NO 82
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 82
gatgtggata ctgagcctcg crgcttatat gattgctcac ag                           42

<210> SEQ ID NO 83
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 83
ggtactgcac caggcggccg crcacgtcct ccatgtccgc gc                           42

<210> SEQ ID NO 84
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 84
tgggtccccc cgcacagagc crtcctgctg ccggtagccc gc                           42

<210> SEQ ID NO 85
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 85
ccggagtctc tcatgccgct crgggtccag gcccggggtg ga                           42
```

```
<210> SEQ ID NO 86
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 86
caaacccttt ccactccatt awaagaacat gaatcctgat aa                          42

<210> SEQ ID NO 87
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 87
ctgggagatt ctcctattga cscagaaagc gattccttca ct                          42

<210> SEQ ID NO 88
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 88
ttttgtccag aaaagtgaac cwggtcaatg gattatttat ga                          42

<210> SEQ ID NO 89
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 89
aggacccatc ctggatcatc cratgagcag ccgtggcgct cg                          42

<210> SEQ ID NO 90
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 90
ctccggacgg gcacagagag gmtttatagt ggttgagacc ca                          42

<210> SEQ ID NO 91
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g
```

```
<400> SEQUENCE: 91
tcttcttgcc ctacatactt craaagccct tggagaaatc ct                              42

<210> SEQ ID NO 92
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 92
cggatggtgg atttcgctgg crtgaaggac aaggtgtgca tg                              42

<210> SEQ ID NO 93
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 93
gtcagcacct ggaagccccc artgaaggaa ccatggactg tg                              42

<210> SEQ ID NO 94
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 94
gttccagggt atatctcaga gmctggagaa cgtgtctggt ta                              42

<210> SEQ ID NO 95
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 95
gattttgtca aagatagatt crggagccat ccatttcaga gg                              42

<210> SEQ ID NO 96
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 96
aggaccctgg accccgaag gmaaggccgg cttcctctgg gt                               42

<210> SEQ ID NO 97
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: r = a or g

<400> SEQUENCE: 97
agcctcgtta tcccatgtgt craagaagat aggttctgaa at                              42

<210> SEQ ID NO 98
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 98
aaagaatctt gtccccaaca grttctgggt ataaccaacc ct                              42

<210> SEQ ID NO 99
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 99
acagccatag agacaagggc argagagagg cgatttaata ga                              42

<210> SEQ ID NO 100
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 100
acgctgggct gcacgctacc crccaggtcc cctgccactg cc                              42

<210> SEQ ID NO 101
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 101
tgtgtaactc gaccctgcac crgctcactc tgttcagcag tg                              42

<210> SEQ ID NO 102
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 102
gttagagact gaaagctttc aratgaacag aattgatact gg                              42

<210> SEQ ID NO 103
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 103
ggcaggtaat gatattgtga crtggagaat gtgcacttag aa                              42

<210> SEQ ID NO 104
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 104
ggctccacga caatgagtac arctgtggtc cgtggcttct tg                              42

<210> SEQ ID NO 105
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 105
aaggggactg tgagaaaaaa artgttcatg aggctcgagt cc                              42

<210> SEQ ID NO 106
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 106
cagttcagtt ggttttagta trttcagagt tgtgcatcca tc                              42

<210> SEQ ID NO 107
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 107
gttggctcta ctcatttcct crtcgtcatt ctcttgtagt ca                              42

<210> SEQ ID NO 108
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 108
```
agaatggtgg tgtcttcttc arttgatgga gaagcgcagc cg                             42

<210> SEQ ID NO 109
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 109
aattagattg gaatggatgt awccgtgtat attcataccc tt                             42

<210> SEQ ID NO 110
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 110
attttcttga cccctactta cratcctggg agatgtattt gg                             42

<210> SEQ ID NO 111
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 111
cttggtggcg tgcttcatgt arccctgcat gaagctgaga ag                             42

<210> SEQ ID NO 112
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 112
cgccccttta cctttccatg grttagatga aggagcgtag gt                             42

<210> SEQ ID NO 113
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 113
gctcttagaa ctagctacaa aratatttca tatgtttatg tc                             42

<210> SEQ ID NO 114
<211> LENGTH: 42
<212> TYPE: DNA
<213> ORGANISM: Homo sapiens
<220> FEATURE:
<221> NAME/KEY: misc_feature
<222> LOCATION: (22)..(22)

```
<223> OTHER INFORMATION: w = a or t

<400> SEQUENCE: 114
acttgtaatt atgcgtggag twgttaactg tattttttac ac                              42

<210> SEQ ID NO 115
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 115
tgctcaccct aggatggagg grgcagtggg ggctggttag ga                              42

<210> SEQ ID NO 116
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 116
gcctgtacca atacatcctg cmgtggccac ggtgaatgtg ta                              42

<210> SEQ ID NO 117
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 117
gcaagcccta ttagacatat amttttccca actttttccct tt                             42

<210> SEQ ID NO 118
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 118
gggtaggaaa ttaagtgaat amttttttgtg atccaagaaa ga                             42

<210> SEQ ID NO 119
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 119
cttttaagca acctacaggg gmagccctgg agattgcagg ac                              42

<210> SEQ ID NO 120
<211> LENGTH: 42
<212> TYPE: DNA
```

```
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 120
gaaatgagca agagatctga cwccaggagt ctttcctcat tt                    42

<210> SEQ ID NO 121
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 121
gcttccttat gtaaaatgta grtatttcta aagtaacgca at                    42

<210> SEQ ID NO 122
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 122
ctactggaag attagccacg trttgagttt tgtctttgca tt                    42

<210> SEQ ID NO 123
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g
<220> FEATURE:
<221> NAME/KEY: misc_feature
<222> LOCATION: (37)..(37)
<223> OTHER INFORMATION: n = a or c or t or g

<400> SEQUENCE: 123
actctgcacc ttcaggttca grcccttcaa gatctancag ga                    42

<210> SEQ ID NO 124
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 124
ttttccaaag atgatctctc crgagctatt gtttcttcat tc                    42

<210> SEQ ID NO 125
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t
```

```
<400> SEQUENCE: 125
agattcctcc ctgtacgata gwgtcttact tttccacttt gc                              42

<210> SEQ ID NO 126
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 126
ccttctctat gctgcaacag crgatgattc ttcctcttcc ac                              42

<210> SEQ ID NO 127
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 127
cctagagaca tatctcagtt argttttagc ctcaccagta tt                              42

<210> SEQ ID NO 128
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 128
cagctgaaag aaagacaaat artagatacc cactgcatgg ct                              42

<210> SEQ ID NO 129
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 129
ttcttgagtc cgtctgtctg grtgggaacc cagtctttac ca                              42

<210> SEQ ID NO 130
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 130
accctgcatt ctgaggggtc trgagggaaa ctgacagctg tg                              42

<210> SEQ ID NO 131
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: s = c or g

<400> SEQUENCE: 131
taatggagat actatgaaaa asgagaaaaa tgtcacttta ct                              42

<210> SEQ ID NO 132
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 132
tagtttgact caccttccca gmaccttcta gttctttctt at                              42

<210> SEQ ID NO 133
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 133
cagagcacga ggctgatttt cmatcccagt gtgggccaca cc                              42

<210> SEQ ID NO 134
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 134
attaacccat ggtccagaaa tsatgggttg ttaaatgacc aa                              42

<210> SEQ ID NO 135
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 135
tacgattctc accccatatt twcaagccta gtccaaggat ta                              42

<210> SEQ ID NO 136
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 136
ggctgctcag ggcctcgtcc amccccagcc tgacagagag ct                              42

<210> SEQ ID NO 137
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 137 ggcgcccct ggacttctgc trgaatttag atttaaatag at                    42

<210> SEQ ID NO 138
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 138
agtgcccgat atacattaag trcttaataa atgactgcta cc                   42

<210> SEQ ID NO 139
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 139
ctgaccccaa gagcgagggg arcccaactc tgtgctctca cc                   42

<210> SEQ ID NO 140
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 140
gaccctgtaa ttttcagaaa crcacatagg agtgggtgtc tg                   42

<210> SEQ ID NO 141
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 141
tacctggacg ctggctgccc cmcggtcaga ggtctggggt cc                   42

<210> SEQ ID NO 142
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 142
```
caggctcagg gtctaaattc crtatccttt cttccatacc ct                             42

<210> SEQ ID NO 143
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 143
tgctccaaag tctatcacaa tratcctctt ttcataaag cc                              42

<210> SEQ ID NO 144
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 144
tttagacata tgcctctata tscttctata attattaata gt                             42

<210> SEQ ID NO 145
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 145
ctcagttcct ctgctgtctc crtccttgcc ccatcctcca gg                             42

<210> SEQ ID NO 146
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 146
tttcctaatt ttgcagttga grtttaagag gttgggaact gg                             42

<210> SEQ ID NO 147
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 147
atggggccct ggggagagag crtggcaagt tctcagcatt cg                             42

<210> SEQ ID NO 148
<211> LENGTH: 42
<212> TYPE: DNA
<213> ORGANISM: Homo sapiens
<220> FEATURE:
<221> NAME/KEY: misc_feature
<222> LOCATION: (22)..(22)

<223> OTHER INFORMATION: r = a or g

<400> SEQUENCE: 148
cgggaagctt gcaagacgct crgcttccta ttgcaagacc gc            42

<210> SEQ ID NO 149
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 149
gcttgtcgat tgcttatcca gwgcctacag ctccaggaag cc            42

<210> SEQ ID NO 150
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 150
cacacactaa catgcagaaa crtactacct cacactcaaa tg            42

<210> SEQ ID NO 151
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 151
acaatctggg ctatgagatc artaaagtca gagccaaaag aa            42

<210> SEQ ID NO 152
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 152
ttcagcagga gctgggccct crggcccagt ggctgggctg ga            42

<210> SEQ ID NO 153
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 153
gatatcgtga ctaccgtcca gscctcctat tctaagaaaa gc            42

<210> SEQ ID NO 154
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 154
tagcttatca ggtttattgc tstccatctg tatcacctgc ct                        42

<210> SEQ ID NO 155
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 155
cctgttttat gagattttaa cmccttacct tgattcctag ga                        42

<210> SEQ ID NO 156
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 156
agccccagtc cttaccggaa crgtagaggc ttaacaaaca tt                        42

<210> SEQ ID NO 157
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 157
caagagctcc ctacccagga arcccaagcc tcacccagaa tg                        42

<210> SEQ ID NO 158
<211> LENGTH: 42
<212> TYPE: DNA
<213> ORGANISM: Homo sapiens

<400> SEQUENCE: 158
cccttgggaa cgcggcccga arcccaggat ctgggtgatg gg                        42

<210> SEQ ID NO 159
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 159 cctttttaatg gccatcaata amacagcctg actagttcaa ca                       42

<210> SEQ ID NO 160
<211> LENGTH: 42
<212> TYPE: DNA
```

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 160
aaactgacct ccaacatgga tratggggac cgacttgtgg gg                              42

<210> SEQ ID NO 161
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 161
aaataaaaag aatgcagccc artgtggggt aagtaaaagg at                              42

<210> SEQ ID NO 162
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 162
gagaagctcc catctagctg trtatgatag ggggtttatc tg                              42

<210> SEQ ID NO 163
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 163
ggttagggag actagcaatt arttgagaag atgtagtttg ac                              42

<210> SEQ ID NO 164
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 164
tgcctgattt tgtcactgaa cratgagcat gatttttcca gg                              42

<210> SEQ ID NO 165
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 165
ctcataaaga gccagacaaa argaaaaaaa acccagaaat ta                              42
```

```
<210> SEQ ID NO 166
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 166
ggaatctcac aggccttcac cmctctcccc tgcccttctt ca          42

<210> SEQ ID NO 167
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 167
tgggacaggt gcgctcccag amgggatcct gtcgccagtt ct          42

<210> SEQ ID NO 168
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 168
gggtgtgccc tctagattta gscagagatc tatccagtgt at          42

<210> SEQ ID NO 169
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 169
tagtaaacta tttcttccca trggagaaga tggattcttt tc          42

<210> SEQ ID NO 170
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 170
gccccacatc tgtgccacag asacagaccc tgggatcctc ag          42

<210> SEQ ID NO 171
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g
```

```
<400> SEQUENCE: 171
cttgttcatg atgagattat asctgatctg acgtgagaat gc                              42

<210> SEQ ID NO 172
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 172
ggtgcctctg tacaaccatg tstctcttct ctgctgtctg ct                              42

<210> SEQ ID NO 173
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 173
agcaacgtct tgctgttttt crgaggtaga gggctgcttt ct                              42

<210> SEQ ID NO 174
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 174
gccccaccca ctctcctgac twtcgggagc aaaccagtag ag                              42

<210> SEQ ID NO 175
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 175
aatgaccggt tatactcttc trtaaaggaa tcctggaggt gt                              42

<210> SEQ ID NO 176
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 176
tagccatact ccagaaaaaa tmaataaatt cccttggccc ca                              42

<210> SEQ ID NO 177
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: r = a or g

<400> SEQUENCE: 177
ttcaacaagc ctgcttactg crgttagttg tgaccattgt ct                              42

<210> SEQ ID NO 178
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 178
atgatctcag aggctgtata cmcacccaga gttattttat gc                              42

<210> SEQ ID NO 179
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 179
cacaacaagg gtttagctct arggagagca gaggcaggat ga                              42

<210> SEQ ID NO 180
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 180
attgagtggc tggggcctgg crcagccaga aatgacagtg gc                              42

<210> SEQ ID NO 181
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 181
gccaatgcag atttatcctc crcccttctc caacctgttc ta                              42

<210> SEQ ID NO 182
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 182
tgctcactat atgccaatag crtcccacaa ccactgattg tg                              42

<210> SEQ ID NO 183
```

-continued

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m= a or c

<400> SEQUENCE: 183
cagaaagatg tcatcatcca gmattgcgtc cacacagtca ac                    42

<210> SEQ ID NO 184
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 184
gagcgagagg acgctattgc artgccacgt gaagtgaatt gt                    42

<210> SEQ ID NO 185
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 185
gcacctcctg tgaccagccc awgttgttgg gcatagagac cc                    42

<210> SEQ ID NO 186
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 186
ctggttggga gccttcccga crtgaacaag atgctggata ag                    42

<210> SEQ ID NO 187
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 187
cgaacaagga cgctttgaag argtggaatt actgtgcaag ga                    42

<210> SEQ ID NO 188
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 188
```

```
cttcccagtt gcactaacag arcctttgat tcagttcagc aa                    42
```

<210> SEQ ID NO 189
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 189

```
ctctctcgtt tgggaaaaat arcggaagaa ctagtgtatc ct                    42
```

<210> SEQ ID NO 190
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 190

```
ggagggaaat taaaatgaag artcaatgag attgcacatg aa                    42
```

<210> SEQ ID NO 191
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 191

```
ggattgcaat aaagggaagg awgaaggatg attttggctt ga                    42
```

<210> SEQ ID NO 192
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 192

```
taccacgtac ctgctcatgg gmcactgggc tctgggcacg ct                    42
```

<210> SEQ ID NO 193
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 193

```
atgtgaataa taaggataat artcaccaaa tacatagaca tg                    42
```

<210> SEQ ID NO 194
<211> LENGTH: 42
<212> TYPE: DNA
<213> ORGANISM: Homo sapiens
<220> FEATURE:
<221> NAME/KEY: misc_feature
<222> LOCATION: (22)..(22)

<223> OTHER INFORMATION: m = a or c

<400> SEQUENCE: 194 tctgccccttt tgggctgcag cmtcacaagc tgtgtggcgt tg                          42

<210> SEQ ID NO 195
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 195
cccattcaga tgcactggta cmgggccacc caccaggaag cc                           42

<210> SEQ ID NO 196
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 196
ctgcaggtgc acggtttcct gmttgcccag gtgtctctga gc                           42

<210> SEQ ID NO 197
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 197
gaggacacct cgcccagtaa tmcagacacc ctcctccatt ct                           42

<210> SEQ ID NO 198
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 198
tctggttgaa taaggttct traaacctc ctgagtcagg ac                             42

<210> SEQ ID NO 199
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 199
tctgggaaat gcaaggcaca crgccaagtg tggtgggggt ag                           42

<210> SEQ ID NO 200
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 200
agtggtcagg cttcacccag trctacagag cagatctggg ac                42

<210> SEQ ID NO 201
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 201
cggcaattag actggctaga gmcacctcag tcaggctctc cc                42

<210> SEQ ID NO 202
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 202
cctgaggatg aagggcgtc crtggccagg cagcagtgag aa                 42

<210> SEQ ID NO 203
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 203
ggaaggaacc tcgtacatcc trcggggcag tggggacagc gt                42

<210> SEQ ID NO 204
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 204
attctctttc tccctttctt craaacaggc cctgaagtat ga                42

<210> SEQ ID NO 205
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 205
ttcttgaaga ccaaagtaga artccttaga ataactcatt ct                42
```

```
<210> SEQ ID NO 206
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 206
ggtgggggct gaccgcaagc crcgccttct gtgcacctgg tc                              42

<210> SEQ ID NO 207
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 207
ccagcaaaca ccaggctacc amggatccca aagatgccaa aa                              42

<210> SEQ ID NO 208
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 208
tggcttcagc ttgtaaagct trgaaacatt ctgaaacaac at                              42

<210> SEQ ID NO 209
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 209
gcctgtggtc acagagctcc tragtggcag aactcaactt ga                              42

<210> SEQ ID NO 210
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 210
ccatactgaa aatgctagtc crccaagcac actttgagat ca                              42

<210> SEQ ID NO 211
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c
```

```
<400> SEQUENCE: 211
tgaaatcctt ttccctgctt tmctccagca cttgggggat gt                               42

<210> SEQ ID NO 212
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 212
aattatatct tattattaaa astctaccaa ctcaaagctt cc                               42

<210> SEQ ID NO 213
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 213
caaagggtga gctctgtggg cmcaggacgc atggtagatg ga                               42

<210> SEQ ID NO 214
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 214
ctcattggcg caagagcagc crccagttat ggctcactcc ct                               42

<210> SEQ ID NO 215
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 215
agctaccttg gccagcgagt graagactcg ctcagagaac ca                               42

<210> SEQ ID NO 216
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 216
tctagaaggc atccaggcct crcctctttc atgtgcagct tt                               42

<210> SEQ ID NO 217
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: r = a or g

<400> SEQUENCE: 217
caacttcttt gtcatctcct trgctgtgtc agatctcttg gt                              42

<210> SEQ ID NO 218
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 218
acatgtgtac acgtggtgta trttaaaaac ttcaggctct ct                              42

<210> SEQ ID NO 219
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 219
tgcagaaaac ccttcacccc crtgtcaaaa ggagctgacg aa                              42

<210> SEQ ID NO 220
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 220
ggagagggaa aaataaagtt awtgcatgtc ccagtttcct ca                              42

<210> SEQ ID NO 221
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 221
tttccttcca atatattcta crtaagttcc cggaaagtcc cc                              42

<210> SEQ ID NO 222
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 222
ttctactccc tcttcccctt awtgaaggat gctgtgtgta ca                              42

<210> SEQ ID NO 223
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 223
gcaacccgga catggacact cscacagtgg tgaggaagag ac          42

<210> SEQ ID NO 224
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 224
acagctcctg ttgccatagg arggagctgg gtgagatact ag          42

<210> SEQ ID NO 225
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 225 aaaaacttt tctgatccct tmcttttgaa aagcccatta at           42

<210> SEQ ID NO 226
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 226
tgcgcgcgca gcagagcagt csctggaagg ccttgcggaa gt          42

<210> SEQ ID NO 227
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 227
cttttcacag gaaaatttct trggagtcta ttgtcactgt ct          42

<210> SEQ ID NO 228
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 228
```

```
cgcatcggcc tctatgactc crtcaagcag gtgtacaccc cc                              42
```

<210> SEQ ID NO 229
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 229

```
acaccgcggt actgggcgct grctgtagcg cgcactggcc cc                              42
```

<210> SEQ ID NO 230
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 230

```
tgcaatgaaa tgctctgtcg grttggggtt gtctaattgc ct                              42
```

<210> SEQ ID NO 231
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 231

```
tcatcaatcc atgaaactta gmataatact gataaattga at                              42
```

<210> SEQ ID NO 232
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 232

```
cattgcgtat tatcaggaaa araatactgt ctattaaaga aa                              42
```

<210> SEQ ID NO 233
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 233

```
ctcatcarct tctacatccc crttgccatc atgatcgtga cc                              42
```

<210> SEQ ID NO 234
<211> LENGTH: 42
<212> TYPE: DNA
<213> ORGANISM: Homo sapiens
<220> FEATURE:
<221> NAME/KEY: misc_feature
<222> LOCATION: (22)..(22)

<223> OTHER INFORMATION: r = a or g

<400> SEQUENCE: 234
atgcgggtgg ggaggtgaga grttggcgac attgacggga gg                         42

<210> SEQ ID NO 235
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 235
taaagtttga cttttcctat tsgtagctca cttgaagaca aa                         42

<210> SEQ ID NO 236
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 236
gaccagggct tctgaactgc araggtgctt tttcctaaaa cc                         42

<210> SEQ ID NO 237
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 237
aagggcattt gcattcaaag grttctaaac ggaaaatgac aa                         42

<210> SEQ ID NO 238
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 238
agacttcccc aggaaagtcc tmtgtgtctt gtatttggtt ac                         42

<210> SEQ ID NO 239
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 239
atgttcatga gagcaaacct crtgccaatg cagtttctgg gt                         42

<210> SEQ ID NO 240
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 240
agtgaggctt ggaaaggcgt crtggacaga cctgggtcgc tt                    42

<210> SEQ ID NO 241
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 241
cttcaaaaag tgaaactaac tmctcgtttc tggtaaagag cc                    42

<210> SEQ ID NO 242
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 242
ccagtttaaa aatacatcat argtaaggca atgagaagag tt                    42

<210> SEQ ID NO 243
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 243
atgaattgtc actcagaaga arcttaatag gcattaatac ta                    42

<210> SEQ ID NO 244
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 244
tgctttgagc aagggtaccc crctctgaga attcccagcc at                    42

<210> SEQ ID NO 245
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 245
ttctgcttaa atatggcttg tscattataa cataagttag gc                    42
```

```
<210> SEQ ID NO 246
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 246
tttccctcta ctcagttatc crattattca tgactagatg ag                             42

<210> SEQ ID NO 247
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 247
ccatagatcc aaacatcttt awctatccat gtatttgagt ag                             42

<210> SEQ ID NO 248
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 248
tcaagggcct tgctgggggc aracaaggtg gaacataaca cg                             42

<210> SEQ ID NO 249
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 249
ttgtcccagt tgccaagtga grggtgtgat ctcatttcct ag                             42

<210> SEQ ID NO 250
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 250
attttcttct gggtggccct aractgcttt cttttccccc at                             42

<210> SEQ ID NO 251
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g
```

```
<400> SEQUENCE: 251
ctcaggaggc cttactgtgc crtggttctt gcccttttgat tt                              42

<210> SEQ ID NO 252
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 252
aaccaattct ggcctttaaa gmagtctctt tatctcattc cc                               42

<210> SEQ ID NO 253
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 253
gccttcccct tagagaagag crcctgccag acaagggaga ag                               42

<210> SEQ ID NO 254
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 254
ttctgcagag cttcttctcc trtctcccac atgactaatg tt                               42

<210> SEQ ID NO 255
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 255
atagggagtc atggagggtt tstgagcagg ccagggatta ga                               42

<210> SEQ ID NO 256
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 256
cagaaggaag agttctgggg gmtcatctgg ggcctgcagc ag                               42

<210> SEQ ID NO 257
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: r = a or g

<400> SEQUENCE: 257
caggattgta agcacccect gratccaggt aaggccaagt tt                              42

<210> SEQ ID NO 258
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 258
accaaatatc tagggatcag araaattgat tcaggaaata ct                              42

<210> SEQ ID NO 259
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 259
tctaagtcat agctcttgat trtggcccac ccccagtagg ga                              42

<210> SEQ ID NO 260
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 260
ttatgtcacc ctggggagta aragaatggt cttcctgctc ct                              42

<210> SEQ ID NO 261
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 261
atctgccggt gattcaacag crtgcggaac ctgcatgacg tt                              42

<210> SEQ ID NO 262
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 262
gtagtgtagc accagggtcc crtggtgctg ctgtcggggt tg                              42

<210> SEQ ID NO 263
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 263
cctccggggc gtcttatggc cmccatgccg ctccagcgcg gc                          42

<210> SEQ ID NO 264
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 264
gacacagcac acaaccaccc grcctgttcc cgacacctcc cg                          42

<210> SEQ ID NO 265
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 265
taggaatggg caaatgaagt grccttctgc cccagcctct ct                          42

<210> SEQ ID NO 266
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 266
gctcaaagac cacgggcggg tsccaggggt cgttctggtg gt                          42

<210> SEQ ID NO 267
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 267
catagctttg ttagctatgc crgtaattaa caggcataac tc                          42

<210> SEQ ID NO 268
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 268
```

```
agccaggagc tttcctgggc gmttttgta caggatctca tt                             42
```

```
<210> SEQ ID NO 269
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 269
tgatttcttg catactttat tragcaaaat ccatgagaag tg                            42
```

```
<210> SEQ ID NO 270
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 270
tgagatctag tagaaggaca crtcttgaat tgggtcatgc tt                            42
```

```
<210> SEQ ID NO 271
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 271
tggggacaga ggctaaatac trcccctcc ccttttctac tt                             42
```

```
<210> SEQ ID NO 272
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 272
tttgcaagca ctttctcttc trcacgtttg gaacctaccc cg                            42
```

```
<210> SEQ ID NO 273
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 273
ttataaactg acacacacac amaaaaaatc cacacacact tt                            42
```

```
<210> SEQ ID NO 274
<211> LENGTH: 42
<212> TYPE: DNA
<213> ORGANISM: Homo sapiens
<220> FEATURE:
<221> NAME/KEY: misc_feature
<222> LOCATION: (22)..(22)
```

<223> OTHER INFORMATION: r = a or g

<400> SEQUENCE: 274
aggagctcgg agcaagaagg crcccaccga gagcgtctga ag                42

<210> SEQ ID NO 275
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 275
taataaatat taagggtgac crgtgactca ggctctgcct ct                42

<210> SEQ ID NO 276
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 276
ctgcagaagc aaggccaata artctctcaa aatgcagttc aa                42

<210> SEQ ID NO 277
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 277
agtcaacata tatttgagag amcttcaact tatcaagtat tg                42

<210> SEQ ID NO 278
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 278
ggtgaagagg ctgatggggc cmagcaggtc acagagctca tc                42

<210> SEQ ID NO 279
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 279
agaagctctt tcatgttgtc arttttagaa atccaaatca tt                42

<210> SEQ ID NO 280
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 280
cacgttgacg atgttgagca crtagaaggg catccagcag ag                    42

<210> SEQ ID NO 281
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 281
tgtgtgacat cccgacagaa asgcacttgt gaaatcgaca at                    42

<210> SEQ ID NO 282
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 282
agacacaggt gacccaactc cmatggctgg cctaggcccc tc                    42

<210> SEQ ID NO 283
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 283
ctccctagag ttacacacgc tmtctctccc gccaattgcc gg                    42

<210> SEQ ID NO 284
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 284
tttggatttt tccagccagg grttttttgtg tcctgttgct tt                   42

<210> SEQ ID NO 285
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 285
agtgttttcc aaggtgtgat traaaatgga gatttcttac ct                    42
```

```
<210> SEQ ID NO 286
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 286
ttccgctctc cctctgagag trtattactg tgcttcaata ca                              42

<210> SEQ ID NO 287
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 287
cattaggcac tgttttgttc craggaagat attgcaggag aa                              42

<210> SEQ ID NO 288
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 288
aatttcaact tataaacata crttgctata aatatgttca at                              42

<210> SEQ ID NO 289
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 289
agggactgga gcctgctgcc crgcacggtg gtcacaccct gg                              42

<210> SEQ ID NO 290
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 290
ggggatggag aaggcaggat gsggcaggag gccttggggg ga                              42

<210> SEQ ID NO 291
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g
```

```
<400> SEQUENCE: 291
cctgtaggat tgtgttcctc traaactgtc ccctaaatta tg                              42

<210> SEQ ID NO 292
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 292
tcaggtatta gcacttgaaa tmtaacttct ttatgaagct cc                              42

<210> SEQ ID NO 293
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 293
acagccttta cctaaggcag trctcttgct gacattcagg ac                              42

<210> SEQ ID NO 294
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 294
cccaaagctg agaagtggga crccccagca caccctcccc ca                              42

<210> SEQ ID NO 295
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 295
aactgaaagc agtttaatct crccagagcc actgaaggag tt                              42

<210> SEQ ID NO 296
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 296
catcaggatt atcagcattt argccagagt tgcaaattaa gt                              42

<210> SEQ ID NO 297
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: r = a or g

<400> SEQUENCE: 297
cggcctggta cactgccagg crcttctgca ggtcatcggc at                              42

<210> SEQ ID NO 298
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 298
agactgggcc ctgcacctcc crgggctgct agcatttgca gg                              42

<210> SEQ ID NO 299
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 299
ggacactggt tccacctccg crtggctgta cagtgctgcc ga                              42

<210> SEQ ID NO 300
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 300
agcaccttaa ctatagatgg trtaacccgg agtgaccaag ga                              42

<210> SEQ ID NO 301
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 301
cagcacctag caaaataccc crtggtatga tgttcaaagt aa                              42

<210> SEQ ID NO 302
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 302
tcagatggaa aaatgaagtc crgattcatt ctgggtcttt cc                              42

<210> SEQ ID NO 303
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 303
acaaatgctc tgagtcacca crctgcggct cagatgctat ga                              42

<210> SEQ ID NO 304
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 304
cacacagcat caaggactcc artaagatgg tcccagcctc tt                              42

<210> SEQ ID NO 305
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 305
cactatcatt gattatttcc crggaaccca taacaaatta ct                              42

<210> SEQ ID NO 306
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 306
cacaaaggca acagaccgtg araatagatg ccaatgtgct ag                              42

<210> SEQ ID NO 307
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 307
cagttagaat tgtcaatcta grtggggaca actcattatt tt                              42

<210> SEQ ID NO 308
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 308
```
cttcttcagc tacagcctgg gmgccatctg cccgaagcac tg					42

<210> SEQ ID NO 309
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 309
ttggctgaca ctttcgaaca crtgatagaa gagctgttgg at					42

<210> SEQ ID NO 310
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 310
atcgacttca ttgtaaagaa arctggacag aagcagctac ac					42

<210> SEQ ID NO 311
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 311
ggcaaagttt catctattag crataaaatg tgaattttct gc					42

<210> SEQ ID NO 312
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 312
acttatttca gtggttcaaa amatttcttc aacgcttaac ca					42

<210> SEQ ID NO 313
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 313
acccgcatct cccaccccca gracgcccct ttcgccccaa cg					42

<210> SEQ ID NO 314
<211> LENGTH: 42
<212> TYPE: DNA
<213> ORGANISM: Homo sapiens
<220> FEATURE:
<221> NAME/KEY: misc_feature
<222> LOCATION: (22)..(22)

```
<223> OTHER INFORMATION: r = a or g

<400> SEQUENCE: 314
atcgaagtta cgcatccggt tragttccag ctggaaggcc ag                            42

<210> SEQ ID NO 315
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 315
aaagtagaac ataccaggcc grgagaacaa catgtgctgc tt                            42

<210> SEQ ID NO 316
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 316
aaatctctct tcttcgataa asttcccagg aggtaaccca at                            42

<210> SEQ ID NO 317
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 317
aacaaatgta tctcatgtgt graccctgaa gacaaatgta ag                            42

<210> SEQ ID NO 318
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 318
aatcaaccaa gtggaagaaa gratatcaga gtctgaagac aa                            42

<210> SEQ ID NO 319
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 319
atcactcctc ttctagcatc trttacattt tctggcattt ct                            42

<210> SEQ ID NO 320
<211> LENGTH: 42
<212> TYPE: DNA
```

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 320
aacctgcgca tagtggtggc tracctgttc tctgccggga tg                              42

<210> SEQ ID NO 321
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 321
agggggcaac aggacacctg arggatggaa gggtcaggag gc                              42

<210> SEQ ID NO 322
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 322
ggtggggtta gagggatgg trcctggcag tgtgcagcag ac                               42

<210> SEQ ID NO 323
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 323
gcgtctttac agatccaaag craattttta aatctccagg ct                              42

<210> SEQ ID NO 324
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 324
gtctttctcc agatgatgcc artttgtgg atgccattca ta                               42

<210> SEQ ID NO 325
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 325
gccctggttt cctccagtat gmctgcaaaa tttcctctcc at                              42
```

```
<210> SEQ ID NO 326
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 326
ccaatgtact ttcctgaatg crgccagaaa ctgagcccac cc                             42

<210> SEQ ID NO 327
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 327
gctgttgctg ctctggcctc trtgagcccc gggagtccgc ag                             42

<210> SEQ ID NO 328
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 328
atttgcaaag tatgtacagc arcccccct tatcctcagt gg                              42

<210> SEQ ID NO 329
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 329
ccctccttca atattgacct arcgggggag aaaagattta ga                             42

<210> SEQ ID NO 330
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 330
tttacgttct cgaggttcga trtcttggct acaagctcta aa                             42

<210> SEQ ID NO 331
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c
```

```
<400> SEQUENCE: 331
gatgcaccta ctagacacct amtctgcgct agatggtggg gg                              42

<210> SEQ ID NO 332
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 332
gtcagtgact ggagagctcc awggaaagtc tctcagtgac ct                              42

<210> SEQ ID NO 333
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 333
tggtctggag tctcggagtc crggcgatgg ccacgatgac ca                              42

<210> SEQ ID NO 334
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 334
aaaaggcctc tggggcaggg argaatgtcc tttaatgggg ac                              42

<210> SEQ ID NO 335
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 335
catgctggag gagacaacag awcccaagtc tggcttccat at                              42

<210> SEQ ID NO 336
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 336
gccaaggatg gctctactgc crtccacttt gagcactctt gg                              42

<210> SEQ ID NO 337
<211> LENGTH: 42
<212> TYPE: DNA
<213> ORGANISM: Homo sapiens
<220> FEATURE:
```

```
<221> NAME/KEY: misc_feature
<222> LOCATION: (22)..(22)
<223> OTHER INFORMATION: r = a or g

<400> SEQUENCE: 337
tgtggtatct ttactggaac crataaatgc acctctggct ct                              42

<210> SEQ ID NO 338
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 338
caaaaattgg aattttgcca grtttaaatt ccagtggcct tc                              42

<210> SEQ ID NO 339
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 339
cagtttaaag tccagggtgt trttattacg tgtgcgcaaa ac                              42

<210> SEQ ID NO 340
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 340
gtggacgtgc agactgcatc cmtgcttgca ttcccaggga tg                              42

<210> SEQ ID NO 341
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 341
ccctttcagc aacaacacca tsggtagaaa tatgatgcag cg                              42

<210> SEQ ID NO 342
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 342
cccagcctgc aatcacagct trttactctg ggtgtgggtg gg                              42

<210> SEQ ID NO 343
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 343
attttccttt tttattcttt cmttttccct cctttctga at            42

<210> SEQ ID NO 344
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 344
ctggtaggaa attgaactga artcataaac ggaaagcagc ta            42

<210> SEQ ID NO 345
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 345
ttctaagtcc tctgccatgc crggaaagcc tgggtgcacc ca            42

<210> SEQ ID NO 346
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 346
ccagggatca gtgaggtctc tragacccctt ggggagcttg cc            42

<210> SEQ ID NO 347
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 347
acgacgccgt gccgggaata grgaagcagt gtgaggacca ca            42

<210> SEQ ID NO 348
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 348
```

```
actcaagttg agttgatcca trtaattcaa atccctcctc ac          42
```

<210> SEQ ID NO 349
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 349

```
gaacttttat aggttgctgg arggaatgta aattagtgca aa          42
```

<210> SEQ ID NO 350
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 350

```
atcaactgag gaagataata arctataaaa agatgaaaag ga          42
```

<210> SEQ ID NO 351
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 351

```
gccacgggga tttagggaga argcccccg atggttggct cc           42
```

<210> SEQ ID NO 352
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 352

```
ctctatgatt tcacagtgat grgctcaagt atgtgtctgc tt          42
```

<210> SEQ ID NO 353
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 353

```
gctgtgaaca cgcccaccac crtggacagc agcagctggg cc          42
```

<210> SEQ ID NO 354
<211> LENGTH: 42
<212> TYPE: DNA
<213> ORGANISM: Homo sapiens
<220> FEATURE:
<221> NAME/KEY: misc_feature
<222> LOCATION: (22)..(22)

```
<223> OTHER INFORMATION: r = a or g

<400> SEQUENCE: 354
aggttcatct tgacgcatcc tragctactt aacttcggtt cc                              42

<210> SEQ ID NO 355
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 355
aatgtggctg aagccaaaag cmtaatgaat gaggggaagc ct                              42

<210> SEQ ID NO 356
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 356
tcttccctgg tatgacctga crtccatctg acatggtccc tg                              42

<210> SEQ ID NO 357
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 357
aatagatgac tgtgaacagt grtggccagg gaactatctt ca                              42

<210> SEQ ID NO 358
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 358
gggcgtcaga gcagactgtc tmcccaaaga atcctccgaa gg                              42

<210> SEQ ID NO 359
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 359
gtgcacgagg tccagagata cmttgacctt ctccccacca gc                              42

<210> SEQ ID NO 360
<211> LENGTH: 42
<212> TYPE: DNA
```

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 360
tttcagtagg tttgcaggga arccaactca aagctatatc tg                           42

<210> SEQ ID NO 361
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 361
ttcctggcca cactgagaaa cmcctccttt ccttcgacac at                           42

<210> SEQ ID NO 362
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 362
cttggagagg cagataacgc traagcaggc ctctcatgac cc                           42

<210> SEQ ID NO 363
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 363
ctgggactgt ggatggatgt artttcgttt tttctagtct gt                           42

<210> SEQ ID NO 364
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 364
aagcatggat ctgggaggaa arcagcttgt gtgagttgga ta                           42

<210> SEQ ID NO 365
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 365
tcctggcttc cttctggacc crcaaggggc agtctcaaaa ta                           42
```

```
<210> SEQ ID NO 366
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 366
acacacatgt tcagcccaac trgagccttt tgtcagtaag tc                         42

<210> SEQ ID NO 367
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 367
ttatagattg tccagacatg arcagatcta tcacctgacc ac                         42

<210> SEQ ID NO 368
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 368
acaagtctct gaataagaag tsaggctggt gagcattctg gg                         42

<210> SEQ ID NO 369
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 369
cctaatctaa aattttctat trctacatca agggaacaat tt                         42

<210> SEQ ID NO 370
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 370
tcccaaggtg aatgatggtc traggacttc tggtggagag aa                         42

<210> SEQ ID NO 371
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g
```

```
<400> SEQUENCE: 371
atgtggggaa gctggaattc trgtatgtga aggtcaggaa ct                             42

<210> SEQ ID NO 372
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 372
cggggaggag gccctaattg tscaatgggg gccgcgtaaa tg                             42

<210> SEQ ID NO 373
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 373
cagaagtttt ttgatatttc crtttgaata ttttggtatc tg                             42

<210> SEQ ID NO 374
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 374
cctcagtgag aacggggagg awgtctagga caggaaagat gc                             42

<210> SEQ ID NO 375
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 375
acctgcctag tcctgggcct grcccttgtc tttggtgaag gg                             42

<210> SEQ ID NO 376
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 376
atacttattg agagaaagaa tsgatccaaa aaatcaaatc tt                             42

<210> SEQ ID NO 377
<211> LENGTH: 42
<212> TYPE: DNA
<213> ORGANISM: Homo sapiens
<220> FEATURE:
```

-continued

```
<221> NAME/KEY: misc_feature
<222> LOCATION: (22)..(22)
<223> OTHER INFORMATION: m = a or c

<400> SEQUENCE: 377
aagaagagat ctcttcaaga tmgataaaac agtgacctct gt          42

<210> SEQ ID NO 378
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 378
aaataaacca gaaattggta artcatcaca tggaaatcaa at          42

<210> SEQ ID NO 379
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 379
gaattggtcc accagcaaaa cmcatttgct tctccgtgga ct          42

<210> SEQ ID NO 380
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 380
ggaaaagaga cggcccggac asgcttcttt ccaaaacgtt ct          42

<210> SEQ ID NO 381
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 381
gcacctacac caacaattca grgtatccca ctgtaagata ta          42

<210> SEQ ID NO 382
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 382
ggcctccttt gctgccctca cratctcttc ctgtgacacc ac          42

<210> SEQ ID NO 383
```

<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 383
atgatattga attaaaggaa artgaatggt ctcagtcaga ga         42

<210> SEQ ID NO 384
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 384
ggcacattca tctttggcac crtcatctgc aaggcggttt cc         42

<210> SEQ ID NO 385
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 385
gtgtcccagt ttgaaggctc crccttggga aaacagctaa ag         42

<210> SEQ ID NO 386
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 386
tgaacactga gggtgaaaga crttagcatt cattgtcttt gt         42

<210> SEQ ID NO 387
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 387
actggatggt gagggtgtg grgataaagc ttctttctct tc         42

<210> SEQ ID NO 388
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 388
cagttgaata acatagtttt gsgggtgaat acaggcaagc aa    42

<210> SEQ ID NO 389
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 389
cagttttggt gtcaactaga araggtctta ttgaagttaa aa    42

<210> SEQ ID NO 390
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 390
cggctcttca gcatccgcca cmgcagcctc caccggcact cc    42

<210> SEQ ID NO 391
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 391
accacttccc gcccgtcggc crgcttctcc agcatcgacc ct    42

<210> SEQ ID NO 392
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 392
gaactcgatc tcgtagccgt grggcacccc catccacagg gg    42

<210> SEQ ID NO 393
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 393
tgagacaaga gatttggatc trgattgtat aaagaaatct ca    42

<210> SEQ ID NO 394
<211> LENGTH: 42
<212> TYPE: DNA
<213> ORGANISM: Homo sapiens
<220> FEATURE:
<221> NAME/KEY: misc_feature
<222> LOCATION: (22)..(22)

<223> OTHER INFORMATION: r = a or g

<400> SEQUENCE: 394
tcctttgaat aatcaaactg argaaggaga agcaagatgt ct    42

<210> SEQ ID NO 395
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 395
ctcagagtgg gactccttgc trgttccctg agctccctcg tt    42

<210> SEQ ID NO 396
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 396
tggggcggaa aggcgagatg grgctacgca ggcgcactag ga    42

<210> SEQ ID NO 397
<211> LENGTH: 42
<212> TYPE: DNA
<213> ORGANISM: Homo sapiens
<220> FEATURE:
<221> NAME/KEY: misc_feature
<222> LOCATION: (22)..(2)
<223> OTHER INFORMATION: r = a or g

<400> SEQUENCE: 397
ccagtgagca gcaacagggc crgggctggg cttatcagcc tc    42

<210> SEQ ID NO 398
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 398
tgtctcagtg gggccatggc crgcgcctca gggtctgaga ag    42

<210> SEQ ID NO 399
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 399
tggcaagtta gagagtcatt crttctttca aaatattta ct    42

<210> SEQ ID NO 400
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 400
agctggggcc tccactgtga tstcctctct cctgtaggag cc        42

<210> SEQ ID NO 401
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 401
tacagagacc agccgtcacg crggggccac atgtagctgg ct        42

<210> SEQ ID NO 402
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 402
ccagcaagat ctacttacaa crtactgcta tctgagaaca tt        42

<210> SEQ ID NO 403
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 403
cagagttgta tctctccttt artttgacta catgagggat gg        42

<210> SEQ ID NO 404
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 404
tgttggagag gcagctacca crtgcaccca gatggccact cg        42

<210> SEQ ID NO 405
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 405
gaaccattca aaaggaggtt grggggatca tgacacttcc at        42
```

```
<210> SEQ ID NO 406
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 406
caggaagaga ttgaacgtgt crttggcaga aaccggagcc cc                42

<210> SEQ ID NO 407
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 407
acaggtcagc caccaccatg crcaggttct catcattgaa gc                42

<210> SEQ ID NO 408
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 408
gaagcactgg tgcccctggc crtgatagtg gccatcttcc tg                42

<210> SEQ ID NO 409
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 409
tacccgcatc tcccaccccc argacgcccc tttcgcccca ac                42

<210> SEQ ID NO 410
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 410
ggtgacccgc ggcgaggaca csgccgaccg cccgcctgcg cc                42

<210> SEQ ID NO 411
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g
```

<400> SEQUENCE: 411
gtgggattta tgaaaagtgc crtctctata gctgaggatg aa                              42

<210> SEQ ID NO 412
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 412
cggcccatct aggaaccagg crgacacaga gaccctcggc ca                              42

<210> SEQ ID NO 413
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 413
tggaatctgc ccatgtgcag crggcctggg aacacatcaa ag                              42

<210> SEQ ID NO 414
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 414
acagctctga tgaagttttt grtttctccc cataaaaacc at                              42

<210> SEQ ID NO 415
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 415
tcatgatcgt gacctacacg crcatctacc gcatcgccca gg                              42

<210> SEQ ID NO 416
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: w = a or t

<400> SEQUENCE: 416
tcatgagcaa gatagaggcg twcatgttac agtaaaatgc tg                              42

<210> SEQ ID NO 417
<211> LENGTH: 42
<212> TYPE: DNA
<213> ORGANISM: Homo sapiens
<220> FEATURE:

```
<221> NAME/KEY: misc_feature
<222> LOCATION: (22)..(22)
<223> OTHER INFORMATION: r = a or g

<400> SEQUENCE: 417
cacagagttg ttaacatctc crtgaaacta attttaacca tg                             42

<210> SEQ ID NO 418
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 418
aacctcagca gcacctccca crtcccggag gtggacccgg gc                             42

<210> SEQ ID NO 419
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 419
cccatggcca caacagaact crcaaatggc agagctaggg ag                             42

<210> SEQ ID NO 420
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 420
atgttttaac tcataatagc tragcaaatg atgtccaagc aa                             42

<210> SEQ ID NO 421
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 421
cctgctcctg gcttcaaata trgaacggtg tctctgagag gc                             42

<210> SEQ ID NO 422
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 422
cacaatgcat ggttttgtgt amatttttaa gaattttgag gt                             42

<210> SEQ ID NO 423
```

```
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 423
gcgcttacct gtagccattg cmgctaggtg agctgtccac ag            42

<210> SEQ ID NO 424
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 424
gcagaagggg cagaggatga amtggaagtc cgggtcggta cc            42

<210> SEQ ID NO 425
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 425
atgtcttctg tcatggagat astgggattg cccccttggc tt            42

<210> SEQ ID NO 426
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 426
tgagccgagg aaaaacccag grgcgacaga tcctcggaga gc            42

<210> SEQ ID NO 427
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 427
aaagagtgaa gtcaattcaa crgattgaga agataatgca gt            42

<210> SEQ ID NO 428
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 428
```
aagaaaagta attgagaaaa grgggctcaa gatctctggc ta        42

<210> SEQ ID NO 429
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 429
gaccaaactt ggaagtgtaa arttatgcat gtatgttcat gt        42

<210> SEQ ID NO 430
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 430
acagaaaggg ccaaaaatca grgccaccac acacctgagc cc        42

<210> SEQ ID NO 431
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 431
tacccaataa gttttaaaat tmattttctt cctctattgc at        42

<210> SEQ ID NO 432
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 432
ggggaaaaat ctaatggcac crataaaatg gaggataata at        42

<210> SEQ ID NO 433
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 433
ttggcctatt ggtttggcaa tstgatattt ctgtgagccc ag        42

<210> SEQ ID NO 434
<211> LENGTH: 42
<212> TYPE: DNA
<213> ORGANISM: Homo sapiens
<220> FEATURE:
<221> NAME/KEY: misc_feature
<222> LOCATION: (22)..(22)

<223> OTHER INFORMATION: r = a or g

<400> SEQUENCE: 434
gcgcgccagc acccagcgcc crtacagcgc gttcagcatg gc                             42

<210> SEQ ID NO 435
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 435
cgcgcgcccc acaacaggaa arccttaggc ggcgcggctt gg                             42

<210> SEQ ID NO 436
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 436
accgtggtct gttccctgga crggctgttc ccagtctcgg ag                             42

<210> SEQ ID NO 437
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 437
gagtgggaga gttccctata grgcttggca tttgtttgtt tg                             42

<210> SEQ ID NO 438
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 438
ttctgcttaa atatggcttg tscattataa cataagttag gc                             42

<210> SEQ ID NO 439
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 439
gaatgagctc ggacatagct trgtgatgca tttgtctttta tc                            42

<210> SEQ ID NO 440
<211> LENGTH: 42
<212> TYPE: DNA

```
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 440
ttaatgactc catggcttat tragtgtagc ccagaaagaa tg                          42

<210> SEQ ID NO 441
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 441
ggtaaataaa agtcctttga crttagaagc cacgaaagaa ca                          42

<210> SEQ ID NO 442
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 442
ctgggtgagg ttgtggaaga graccatatc ctctggggac ag                          42

<210> SEQ ID NO 443
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 443
cggagaggtc ccagagggag grgcgaggtg gcctctgggg gg                          42

<210> SEQ ID NO 444
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 444
ggcctagaca taggaccagc crgccaccac gggggcaggg ag                          42

<210> SEQ ID NO 445
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 445
gcctccaatg ctgtatttaa trtttctcat tgttccccaa ga                          42
```

<210> SEQ ID NO 446
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 446
cttgctctcc tggtgagatg grtcttggcc tttgcacctg ga                              42

<210> SEQ ID NO 447
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 447
ggtagtccaa gggttcaccc artgtcagaa gaagtgtcct ta                              42

<210> SEQ ID NO 448
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 448
attgaatgag catccaaaag amgtatctgg agggagattt tg                              42

<210> SEQ ID NO 449
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 449
tagagaaata tgaaccatgg crgacaaata aaataccata tt                              42

<210> SEQ ID NO 450
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 450
cgaagtcctg acctatttgt artattttta ttcctaaagg aa                              42

<210> SEQ ID NO 451
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

```
<400> SEQUENCE: 451
ctgagggact ctgcctccaa crtcaccacc atccacaccc cg                          42

<210> SEQ ID NO 452
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 452
ctttctccag cccctcagat grcacagaac tacaaacccc ag                          42

<210> SEQ ID NO 453
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 453
aagttgtcct gggttgactc argaaggtag gatgagcatt ct                          42

<210> SEQ ID NO 454
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 454
caattcccgt tggttccgaa arttggaata ggtgccaagg at                          42

<210> SEQ ID NO 455
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 455
atcccatcaa ataatgtatg trcacaggaa ggtaacgggc cc                          42

<210> SEQ ID NO 456
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 456
tacccttaac tacaactcac tmtccccaca ggaagggccg cc                          42

<210> SEQ ID NO 457
<211> LENGTH: 42
<212> TYPE: DNA
<213> ORGANISM: Homo sapiens
<220> FEATURE:
```

<221> NAME/KEY: misc_feature
<222> LOCATION: (22)..(22)
<223> OTHER INFORMATION: r = a or g

<400> SEQUENCE: 457
cctatttcct gggatagaga arttgactag gcagagttcc ac                              42

<210> SEQ ID NO 458
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 458
tgatagtatg cttcgagaat arcaatctga tgatagcttt ca                              42

<210> SEQ ID NO 459
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 459
tatatgtttc tacaattata trtgttactg ggcatggtag ta                              42

<210> SEQ ID NO 460
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 460
tcccaatctg gacttcatag trctgaaact aatgcttgtc ag                              42

<210> SEQ ID NO 461
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 461
ttaaattggg aactaaaatt araacttcta ataacttcta ca                              42

<210> SEQ ID NO 462
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 462
ttgacattga ggaagggga trtcattttt aatcagacct ag                               42

<210> SEQ ID NO 463
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 463
tttgctggat ttgggcatgt arctaacagg tttgaggcat gg                              42

<210> SEQ ID NO 464
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 464
atataaaaaa gaaacttaaa grtaatcctc atcatggtaa aa                              42

<210> SEQ ID NO 465
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 465
ttttatttgt tgtgttgaat argaatgtag ctctgggaac ct                              42

<210> SEQ ID NO 466
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 466
cgtcctggcc ttctaaacgt asgacacatt gaaaaaatgc ag                              42

<210> SEQ ID NO 467
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 467
cgagcctagt aaatgttttt cmaagagcgc agtatggaaa gg                              42

<210> SEQ ID NO 468
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

```
<400> SEQUENCE: 468
tgtaattaaa tcagacagta graagactgg gctgctgccc tc                              42

<210> SEQ ID NO 469
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 469
gtgcagccta aatgtttata graaagtccc cttgaatatg ct                              42

<210> SEQ ID NO 470
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 470
tcctttccct cagcaaacag crtagtggtc atgtgtgtgg ca                              42

<210> SEQ ID NO 471
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 471
ctaagataaa cttaataatt crcattgaag acaaaaggca aa                              42

<210> SEQ ID NO 472
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 472
gcatggactc atccacacac grcatgacca cagcatccta at                              42

<210> SEQ ID NO 473
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 473
tattctaaag aaactaatat crattcatca gaaaattcaa ca                              42

<210> SEQ ID NO 474
<211> LENGTH: 42
<212> TYPE: DNA
<213> ORGANISM: Homo sapiens
```

```
<220> FEATURE:
<221> NAME/KEY: misc_feature
<222> LOCATION: (22)..(22)
<223> OTHER INFORMATION: r = a or g

<400> SEQUENCE: 474
cagtccaacg tggggtggg argaatttac atctttgcca cc                               42

<210> SEQ ID NO 475
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 475
gcctgtcagc aagcccggtg cmcttcgtcg ctccctgtcc cg                              42

<210> SEQ ID NO 476
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 476
aagtcgagta tgggacccc cmcttaacga agacagggcc at                              42

<210> SEQ ID NO 477
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 477
gatcaaaagc tataaggaaa argaggacag gaaggtcgtg ag                              42

<210> SEQ ID NO 478
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 478
gccgtgtaag caactaatac crgagtaagt gttatgctaa ta                              42

<210> SEQ ID NO 479
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 479
cgcatyggcc tctaygactc crtcaagcag gtgtacaccc cc                              42
```

```
<210> SEQ ID NO 480
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: s = c or g

<400> SEQUENCE: 480
gagctcccat tcacgaggcc ascactcatc tcgatttctg ga                              42

<210> SEQ ID NO 481
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 481
cccaggaact ggagcgaaag tragatttgc cccatgagga aa                              42

<210> SEQ ID NO 482
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 482
aggctgaggc aggagaatgg crtgaacccg ggaggcggag ct                              42

<210> SEQ ID NO 483
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 483
gatctcagag gctgtatacc cmcccagagt tattttatgc at                              42

<210> SEQ ID NO 484
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: m = a or c

<400> SEQUENCE: 484
ggcgaaaccc cgactctact amaactataa aaagccgggt gt                              42
```